United States Patent
Dixon et al.

(10) Patent No.: US 12,253,523 B2
(45) Date of Patent: *Mar. 18, 2025

(54) TARGET-BINDING ACTIVATED SPLIT REPORTER SYSTEMS FOR ANALYTE DETECTION AND RELATED COMPONENTS AND METHODS

(71) Applicant: UNIVERSITY OF UTAH RESEARCH FOUNDATION, Salt Lake City, UT (US)

(72) Inventors: Andrew S. Dixon, Salt Lake City, UT (US); Shawn Owen, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/453,745

(22) Filed: Aug. 22, 2023

(65) Prior Publication Data

US 2024/0210406 A1 Jun. 27, 2024

Related U.S. Application Data

(63) Continuation of application No. 16/840,713, filed on Apr. 6, 2020, now Pat. No. 11,774,453, which is a (Continued)

(51) Int. Cl.
*G01N 33/574* (2006.01)
*C07K 16/24* (2006.01)
(Continued)

(52) U.S. Cl.
CPC ..... *G01N 33/57488* (2013.01); *C07K 16/241* (2013.01); *C12Q 1/66* (2013.01);
(Continued)

(58) Field of Classification Search
CPC ............... G01N 33/542; G01N 33/581; C07K 2317/24; C12Q 1/6804
See application file for complete search history.

(56) References Cited

U.S. PATENT DOCUMENTS

| | | |
|---|---|---|
| 4,975,278 A | 12/1990 | Senter et al. |
| 5,256,395 A | 10/1993 | Barbet et al. |
| | (Continued) | |

FOREIGN PATENT DOCUMENTS

| | | |
|---|---|---|
| WO | 2012/061530 | 5/2012 |
| WO | 2013/126962 | 9/2013 |
| WO | 2014/151736 | 9/2014 |

OTHER PUBLICATIONS

Armbruster, et al., "Limit of Bank, Limit of Detection and Limit of Quantitation", Clin. Biochem. Rev., vol. 29 Suppl. (i), Aug. 2008, pp. S49-S52.

(Continued)

*Primary Examiner* — Changhwa J Cheu
(74) *Attorney, Agent, or Firm* — Michael Best & Friedrich LLP

(57) ABSTRACT

Split enzyme reporter systems are disclosed for detecting an analyte in a mixture. Fragments of the split enzyme may be covalently bound to targeting domains that bind to target regions of an analyte, thereby causing formation of an active complex. Some split enzyme reporter systems can be used to detect an analyte without the use of analyte immobilization, blocking, or wash steps. Some reporter systems also enable rapid detection of the analyte of interest.

28 Claims, 40 Drawing Sheets

Specification includes a Sequence Listing.

Related U.S. Application Data continuation of application No. 15/498,291, filed on Apr. 26, 2017, now Pat. No. 10,634,680.

(60) Provisional application No. 62/327,920, filed on Apr. 26, 2016.

(51) Int. Cl.
*C12Q 1/66* (2006.01)
*C12Q 1/6804* (2018.01)
*G01N 33/542* (2006.01)
*G01N 33/58* (2006.01)

(52) U.S. Cl.
CPC ......... *G01N 33/542* (2013.01); *G01N 33/581* (2013.01); *C07K 2317/24* (2013.01); *C12Q 1/6804* (2013.01); *G01N 2333/525* (2013.01)

(56) References Cited

U.S. PATENT DOCUMENTS

| | | |
|---|---|---|
| 5,837,242 A | 11/1998 | Hollinger et al. |
| 6,077,499 A | 6/2000 | Griffiths et al. |
| 7,335,478 B2 | 2/2008 | Balint et al. |
| 7,544,477 B2 | 6/2009 | Balint et al. |
| 7,833,528 B2 | 11/2010 | Griffiths et al. |
| 8,623,356 B2 | 1/2014 | Christopherson et al. |
| 2006/0257406 A1 | 11/2006 | Winter et al. |
| 2008/0248463 A1 | 10/2008 | Weiss et al. |
| 2010/0291543 A1 | 11/2010 | De Las Heras et al. |
| 2013/0004981 A1 | 1/2013 | Chiang et al. |
| 2013/0344094 A1 | 12/2013 | Gerg et al. |
| 2014/0011214 A1 | 1/2014 | McNaughton et al. |
| 2014/0271687 A1 | 9/2014 | Kovesdi et al. |
| 2014/0363375 A1 | 12/2014 | Dixon et al. |
| 2015/0079093 A1 | 3/2015 | Stuhler |

OTHER PUBLICATIONS

Backer, et al., "Self-Assembled "Dock and Lock" System for Linking Payloads to Targeting Proteins", Bioconjugate Chem. 17, 2006, pp. 912-919.

Ben-Horin et al., "Detection of infliximab in breast milk of nursing mothers with inflammatory bowel disease," J. Crohn's and Colitis, 2011, 5: 555-558.

Cabantous, et al., "A New Protein-Protein Interaction Sensor Based on Tripartite Split-GFP Association", Scientific Reports, 3: 2854, Oct. 4, 2013, 9 pages.

Carter, et al., "Humanization of an anti-p185HER2 antibody for human cancer therapy", Proc. Natl. Acad. Sci. USA, vol. 89, May 1992, pp. 4285-4289.

Cho, et al., "Structure of the extracellular region of HER2 alone and in complex with the Herceptin Fab", Nature, vol. 421, Feb. 13, 2003, pp. 756-760.

Di Gioia, et al., "Serum HER2 supports HER2-testing in tissue at the lime of primary diagnosis of breast cancer", Clinica Chimica Acta, 430, 2014, pp. 86-91.

Dixon, et al., "Nanoluc Complementation Report Optimized for Accurate Measurement of Protein Interactions in Cells", ACS Chem. Biol. 11, 2016, pp. 400-408.

Dixon, et al., "NanoLuc Complementation Reporter Optimized for Accurate Measurement of Protein Interactions in Cells", 2016, 33 pages.

Eigenbrot, et al., "Structural basis for high-affinity HER2 receptor binding by an engineered protein", PNAS, vol. 107, No. 34, Aug. 24, 2010, pp. 15039-15044.

Engvall, et al., "Enzyme-linked immunosorbent assay (ELISA) Quantiative assay of immunoglobulin G", IMM vol. 8, No. 9, 1971, pp. 871-874.

EPA, "Structural Model for the Interaction of a Designed Ankyrin Repeat Protein with the Human Epidermal Growth Factor Receptor 2", PLOS One, vol. 8, Issue 3, Mar. 2013, pp. 1-10.

Esteva, et al., "Clinical utility of serum HER2/neu in monitoring and predicition of prograssion-free survival in metastatic breast cancer patients treated with trastuzumab-based therapies", Breast Cancer Research; 7, 2005, pp. R436-R443.

Fisher, et al., "Structure of the Complex between HER2 and an Antibody Paratope Formed by Side Chains from Tryptophan and Serine", J. Mol. Biol.; 402, 2010, pp. 217-229.

Franciotta et al., "TE671 cell-based ELISA for anti-acetylcholine receptor antibody determination in myasthenia gravis," Clinical Chem., 1999, vol. 45:3, 400-405.

Franklin, et al., "Insights into ErbB signaling from the structure of the ErbB2-pertuzumab complex", Cancer Cell, vol. 5, Apr. 2004, pp. 317-328.

Girish, et al., "Clinical pharmacology of trastuzumab emtansine {T-DM1}: an anti-body-drug conjugate in development for the treatment of HER2-positive cancer", Cancer Chemother Pharmacol 69, 2012, pp. 1229-1240.

Hall, et al., "Engineered Luciferase Reporter from a Deep Sea Shrimp Utilizing a Novel Imidazopyrazinone Substrate", ACS Chem. Biol. 7, 2012, pp. 1848-1857.

Hechtman, et al., "HER2/neu Gene Amplification and Protein Overexpression in Gastric and Gastroesophageal Junction Adenocarcinoma", Arch Pathol Lab Med, vol. 136, Jun. 2012, pp. 691-697.

Heinmoller, et al., "HER2 Status in Non-Small Cell Lung Cancer: Results from Patient Screening for Enrollment to a Phase II Study of Herceptin", Clinical Cancer Research, vol. 9, Nov. 1, 2003, pp. 5238-5244.

Hooper, Ph.D., "Application of a smaller, brighter, more versatile luciferase", Nanoluc {TM} Luciferase Technology, Fall 2012, 41 pages.

International Search Report and Written Opinion for Application No. PCT/US2017/029680 dated Sep. 18, 2017 (17 pages).

Jamieson et al., "Development and validation of cell-based ELISA for the quantification of trastuzumab in human plasma," J. Immunological Methods, 2009, 345: 106-111.

Jorgensen, "Role of human epidermal growth factor receptor 2 in gastric cancer: Biological and pharmacological aspects", World J Gastroenterol 20(16), Apr. 28, 2014, pp. 4526-4535.

Jost, et al., "Structural Basis for Eliciting a Cytotoxic Effect in HER2-Overexpressing Cancer Cells via Binding to the Extracellular Domain of HER2", Structure; 21, Nov. 5, 2013, pp. 1979-1991.

Kerppola, "Visualization of molecular interactions using bimolecular fluorescence complementation analysis: Characteristics of protein fragment complementation", Chem. Soc. Rev., 38, 2009, pp. 2876-2886.

Kurebayashi, "Biological and Clinical Significane of HER2 Overexpression in Breast Cancer", Breast Cancer, vol. 8, No. 1, Jan. 2001, pp. 45-51.

Lewis, et al., "Generation of bispecific IgG antibodies by structure-based design of an orthogonal Fab interface", Nature Biotechnology, vol. 32, No. 2, Feb. 2014, pp. 191-202.

Lorusso, et al., "Trastuzumab Emtansine: A Unique Antibody-Drug Conjugate in Development for Human Epidermal Growth Factor Receptor 2-Positive Cancer", Clinical Cancer Research 17 (20), Oct. 15, 2011, pp. 6437-6447.

Luker, et al., "Kinetics of regulated protein-protein interactions revealed with firefly luciferase complementation imaging in cells and living animals", PNAS, vol. 101, No. 33, Aug. 17, 2004, pp. 12288-12293.

McAlpine, et al., "HER2 overexpression and amplification is present in a subset of ovarian mucinous carcinomas and can be targeted with trastuzumab therapy", BMC Cancer 9:433, Dec. 10, 2009, 12 pages.

Menard, et al., "Role of HER2 Gene Overexpression in Breast Carcinoma", Journal of Cellular Physiology 182, 2000, pp. 150-162.

Miller, et al., "Bimolecular Fluorescence Complementation (BiFC) Analysis: Advances with Recent Applications for Gene-Wide Interaction Studies", J Mol Biol 427, 2015, pp. 2039-2055.

Nesbitt et al., "Mechanism of action of certolizumab pegol (CDP870): in vitro comparison with other anti-tumor necrosis factor alpha agents," Inflammatory Bowel Diseases, 2011, 13(11): 1323-1332.

(56) References Cited

OTHER PUBLICATIONS

Ohmuro-Matsuyama, et al., "Demonstration of protein-fragment complementation assay using protein firefly luciferase fragments", BMC Biotechnology, 13:31, 2013, 9 pages.

Owen, et al., "Targeting HER2 + breast cancer cells: Lysosomal accummulation of anti-HER2 antibodies is influenced by antibody binding site and conjugation to polymeric nanoparticles", Journal of Controlled Release; 172, 2013, pp. 395-404.

Paulmurugan, et al., "Monitoring Protein—Protein Interactions Using Split Synthetic Renilla Luciferase Protein-Fragment-Assisted Complementation", Analytical Chemistry, vol. 75, No. 7, Apr. 1, 2003, pp. 1584-1589.

Pegram, et al., "Phase II Study of Receptor-Enhanced Chemosensitivity Using Recombinant Humanized Anti-p185HER2/neu Monoclonal Antibody Plus Cisplatin in Patients With HER2/neu-Overexpressing Metastatic Breast Cancer Refractory to Chemotherapy Treatment", Journal of Clinical Oncology, vol. 16, No. 8, Aug. 1998, pp. 2659-2671.

Phillips, et al., "Targeting HER2-Positive Breast Cancer with Trastuzumab-DM1, an Antibody-Cytotoxic Drug Conjugate", Cancer Research 2008; 68: (22), Nov. 15, 2008, 12 pages.

Plosker, et al., "Trastuzumab: A Review of its Use in the Management of HER2-Positive Metastatic and Early-Stage Breast Cancer", Drugs; 66(4), 2006, pp. 449-475.

Remy, et al., "A highly sensitive protein-protein interaction assay based on Gaussia Luciferase", Nature Methods, vol. 3, No. 12, Dec. 2006, pp. 977-979.

Remy, et al., "Mapping Biochemical Networks with Protein-Fragment Complementation Assays", Methods in Molecular Biology, 2004, vol. 261, pp. 411-426.

Ross, et al., "Targeted Therapy in Breast Cancer", Molecular & Cellular Proteomics 3.4, 2004, pp. 379-398.

Ross, et al., "The HER-2/neu Gene and Protein in Breast Cancer 2003: Biomarker and Target of Therapy", The Oncologist; 8, 2003, pp. 307-325.

Santin, et al., "Overexpression of HER-2/Neu in Uterine Serous Papillary Cancer", Clinical Cancer Research, vol. 8, May 2002, pp. 1271-1279.

Shekhawat, et al., "Split-protein systems: beyond binary protein-protein interactions", Current Opinion in Chemical Biology, 15, 2011, pp. 789-797.

Stains, et al., "A General Approach for Receptor and Antibody-Targeted Detection of Native Proteins Utilizing Split-Luciferase Reassembly", ACS Chemical Biology, vol. 5, No. 10, 2010, pp. 943-952.

Teplinksky, et al., "Targeting HER2 in ovarian and uterine cancers: Challenges and future directions", Gynecologic Oncology 135, 2014, pp. 364-370.

Tinghe, et al., "ELISA in the multiplex era: Potentials and pitfalls", Proteomics Clin. Appl. 9, 2015, pp. 406-422.

Todeschini, et al., "Her2/neu extracellular domain shedding in uterine serous carcinoma: implications for immunotherapy with trastuzumab", British Journal of Cancer; 105, 2011, pp. 1176-1182.

Tse, et al., "HER2 shedding and serum HER2 extracellular domain: Biology and clinical utility in breast cancer", Cancer Treatment Reviews; 38, 2012, pp. 133-142.

Tsien, "The Green Fluorescent Protein," Annual Review of Biochemistry, 1998, vol. 67, pp. 509-544.

Van Weemen, et al., "Immunoassay Using Antigen—Enzyme Conjugates", FEBS Letters vol. 5, No. 3, Jun. 1971, 5 pages.

Walshe, et al., "A Phase II Trial with Trastuzumab and Pertuzumab in Patients with HER2-Overexpressed Locally Advanced and Metastatic Breast Cancer", Clinical Breast Cancer, vol. 6, No. 6, 2006, pp. 535-539.

Wesola, et al., "A Comparison of IHC and FISH Cytogenic Methods in the Evaluation of HER2 Status in Breast Cancer", Adv Clin Exp Med; 24, 2015, pp. 899-904.

Witzell, et al., "Monitoring serum HER2 levels during neoadjuvant trastuzumab treatment within the GeparQuattro trial", Breast Cancer Res Treat; 123, 2010, pp. 437-445.

Yan et al., "Indexing TNF-α gene expression using a gene-targeted reporter cell line," BMC Biology, 2009, 7(8): 1-10.

Yu, et al., "Overexpression of ErbB2 in cancer and ErbB2-targeting strategies", Oncogene; 19, 2000, pp. 6115-6121.

Zahnd, et al., "A Desined Ankyrin Repeat Protein Evolved to Picomolar Affinity to HER2", J. Mol. Biol.; 369, 2007, pp. 1015-1028.

Zhou, et al., "Structural Insights into the Down-regulation of Overexpressed p185her2/neu Protein of Transformed Cells by the Antibody chA21", Journal of Biological Chemistry, vol. 286, No. 36, Sep. 9, 2011, pp. 31676-31683.

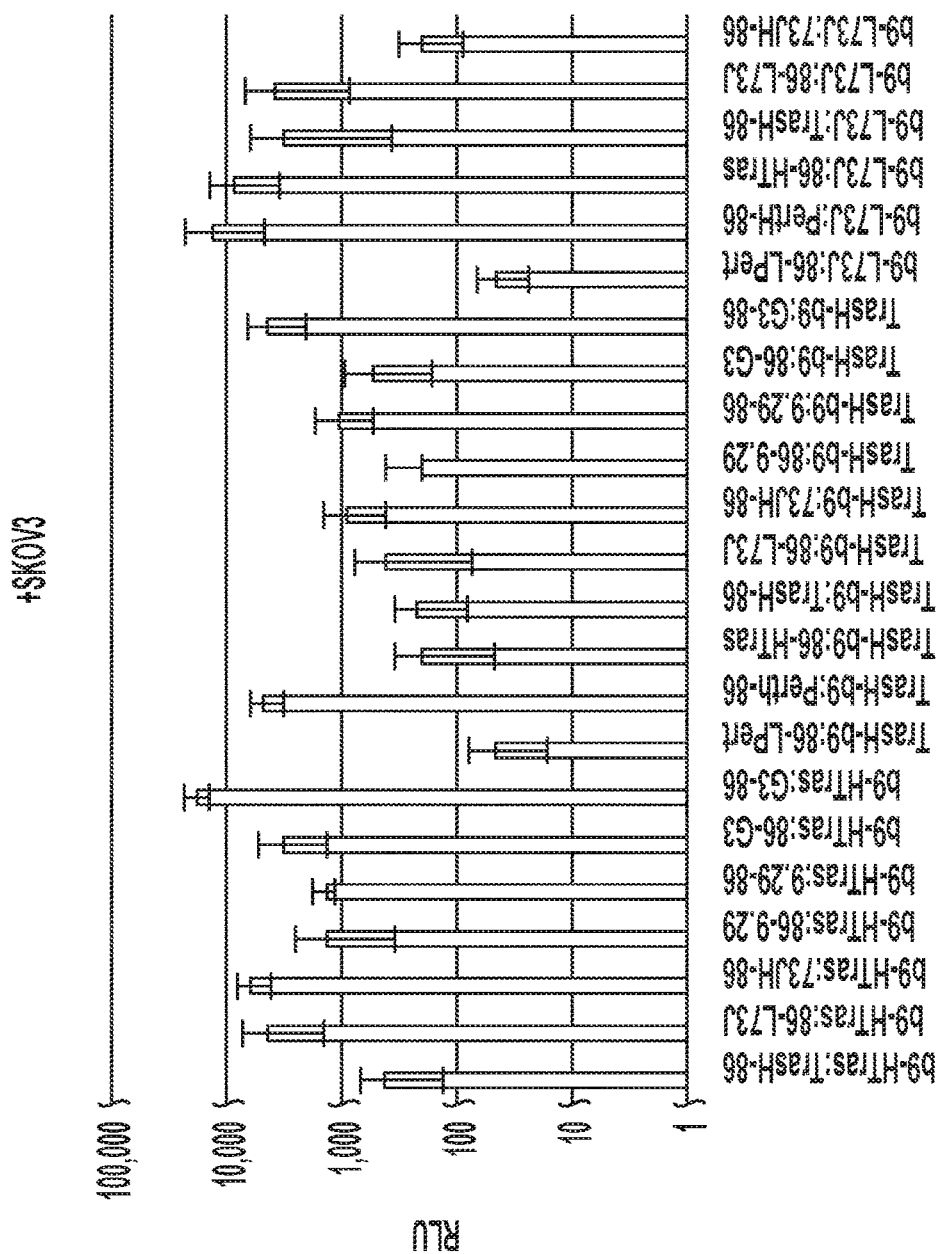
FIG. 13 (Contd.)

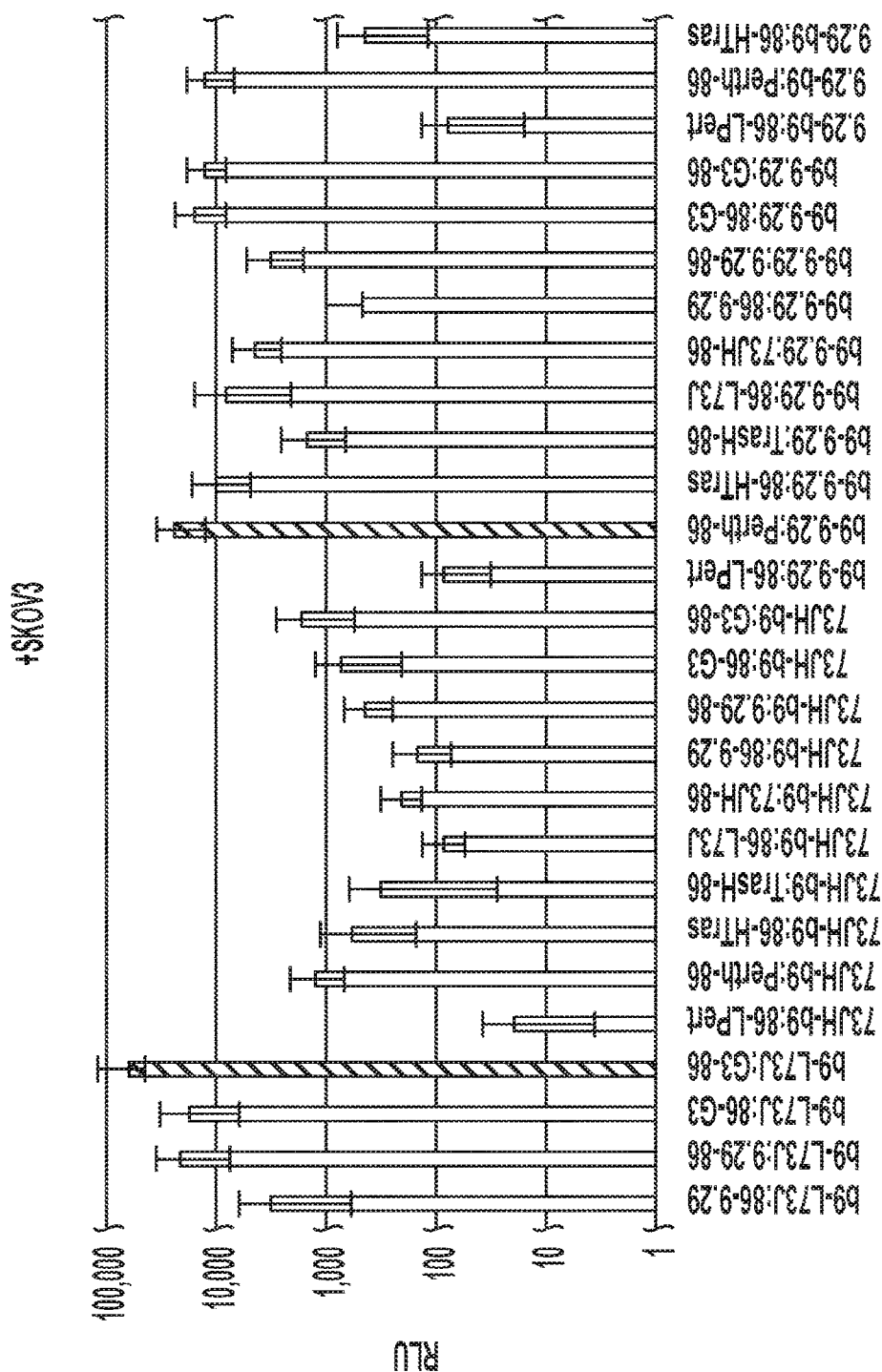
FIG. 13 (Contd.)

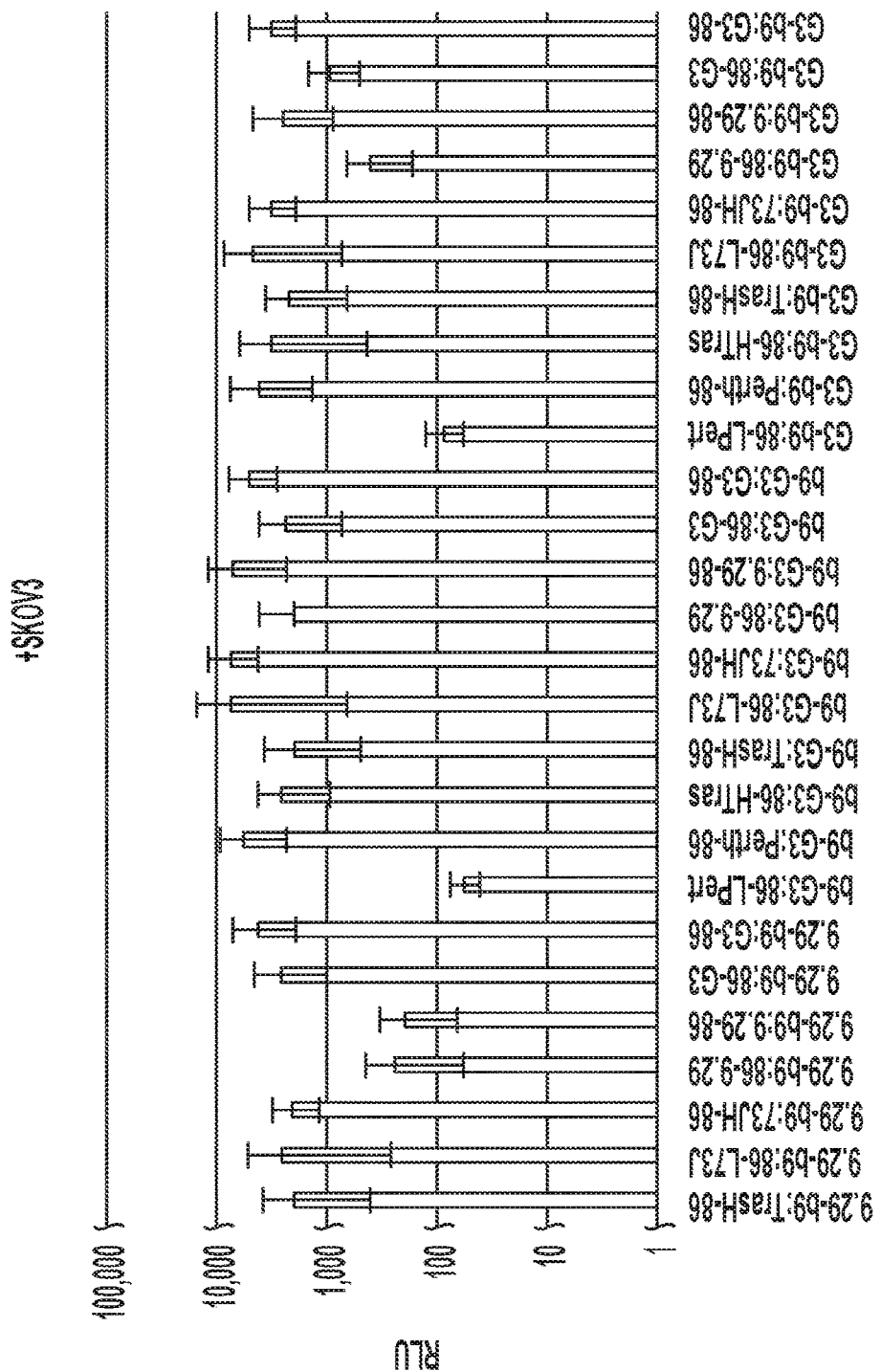
FIG. 13 (Contd.)

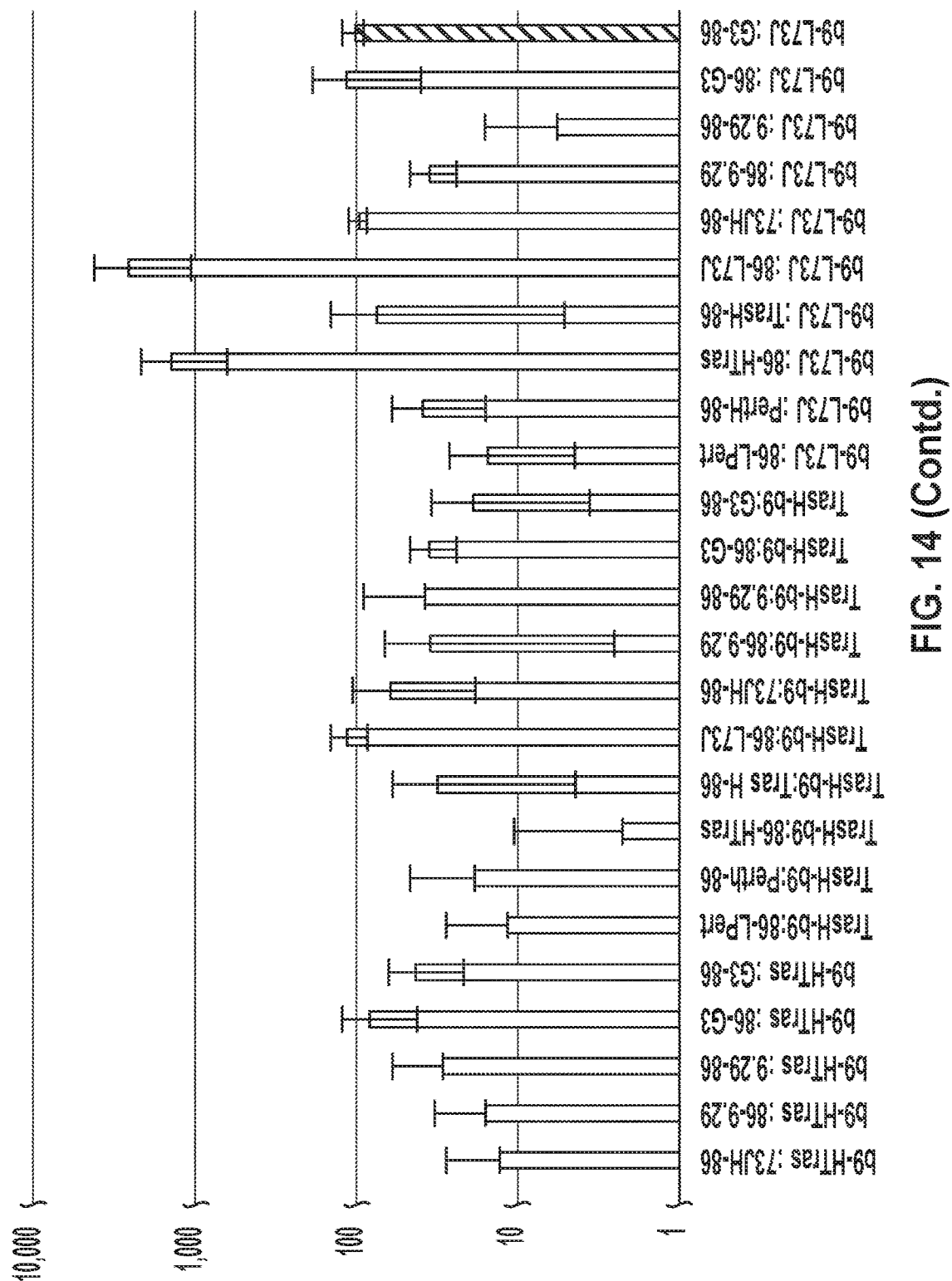
FIG. 14 (Contd.)

TARGET-BINDING ACTIVATED SPLIT REPORTER SYSTEMS FOR ANALYTE DETECTION AND RELATED COMPONENTS AND METHODS

CROSS-REFERENCE TO RELATED APPLICATION(S)

This application is a continuation of U.S. patent application Ser. No. 16/840,713, filed on April 6, 2020, which is a continuation of U.S. patent application Ser. No. 15/498,291, filed on Apr. 26, 2017, now issued as U.S. Pat. No. 10,634,680 on Apr. 28, 2020, which claims priority to U.S. Provisional Patent Application No. 62/327,920, filed on April 26, 2016, the entire contents of each of which are fully incorporated herein by reference.

INCORPORATION-BY-REFERENCE OF MATERIAL SUBMITTED ELECTRONICALLY

This application was filed with a Sequence Listing XML in ST.26 XML format in accordance with 37 C.F.R. § 1.821. The Sequence Listing XML file submitted in the USPTO Patent Center, "026389-9235-US04.xml," was created on Aug. 22, 2023, contains 96 sequences, has a file size of 161 Kbytes, and is incorporated by reference in its entirety into the specification.

TECHNICAL FIELD

The present disclosure relates generally to the fields of biotechnology and analyte detection. More particularly, the present disclosure relates to split reporters, such as split reporter proteins that are configured to bind to and facilitate detection of an analyte or analytes in a mixture.

BACKGROUND

Modern research and medicine involve qualitatively assessing and/or quantitatively measuring one or more analytes in a mixture. For example, in research settings, the identification and quantification of biomolecules, such as proteins, nucleic acids, sugars, lipids, etc., is important to understanding the mechanistic underpinnings of cellular processes. In clinical settings, the detection of biomarkers can enable the diagnosis of a disease, facilitate a more accurate prognosis for the patient, and/or provide a mechanism for monitoring therapeutic outcomes. As such, the ability to accurately and reliably detect analytes (e.g., biomolecules) in a timely manner is highly important.

For decades, researchers have relied on various immunoassays, such as ELISAs, western blots, immunocytochemistry, and/or immunohistochemistry for biomolecule (e.g., protein) detection. Such immunoassays may be time-consuming (e.g., >6 hours) and labor-intensive. One factor contributing to the labor and time required for some immunoassays is the need to remove excess (i.e., unbound) antibodies. For example, some immunoassays require numerous wash steps before and after addition of a primary antibody and a secondary antibody. Some immunoassays additionally or alternatively require one or more blocking steps and/or immobilization of the analyte. Some immunoassays cannot be carried out in a homogeneous solution.

Split proteins have been used for the detection and/or quantification of protein interactions. Various names have been given to the processes used for such detection and/or quantification, such as protein-fragment complementation assays (Michnick et al., *Nat Rev Drug Discov* 6, 569-82 (2007); Remy & Michnick, *Methods Mol Biol* 1278, 467-81 (2015)), split protein complementation (Shekhawat & Ghosh, *Curr Opin Chem Biol* 15, 789-97 (2011)), or bimolecular fluorescence complementation (Miller et al., *J Mol Biol* 427, 2039-55 (2015); Kerppola, T. K., *Chem Soc Rev* 38, 2876-2886 (2009)). In these split protein systems, each fragment of the split protein is individually inactive. However, when the fragments of a split protein are combined at high concentrations, the fragments can form an active protein complex. This ability to turn on the activity of the split protein can be exploited to monitor protein interactions by fusing each peptide fragment of the split protein to different proteins that have affinity for one another. The interaction between these different proteins creates a high local concentration of the two peptide fragments, thereby causing the separate fragments of the split protein to bind to one another to form an active protein complex.

Several split proteins have been used in complementation assays, including β-lactamase, β-galactosidase, dihydrofolate reductase, green fluorescent protein, ubiquitin, and TEV protease (Morrell et al., *FEBS Lett* 583, 1684-91 (2009). One split protein that has been used to detect and quantify protein interactions is NanoBiT® (Promega®). NanoBiT® is a split and modified form of NanoLuc® (Promega®), an engineered luciferase derived from a deep sea luminous shrimp (Dixon et al., *ACS Chem Biol* 11, 400-08 (2016)). The split NanoBiT® enzyme includes a relatively short peptide fragment (11 amino acids) and a relatively long peptide fragment (an 18 kDa polypeptide).

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
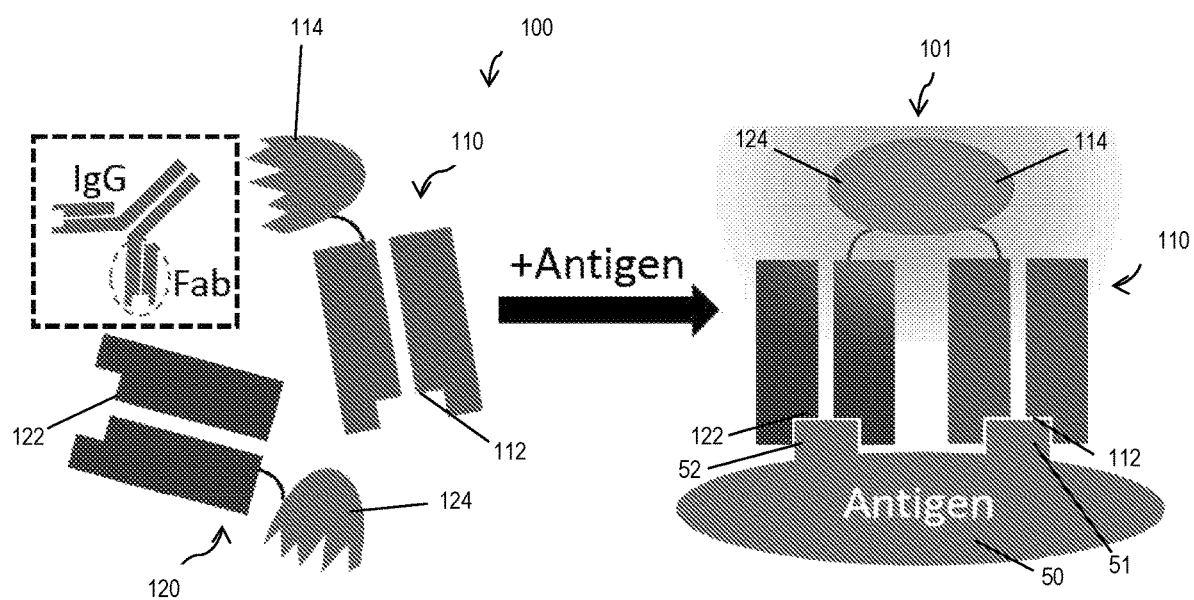
FIG. 1 is a schematic representation of components of a target-binding activated split reporter system.

The following detailed description of various embodiments is not intended to limit the scope of the disclosure, but is merely representative of various embodiments. The present disclosure relates generally to split reporter systems, including split reporter systems for use in detecting and/or measuring an analyte.

"Enzymatic activity" includes the catalytic activity of a complex formed by fragment complementation. A "homomultimeric protein complex" includes homodimers, homotrimers, homotetramers, etc. A "heteromultimeric protein complex" includes heterodimers, heterotrimers, heterotetramers, etc. The term "domain" is not limited to protein domains. The term "peptide" or "peptide fragment" can refer to any chain of amino acids, regardless of length.

Immunoassays can be used to detect and/or quantify an analyte, such as a biomolecule. Many immunoassays require labor-intensive, time-consuming, multi-step protocols in order to remove unbound or non-specific targeting domains, thereby enabling specific detection due to binding of the analyte. Certain embodiments disclosed herein may provide advantages over known immunoassays, such as by decreasing the amount of labor (and thereby reducing the potential for human error), decreasing the time involved, decreasing the number of steps required to obtain a specific and/or measurable signal, and/or enabling detection/quantification under conditions that are not feasible with known immunoassays. Some embodiments can be used to monitor the presence, level, location, change in level, or change in location of an analyte.

Some embodiments disclosed herein involve the use of a split reporter protein, which may also be referred to as a split reporter or a split reporter protein complex. In some embodiments, the split reporter is a binary (i.e., two-part) reporter. In other embodiments, the split reporter is a ternary (i.e., three-part or tripartite) reporter. The individual fragments of the split reporter may be individually inactive. However, when combined with complementary peptide fragment(s) of the split reporter, the peptide fragments may bind to one another to form an active protein complex. Examples of split reporter proteins include split green fluorescent protein (Cabantous et al., *Sci Rep* 3, 2854 (2013)), NanoBiT®, and split β-lactamase. In some embodiments, the split reporter protein does not include a cysteine residue.

In some embodiments, the split reporter protein is a beta-barrel protein, such as a 10-stranded beta-barrel protein. In some embodiments, the split reporter protein is a split fluorescent protein, such as a split green fluorescent protein (e.g., a binary split fluorescent protein or a ternary split fluorescent protein). In other embodiments, the split reporter protein is a split enzyme. The split enzyme may catalyze the conversion of a substrate to a product. The activity of the split enzyme on the substrate may result in the emission of a detectable (e.g., luminescent) signal. For example, in some embodiments, the split enzyme is a split luciferase. In some embodiments, the substrate for the split enzyme is luciferin, furimazine, or some other luminogenic substrate or molecule. In some embodiments, the split enzyme catalyzes the conversion of furimazine to furimamide. In some embodiments, the enzymatic activity of the split enzyme is not natively found in mammals. In some embodiments, the split enzyme has no eukaryotic ortholog.

In some embodiments, the split reporter protein is a three-part (i.e., tripartite or ternary) complex that includes a first agent, a second agent, and a third agent. The first agent may include a first targeting domain and a first peptide fragment of a split reporter protein. The second agent may include a second targeting domain and a second peptide fragment of the split reporter protein. The third agent may include a third fragment of the split reporter protein.

The targeting domains of the first agent and the second agent may be any suitable targeting domain. For example, in some embodiments, the targeting domains of one or both of the first agent and the second agent comprise or consist of an antibody, an antigen, a designed ankyrin repeat protein (DARPin), an affibody, ubiquitin, a known interaction partner, a ligand, an aptamer, adnectin (monobody or Fibronectin type II domain), or a portion thereof. For example, in some embodiments, the targeting domains of one or both of the first agent and the second agent may be a fragment antigen binding fragment (Fab), a single-chain variable fragment, IgG, etc. In some embodiments, one or more targeting domains are monoclonal antibodies or portions thereof. In some embodiments, one or both targeting domains are polyclonal antibodies, or portions thereof. In some embodiments, one or more targeting domains are immunoglobulin-binding proteins, such as protein A, protein G, protein A/G, or protein L.

The first targeting domain may be configured to selectively bind to a first target region of an analyte, and the second targeting domain may be configured to selectively bind to a second target region of the analyte. For example, a first targeting domain may be configured to selectively bind to a first epitope of an analyte, while the second targeting domain is configured to selectively bind to a second epitope of the analyte. In some embodiments, the first target region and the second target region are different in structure (e.g., different epitopes). In other embodiments, the first target region and the second target region are identical or substantially identical in structure (e.g., identical or substantially identical epitopes), but are located at separate sites on the analyte (e.g., the protein). In some embodiments, the first target region and the second target region are separated by less than 300 (e.g., less than 150) angstroms. For example, in some embodiments, the first target region is separated from the second target region by 2-300 angstroms, 2-200 angstroms, 2-175 angstroms, 2-150 angstroms, 2-125 angstroms, 2-100 angstroms, 2-75 angstroms, 2-50 angstroms, 2-25 angstroms; 25-300 angstroms, 50-300 angstroms, 75-300 angstroms, 100-300 angstroms, 125-300 angstroms, 150-300 angstroms, 10-150 angstroms; 25-145 angstroms; 35-145 angstroms, 40-145 angstroms, 50-125 angstroms, or 60-100 angstroms. In some embodiments, the first and second target regions (e.g., epitopes) do not overlap.

The first peptide fragment and the second peptide fragment may be relatively short peptide fragments. Stated differently, one or both of the first peptide fragment and the second peptide fragment may have a mass of less than about 3 kDa. In some embodiments, the first peptide fragment is less than or equal to 15, 14, 13, 12, and/or 11 amino acids in length. In some embodiments, the second peptide fragment is less than or equal to 15, 14, 13, 12, and/or 11 amino acids in length. For example, in some embodiments, both the first peptide fragment and the second peptide fragment are each 11 amino acids in length. The relatively short length of the peptide fragments may facilitate expression, reduce aggregation, improve solubility, and/or improve the stability of agents that are produced as fusion proteins. Such small peptide fragments may also be less likely to interfere with binding of the targeting domain to the analyte.

In some embodiments, the first peptide fragment has at least 80%, 90%, or 100% sequence identity to the sequence of SEQ ID NO 1 (i.e., VSGWRLFKKIS). In some embodiments, the second peptide fragment has at least 80%, 90%, or 100% sequence identity to the sequence of SEQ ID NO 2 (i.e., GSMLFRVTINS).

In some embodiments, the first peptide fragment corresponds with a C-terminal beta sheet (β10) of a 10-stranded beta-barrel protein. In some embodiments, the second peptide fragment corresponds with the ninth beta sheet of a 10-stranded beta-barrel protein. In some embodiments, the first targeting domain of the first agent is positioned on the N-terminal side of a β10 fragment. In other embodiments, the first targeting domain of the first agent is positioned on the C-terminal side of a 10 fragment. In some embodiments, the second targeting domain of the second agent is positioned on the N-terminal side of a fragment corresponding to the ninth beta sheet. In other embodiments, the second targeting domain of the second agent is positioned on the C-terminal side of a fragment corresponding to the ninth beta sheet. In some embodiments, the peptide fragment and the targeting domain are connected via a linker. In some embodiments, the linker is a peptide. In other embodiments, the linker is not a peptide.

In some embodiments, one or both of the first agent and the second agent are recombinant fusion proteins. In some embodiments, the fusion proteins include a solubilizing protein or domain (e.g., HaloTag®, (Promega)). In other embodiments, one or both of the first agent and the second agent are formed by synthetically conjugating or enzymatically ligating a peptide fragment to a targeting domain. Such conjugation may facilitate the use of polyclonal antibodies or antibodies from hybridomas where the sequence of the targeting domain is not known. In some embodiments, a peptide fragment is conjugated to a targeting domain via an exposed sulfide (e.g., a cysteine residue) or an exposed amine (e.g., a lysine residue) on the targeting domain. In some embodiments, the targeting domain is modified to include a sulfhydryl group. For example, in some embodiments, 2-iminothiolane is used to modify a primary amine of a targeting domain to form an exposed sulfhydryl group. In some embodiments, a maleimide may be used to attach a peptide fragment to an exposed sulfhydryl group on a targeting domain (e.g., an antibody).

In some embodiments that include a third peptide fragment, the third peptide fragment has a mass of between 16 kDa and 17 kDa. In some embodiments, the third peptide fragment has at least 70%, 80%, 90%, 95% or 100% sequence identity to the sequence of SEQ ID NO 3. In some embodiments, the third peptide fragment has between 140 and 150 amino acids. For example, in some embodiments, the third peptide has between 145 and 150 amino acids (e.g., 148 amino acids).

The analyte to be detected and/or measured may be any suitable analyte. In some embodiments, the analyte is a biomolecule, such as a protein, nucleic acid, carbohydrate, or lipid. In some embodiments, the analyte has a monomeric quaternary structure (i.e., the analyte is not a dimer, trimer, etc.). In other embodiments, the analyte has a higher quaternary structure. For example, the analyte may be a dimer, a trimer, a tetramer, or any other multimeric complex. In some embodiments, the analyte is a modified protein, such as a phosphorylated protein, a glycosylated protein, or an antibody-drug conjugate (e.g., trastuzumab emtansine (Kadcyla®) or brentuximab vedotin (Adcetris®)). In some embodiments, the analyte is an antibody, such as a natural, synthetic, or recombinant antibody (or a portion thereof). In some embodiments, the analyte is an antibody formed in response to an allergen, a bacterial infection, or a viral infection.

As noted above, in some embodiments, the analyte is a monomeric protein. In some embodiments, the monomeric protein may have a first target region and a second target region that are different structures (e.g., epitopes) on the monomeric protein. In other words, the first target region and the second target region of the monomeric protein may be significantly different in structure. In other embodiments, the monomeric protein may have a first target region and a second target region that are substantially identical epitopes located at separate sites on the monomeric protein.

In some embodiments, the analyte is a multimeric protein complex. The multimeric protein complex may be a homomultimeric protein complex or a heteromultimeric protein complex. In some embodiments in which the analyte is a multimeric protein complex, the first targeting domain and the second targeting domain bind to adjacent proteins of the multimeric protein complex. Because the split reporter produces a signal only when the peptide fragments are in proximity to one another, the split reporter may be used to assess complex formation. Stated differently, split reporter systems that include both (1) a first peptide fragment that is attached to a first targeting domain that binds a first protein of a protein complex and (2) a second peptide fragment that is attached to a second targeting domain that binds to a second protein of a protein complex may be used to identify and/or quantify complex formation.

In some embodiments, the analyte is a soluble protein or biomolecule. For example, in some embodiments the analyte is a naturally occurring, endogenous, or xenobiotic protein or biomolecule. In some embodiments, the analyte is a growth factor, cytokine, hormone, a growth factor receptor, a cytokine receptor, or a hormone receptor. For example, the analyte may be selected from any of the following: adrenomedullin (AM), angiopoietin (Ang), autocrine motility factor, bone morphogenetic proteins (BMPs), ciliary neurotrophic factor family, ciliary neurotrophic factor (CNTF), leukemia inhibitory factor (LIF), interleukin-6 (IL-6), colony-stimulating factors, macrophage colony-stimulating factor (m-CSF), granulocyte colony-stimulating factor (G-CSF), granulocyte macrophage colony-stimulating factor (GM-CSF), epidermal growth factor (EGF), ephrins, ephrin A1, ephrin A2, ephrin A3, ephrin A4, ephrin A5, ephrin B1, ephrin B2, ephrin B3, erythropoietin (EPO), fibroblast growth factor (FGF) foetal bovine somatotrophin (FBS), a ligand from the GDNF family, glial cell line-derived neurotrophic factor (GDNF), neurturin, persephin, artemin, growth differentiation factor-9 (GDF9), hepatocyte growth factor (HGF), hepatoma-derived growth factor (HDGF), insulin, insulin-like growth factors, insulin-like growth factor-1 (IGF-1), insulin-like growth factor-2 (IGF-2), interleukins, IL-1, IL-2, IL-3, IL-4, IL-5, IL-6, IL-7, keratinocyte growth factor (KGF), migration-stimulating factor (MSF), macrophage-stimulating protein (also known as hepatocyte growth factor-like protein (HGFLP)), myostatin (GDF-8), neuregulins, neuregulin 1 (NRG1), neuregulin 2 (NRG2), neuregulin 3 (NRG3), neuregulin 4 (NRG4), neurotrophins, brain-derived neurotrophic factor (BDNF), nerve growth factor (NGF), neurotrophin-3 (NT-3), neurotrophin-4 (NT-4), placental growth factor (PGF), platelet-derived growth factor (PDGF), renalase (RNLS), T-cell growth factor (TCGF), thrombopoietin (TPO), transforming growth factors, transforming growth factor alpha (TGF-α), transforming growth factor beta (TGF-β), tumor necrosis factor (also known as tumor necrosis factor alpha (TNF-α)), vascular endothelial growth factor (VEGF), amylin (or islet amyloid polypeptide), anti-Müllerian hormone (or Müllerian-inhibiting factor or hormone), adiponectin, adrenocorticotropic hormone (or corticotropin), angiotensinogen, angiotensin, antidiuretic hormone (or vasopressin, arginine vasopressin), atrial-natriuretic peptide (or atriopeptin), brain natriuretic peptide, calcitonin, cholecystokinin, corticotropin-releasing hormone, cortistatin, enkephalin, endothelin, erythropoietin, follicle-stimulating hormone, galanin, gastric inhibitory polypeptide, gastrin, ghrelin, glucagon, glucagon-like peptide-1, gonadotropin-releasing hormone, growth hormone-releasing hormone, hepcidin, human chorionic gonadotropin, human placental lactogen, growth hormone, inhibin, insulin, insulin-like growth factor (or somatomedin), leptin, lipotropin, luteinizing hormone, melanocyte stimulating hormone, motilin, orexin, osteocalcin, oxytocin, pancreatic polypeptide, parathyroid hormone, pituitary adenylate cyclase-activating peptide, prolactin, prolactin releasing hormone, relaxin, renin, secretin, somatostatin, thrombopoietin, thyroid-stimulating hormone (or thyrotropin), thyrotropin-releasing hormone, vasoactive intestinal peptide, guanylin, uroguanylin, testosterone, dehydroepiandrosterone, androstenedione, dihydrotestosterone, aldosterone, estradiol, estrone, estriol, cortisol, progesterone, and calcitriol (1,25-dihydroxyvitamin D3).

In some embodiments, the analyte is a natural, synthetic, or recombinant immunoglobulin antibody (including a natural, synthetic, or recombinant antibody, or a portion thereof), an antibody fragment, or a derivative thereof. In some embodiments, the analyte is selected from any of the following: IgA, IgD, IgE, IgG, IgM, IgY, IgW, Vh, Vhh, a DARPin, a single-chain variable fragment (scFv), a monobody, a diabody, or a portion thereof.

In some embodiments, the analyte includes or consists of DNA or RNA, such as a polynucleotide formed from DNA, RNA, or a combination of DNA and RNA.

In some embodiments, the analyte is a biological product or biosimilar. In some embodiments, the analyte is selected from any of the following: abatacept, abciximab, abobotulinumtoxinA, adalimumab, adalimumab-atto, ado-trastuzumab emtansine, aflibercept, agalsidase beta, albiglutide, aldesleukin, alemtuzumab, alglucosidase alfa, alglucosidase alfa, alirocumab, alteplase, cathflo activase, anakinra, asfotase alfa, asparaginase, asparaginase *Erwinia chrysanthemi*, atezolizumab, basiliximab, becaplermin, belatacept, belimumab, bevacizumab, bezlotoxumab, blinatumomab, brentuximab vedotin, canakinumab, capromab pendetide, certolizumab pegol, cetuximab, collagenase, collagenase *clostridium histolyticum*, daclizumab, daclizumab, daratumumab, darbepoetin alfa, denileukin diftitox, denosumab, dinutuximab, dornase alfa, dulaglutide, ecallantide, eculizumab, elosulfase alfa, elotuzumab, Empliciti, epoetin alfa, etanercept, etanercept-szzs, evolocumab, filgrastim, filgrastim-sndz, galsulfase, glucarpidase, golimumab, ibritumomab tiuxetan, idarucizumab, idursulfase, incobotulinumtoxinA, infliximab, infliximab-dyyb, interferon alfa-2b, interferon alfa-n3, interferon beta-1a, interferon beta-1b, interferon beta-1, interferon gamma-1b, ipilimumab, ixekizumab, laronidase, mepolizumab, methoxy polyethylene glycol-epoetin beta, metreleptin, natalizumab, necitumumab, nivolumab, obiltoxaximab, obinutuzumab, ocriplasmin, ofatumumab, olaratumab, omalizumab, onabotulinumtoxinA, oprelvekin, palifermin, palivizumab, panitumumab, parathyroid hormone, pegaspargase, pegfilgrastim, peginterferon alfa-2a, peginterferon alfa-2b, peginterferon beta-1a, pegloticase, pembrolizumab, pertuzumab, ramucirumab, ranibizumab, rasburicase, raxibacumab, reslizumab, reteplase, rilonacept, rimabotulinumtoxinB, rituximab, romiplostim, sargramostim, sebelipase alfa, secukinumab, siltuximab, tbo-filgrastim, tenecteplase, tocilizumab, tocilizumab, trastuzumab, ustekinumab, vedolizumab, or ziv-aflibercept.

In some embodiments, the analyte is a therapeutic monoclonal antibody. For example, in some embodiments, the analyte is selected from any of the following monoclonal antibodies: abciximab (e.g., ReoPro), a chimeric antibody that targets and inhibits glycoprotein IIb/IIIa, and is used for the treatment of cardiovascular disease; adalimumab (e.g., Humira), a human antibody that inhibits tumor necrosis factor alpha (TNF-α) signaling, and is used for the treatment of rheumatoid arthritis, psoriatic arthritis, ankylosing spondylitis, Crohn's disease, ulcerative colitis, chronic psoriasis, hidradenitis suppurativa, and juvenile idiopathic arthritis; alemtuzumab (e.g., Campath), a humanized antibody that targets CD52, and is used for the treatment of chronic lymphocytic leukemia; basiliximab (e.g., Simulect), a chimeric antibody that targets the interleukin-2 receptor alpha chain (CD25), and is used for the treatment of transplant rejection; belimumab (e.g., Benlysta), a human antibody that targets and inhibits B-cell activating factor, and is used for the treatment of systemic lupus erythematosus; bevacizumab (e.g., Avastin), a humanized antibody that targets vascular endothelial growth factor (VEGF), and is used for the treatment of colorectal cancer, certain lung cancers, renal cancers, ovarian cancers, glioblastoma multiforme of the brain, and age related macular degeneration (off-label); brentuximab vedotin (e.g., Adcetris), a chimeric antibody that targets CD30, and is used for the treatment of anaplastic large cell lymphoma (ALCL) and Hodgkin lymphoma; canakinumab (e.g., llaris), a human antibody that targets interleukin 1β (IL-1β), and is used for the treatment of cryopyrin-associated periodic syndrome (CAPS); cetuximab (e.g., Erbitux), a chimeric antibody that targets epidermal growth factor receptor (EGFR), and is used for the treatment of colorectal cancer and head and neck cancer; certolizumab pegol (e.g., Cimzia), a humanized antibody that targets and inhibits TNF-α signaling, and is used for the treatment of Crohn's disease; daclizumab (e.g., Zenapax), a humanized antibody that targets interleukin-2 receptor alpha chain (CD25), and is used for the treatment of transplant rejection; daratumumab (e.g., Darzalex), a human antibody that targets CD38, and is used for the treatment of multiple myeloma; denosumab (e.g., Prolia and Xgeva), a human antibody that targets RANK ligand inhibitor, and is used for the treatment of postmenopausal osteoporosis and solid tumor bony metastases; eculizumab (e.g., Soliris), a humanized antibody that targets complement system protein C5, and is used for the treatment of paroxysmal nocturnal hemoglobinuria; efalizumab (e.g., Raptiva), a humanized antibody that targets CD11a, and is used for the treatment of psoriasis; golimumab (e.g., Simponi), a human antibody that targets TNF-α inhibitor, and is used for the treatment of rheumatoid arthritis, psoriatic arthritis and ankylosing spondylitis; ibritumomab tiuxetan (e.g., Zevalin), a murine antibody that targets CD20, and is used for the treatment of non-Hodgkin lymphoma (in combination with yttrium-90 or indium-111); infliximab (e.g., Remicade), a chimeric antibody that targets and inhibits TNF-α signaling, and is used for the treatment of Crohn's disease, ulcerative colitis, psoriasis, psoriatic arthritis, ankylosing spondylitis and rheumatoid arthritis; ipilimumab (MDX-101) (e.g., Yervoy), a human antibody that targets and blocks CTLA-4, and is used for the treatment of melanoma; muromonab-CD3 (e.g., Orthoclone OKT3), a murine antibody that targets T cell CD3 receptor, and is used for the treatment of transplant rejection; natalizumab (e.g., Tysabri), a humanized antibody that targets alpha-4 integrin, and is used for the treatment of multiple sclerosis and Crohn's disease; nivolumab (e.g., Opdivo), a human antibody that targets and blocks programmed cell death protein 1 (PD-1), and is used for the treatment of melanoma and squamous-cell carcinoma of the lung; ofatumumab (e.g., Arzerra), a human antibody that targets CD20, and is used for the treatment of chronic lymphocytic leukemia; omalizumab (e.g., Xolair), a humanized antibody that targets immunoglobulin E (IgE), and is used for the treatment of mainly allergy-related asthma; palivizumab (e.g., Synagis), a humanized antibody that targets an epitope of the RSV F-protein, and is used for the treatment of respiratory syncytial virus; panitumumab (e.g., Vectibix), a human antibody that targets epidermal growth factor receptor (EGFR), and is used for the treatment of colorectal cancer; pembrolizumab (e.g., Keytruda), a humanized antibody that targets the programmed cell death 1 (PD-1) receptor, and is used for the treatment of melanoma and non-small cell lung cancer; ranibizumab (e.g., Lucentis), a humanized antibody that targets vascular endothelial growth factor A (VEGF-A), and is used for the treatment of macular degeneration; rituximab (e.g., Rituxan and Mabthera), a chimeric antibody that targets CD20, and is used for the treatment of non-Hodgkin lymphoma; tocilizumab or atlizumab (e.g., Actemra or RoActemra), a humanized antibody that targets interleukin 6 receptor (IL-6R), and is used for the treatment of rheumatoid arthritis and systemic juvenile idiopathic arthritis; tositumomab (e.g., Bexxar), a murine antibody that targets CD20, and is used for the treatment of non-Hodgkin lymphoma; trastuzumab (e.g., Herceptin), a humanized antibody that targets receptor tyrosine-protein kinase erbB-2 (ErbB2) or CD340, and is used for the treatment of breast cancer; ustekinumab (e.g., Stelara), a human antibody that targets interleukin 12 (IL-12) and interleukin 23 (IL-23), and is used for the treatment of psoriatic arthritis and plaque psoriasis; and vedolizumab (e.g., Entyvio), a humanized antibody that targets integrin a437, and is used for the treatment of Crohn's disease and ulcerative colitis.

In some embodiments, the analyte may be a cell surface protein or biomolecule, or be bound to a membrane of a cell. For example, in some embodiments, the analyte is a cell-surface marker and/or a cell-surface receptor. In some embodiments, the analyte is selected from any of the following: adrenergic receptor, olfactory receptors, receptor tyrosine kinases, epidermal growth factor receptor, insulin receptor, fibroblast growth factor receptors, high affinity neurotrophin receptors, ephrin receptors, integrins, low affinity nerve growth factor receptor, NMDA receptor, or immune receptors. In some embodiments, the analyte is HER2, a portion of HER2, or a multimeric protein complex that includes HER2. In some embodiments, the detected HER2 is obtained from serum.

In some embodiments, the analyte is a viral or bacterial protein, DNA, or RNA. Stated differently, in some embodiments, the analyte is DNA, RNA, or a protein from a virus or a bacterium, such as a pathogenic virus or bacterium. Exemplary viruses and bacteria for the analyte can be selected from any of the following: astrovirus, chickenpox, dengue virus, Ebola, foot-and-mouth disease virus, hepatitis A, hepatitis B, hepatitis C, herpes, human immunodeficiency virus, human papillomavirus, influenza, Japanese encephalitis, measles, mumps, Naples virus, parvovirus, rabies, rubella, shingles, smallpox, Toscana virus, Varicella Zoster virus, West Nile virus, yellow fever, *Zika* virus, *Bacillus anthracis, Bacillus cereus, Bartonella henselae, Bartonella quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli, Francisella tularensis, Haemophilus influenzae, Helicobacter pylori, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcer-* ans, *Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Ureaplasma urealyticum, Vibrio cholerae, Yersinia pestis, Yersinia enterocolitica,* and *Yersinia pseudotuberculosis.*

In some embodiments, the analyte is a complex formed from protein interaction partners. Any suitable set of protein interaction partners may be used as an analyte. In some embodiments, an analyte may be a cell surface or membrane-bound complex, such as the EGFR-HER2 complex, the HER2-HER2 homodimer, or the HER2-HER3 heterodimer. In other embodiments, the analyte is a soluble complex, such as the P53-MDM2 complex, VEGF dimer, BAK-BclxL complex, or the XIAP-Smac complex.

As noted above, in some embodiments, the analyte is a modified protein. The modification to the protein may be any suitable modification (e.g., a post-translation modification). In some embodiments, the modification is a naturally occurring modification. In some embodiments, the modification is indicative of a normal state or a disease state. In some embodiments, the modification is a synthetic modification, such as a protein that has been modified to improve pharmacokinetics, improve efficacy, and/or to reduce toxicity. Exemplary post-translational modifications include phosphorylation, glycosylation, lipidation, or acylation. In some embodiments, the modified protein is a pegylated protein, such as, for example, pegadamase, pegaspargase, peginterferon-2b, peginterferon-2a, pegfilgrastim, pegvisomant, pegaptanib, mPEG-epoetin, certolizumab, PEG-uricase. In some embodiments, the protein is modified after removal from a cellular environment. Such modification can improve pharmacokinetics, enhance efficacy, and/or decrease toxicity of the modified protein. In some embodiments, the analyte is an antibody-drug conjugate. In some embodiments, the analyte is an antibody-enzyme conjugate. In some embodiments, the analyte is a fusion protein.

In some embodiments, the analyte is an autoantibody. In such embodiments, the analyte may be an autoantibody that recognizes and binds a self-antigen. In some embodiments, the analyte is selected from any of the following: antinuclear antibodies including anti-SSA/Ro autoantibodies, anti-La/SS-B autoantibodies, anti-centromere antibodies, anti-double-stranded DNA (dsDNA) antibodies, anti-Jo1 antibodies or anti-histidine-tRNA ligase antibodies, anti-ribonucleoprotein (RNP) antibodies, anti-snRNP core proteins antibodies or anti-Smith antibodies, anti-topoisomerase antibodies, anti-histone antibodies, anti-nucleoporin 62 antibodies or anti-p62 antibodies, anti-sp 100 or anti-sp 100 nuclear antigen antibodies, anti-nucleoporin 210 kDA antibodies or anti-glycoporin-210 antibodies, anti-transglutaminase antibodies including anti-tTG antibodies and anti-eTG antibodies, anti-ganglioside antibodies including anti-ganglioside GQ1B antibodies, anti-ganglioside GD3 antibodies, and anti-ganglioside GM1 antibodies, anti-actin antibodies, anti-cyclic citrulllinated peptide antibodies, anti-liver kidney microsomal type 1 antibodies, anti-lupus anticoagulant antibodies, anti-thrombin antibodies, anti-phospholipid antibodies, anti-neutrophil antibodies including anti-c-ANCA antibodies and anti-p-ANCA antibodies, anti-rheumatoid factor antibodies, anti-smooth muscle antibodies, anti-mitochondrial antibodies, anti-signal recognition particle (SRP) antibodies, anti-nicotinic acetylcholine receptor (AChR) antibodies, anti-muscle-specific kinase (MUSK) antibodies, anti-voltage-gated calcium channel (VGCC) antibodies including anti-P/Q-type voltage-gated calcium channel antibodies, anti-thyroid antibodies including anti-thyroid peroxidase (TPO) antibodies, anti-thyroglobulin antibodies (TgAbs), and anti-thyrotropin receptor antibodies (TRAbs), anti-Hu (ANNA-1) antibodies, anti-Yo antibodies, anti-Ma antibodies, anti-Ri (ANNA-2) antibodies, anti-Tr antibodies, anti-amphyiphysin antibodies, anti-glutamate decarboxylase (GAD) antibodies, anti-voltage-gated potassium channel (VGKC) antibodies, anti-collapsin response mediator protein 5 (CRMP-5) antibodies, anti-N-methyl-D-aspartate receptor (NMDAr) antibodies, and anti-aquaporin or anti-NMO antibodies. In some embodiments, the autoantibody binds to an acetylcholine receptor (e.g., a nicotinic acetylcholine receptor).

In some embodiments, when a particular autoantibody is known to interact with a particular self-antigen target to cause an autoimmune disease or disorder, the disclosed methods may be used to diagnose or confirm that a patient has, or is at risk of developing, a particular form of autoimmune disease or autoimmune-associated disease.

For example, when a patient is suspected of having systemic lupus erythematosus (SLE), the underlying cause of that SLE may be confirmed and/or attributed to the presence of anti-SSA/Ro autoantibodies, anti-double-stranded DNA (dsDNA) antibodies, anti-histone antibodies, anti-snRNP core proteins antibodies or anti-Smith antibodies and/or anti-lupus anticoagulant antibodies or anti-thrombin autoantibodies by the methods described herein.

When a patient is suspected of having neonatal heart block, the underlying cause may be confirmed and/or attributed to the presence of anti-SSA/Ro autoantibodies by the methods described herein.

When a patient is suspected of having primary Sjögren's syndrome the underlying cause of the syndrome may be confirmed and/or attributed to the presence of anti-SSA/Ro autoantibodies or anti-La/SS-B autoantibodies by the methods described herein.

When a patient is suspected of having CREST syndrome the underlying cause of the syndrome may be confirmed and/or attributed to the presence of anti-centromere antibodies by the methods described herein.

When a patient is suspected of having inflammatory myopathy, the underlying cause may be confirmed and/or attributed to the presence of anti-Jo1 antibodies or anti-histidine-tRNA ligase autoantibodies by the methods described herein.

When a patient is suspected of having mixed connective tissue disease, the underlying cause may be confirmed and/or attributed to the presence of anti-ribonucleoprotein or anti-RNP autoantibodies by the methods described herein.

When a patient is suspected of having systemic sclerosis, the underlying cause of the disease may be confirmed and/or attributed to the presence of anti-Scl-70 antibodies or anti-type I topoisomerase antibodies by the methods described herein.

When a patient is suspected of having primary biliary cirrhosis, the underlying cause of the disease may be confirmed and/or attributed to the presence of anti-nucleoporin 62 antibodies or anti-p62 antibodies, anti-sp100 or anti-sp100 nuclear antigen antibodies, anti-nucleoporin 210 kDA antibodies or anti-glycoporin-210 antibodies by the methods described herein.

When a patient is suspected of having celiac disease, the underlying cause of the disease may be confirmed and/or attributed to the presence of anti-transglutaminase (tTG) antibodies by the methods described herein.

When a patient is suspected of having dermatitis herpetiformis, the underlying cause of the disease may be confirmed and/or attributed to the presence of anti-transglutaminase (eTG) antibodies by the methods described herein.

When a patient is suspected of having Miller-Fisher syndrome the underlying cause of the syndrome may be confirmed and/or attributed to the presence of anti-ganglioside GQ1B antibodies by the methods described herein.

When a patient is suspected of having acute motor axonal neuropathy (AMAN) the underlying cause of the disease may be confirmed and/or attributed to the presence of anti-ganglioside GD3 antibodies by the methods described herein.

When a patient is suspected of having multifocal motor neuropathy with conduction block (MMN) the underlying cause of the disease may be confirmed and/or attributed to the presence of anti-ganglioside GM1 antibodies by the methods described herein.

When a patient is suspected of having rheumatoid arthritis the underlying cause of the disease may be confirmed and/or attributed to the presence of anti-cyclic citrullinated peptide (CCP), or anti-rheumatoid factor antibodies by the methods described herein.

When a patient is suspected of having autoimmune hepatitis, or chronic autoimmune hepatitis, the underlying cause of the disease may be confirmed and/or attributed to the presence of anti-liver kidney microsomal type 1 antibodies or anti-smooth muscle antibodies by the methods described herein.

When a patient is suspected of having antiphospholipid syndrome the underlying cause of the syndrome may be confirmed and/or attributed to the presence of anti-phospholipid antibodies by the methods described herein.

When a patient is suspected of having granulomatosis with polyangiitis the underlying cause of the disease may be confirmed and/or attributed to the presence of anti-neutrophil cytoplasmic (c-ANCA) antibodies by the methods described herein.

When a patient is suspected of having microscopic polyangiitis, eosinophilic granulaomatosis with polyangiitis, or systemic vasculitides, the underlying cause of the disease may be confirmed and/or attributed to the presence of anti-neutrophil perinuclear (p-ANCA) antibodies by the methods described herein.

When a patient is suspected of having primary biliary cirrhosis the underlying cause may be confirmed and/or attributed to the presence of anti-mitochondrial antibodies by the methods described herein.

When a patient is suspected of having polymyositis the underlying cause may be confirmed and/or attributed to the presence of anti-signal recognition particle (SRP) antibodies by the methods described herein.

When a patient is suspected of having scleromyositis the underlying cause may be confirmed and/or attributed to the presence of anti-exosome complex antibodies by the methods described herein.

When a patient is suspected of having myasthenia gravis the underlying cause may be confirmed and/or attributed to the presence of anti-acetylcholine receptor (anti-AChr), or anti-muscle-specific kinase (MUSK) antibodies by the methods described herein.

When a patient is suspected of having Lambert-Eaton myasthenic syndrome the underlying cause of the syndrome may be confirmed and/or attributed to the presence of anti-voltage-gated calcium channel (P/Q-type) (VGCC) antibodies by the methods described herein.

When a patient is suspected of having Hashimoto's thyroiditis or Graves' disease the underlying cause may be confirmed and/or attributed to the presence of anti-thyroid peroxidase (TPO) antibodies, anti-thyroglobulin antibodies (TgAbs), or anti-thyrotropin receptor antibodies (TRAbs) by the methods described herein.

When a patient is suspected of having paraneoplastic cerebellar degeneration, limbic encephalitis, encephalomyelitis, subacute sensory neuronopathy, or choreathetosis, the underlying cause of the disease may be confirmed and/or attributed to the presence of anti-Hu (ANNA-1) autoantibodies, anti-Yo autoantibodies, or anti-amphiphysin antibodies by the methods described herein.

When a patient is suspected of having opsoclonus myoclonus syndrome the underlying cause of the syndrome may be confirmed and/or attributed to the presence of anti-Ri (ANNA-2) antibodies by the methods described herein.

When a patient is suspected of having paraneoplastic cerebellar syndrome the underlying cause of the syndrome may be confirmed and/or attributed to the presence of anti-Tr or anti-glutamate receptor autoantibodies by the methods described herein.

When a patient is suspected of having stiff person syndrome the underlying cause of the syndrome may be confirmed and/or attributed to the presence of anti-amphiphysin or anti-glutamate decarboxylase (anti-GAD) autoantibodies by the methods described herein.

When a patient is suspected of having Isaac's syndrome (autoimmune neuromyotonia) or limbic encephalitis the underlying cause may be confirmed and/or attributed to the presence of anti-voltage-gated potassium channel (anti-VGKC) autoantibodies by the methods described herein.

When a patient is suspected of having optic neuropathy or chorea the underlying cause may be confirmed and/or attributed to the presence of anti-collapsin response mediator protein 5 (anti-CRMP-5) autoantibodies by the methods described herein.

When a patient is suspected of having Sydenham's chorea or pediatric autoimmune neuropsychiatric disease associated with *Streptococcus* (PANDAS), the underlying cause may be confirmed and/or attributed to the presence of anti-basal ganglial neuron autoantibodies by the methods described herein.

When a patient is suspected of having anti-N-methyl-D-aspartate (NDMA) receptor encephalitis the underlying cause may be confirmed and/or attributed to the presence of anti-NDMAr autoantibodies by the methods described herein.

When a patient is suspected of having neuromyelitis optica (Devic's syndrome) the underlying cause may be confirmed and/or attributed to the presence of anti-aquaporin-4 autoantibodies or NMO antibodies by the methods described herein.

The specific examples described above to confirm the underlying cause of a given autoimmune disease or autoimmune-related disease are only exemplary. Indeed, the disclosed methods may be used to diagnose a wide range of known autoimmune or autoimmune-related diseases, including: Acute Disseminated Encephalomyelitis (ADEM), Acute necrotizing hemorrhagic c leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenia purpura (ATP), Autoimmune thyroid disease, Autoimmune urticarial, Axonal & neuronal neuropathies, Balo disease, Behcet's disease, Bullous pemphigoid, Cardiomyopathy, Castleman disease, Celiac disease, Chagas disease, Chronic fatigue syndrome-associated autoimmune diseases, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia-associated autoimmune diseases, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenia purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease (chronic), Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatic, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenia purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, and Wegener's granulomatosis (now termed Granulomatosis with Polyangiitis (GPA)).

In some embodiments, the affinity of the first and/or second targeting domains to the corresponding target regions may be greater than the affinity of the peptide fragments of the split protein to the remaining peptide fragment(s) of the split protein, thereby reducing background signal. In some embodiments the affinity of the first and/or second targeting domains to the corresponding target regions may be at least 1, 2, 3, and/or 4 orders of magnitude greater than the affinity of a peptide fragment of the split protein to the remaining peptide fragment(s) of the split protein complex. In some embodiments, the first targeting domain and the second targeting domain do not bind directly to each other. In other words, the first targeting domain and the second targeting domain may be brought near each other not through any direct interaction between the first targeting domain and the second targeting domain but through binding to the same analyte.

Related kits may be used to detect an analyte. In some embodiments, the kit includes a first vector. The first vector may include a first sequence that encodes a first peptide fragment of a tripartite split enzyme. The vector may be configured to facilitate insertion of a nucleotide sequence for a first targeting domain such that expression of the resulting vector yields a fusion protein that includes both the first targeting domain and the first peptide fragment.

In some embodiments, the kit may additionally or alternatively include a second vector. The second vector may include a second sequence that encodes a second peptide fragment of a tripartite split enzyme. The vector may be configured to facilitate insertion of a nucleotide sequence for a second targeting domain such that expression of the resulting vector yields a fusion protein that includes both the second targeting domain and the second peptide fragment.

In some embodiments, the kit may include a third fragment of the tripartite split enzyme. The third peptide fragment may have a mass of between 16 kDa and 17 kDa. In some embodiments, the third peptide fragment has at least 70%, 80%, 90%, 95%, or 100% sequence identity to the sequence of SEQ ID NO 3. In some embodiments, the third peptide fragment is between 140 and 150 amino acids. For example, in some embodiments, the third peptide is between 145 and 150 amino acids (e.g., 148 amino acids). In some embodiments, the kit may additionally or alternatively include a vector for expressing the third fragment of the tripartite split enzyme.

In other embodiments, a kit may include a first agent, a second agent, and a third agent, as defined above. The first agent may include a first targeting domain and a first peptide fragment of a split reporter protein. The second agent may include a second targeting domain and a second peptide fragment of the split reporter protein. The third agent may include a third fragment of the split reporter protein. In some such embodiments, the first and second targeting domains determine the antigen to be detected using the kit. Such a kit may optionally include the reagents necessary to generate a detectable signal when the first, second and third fragments of the split reporter protein are assembled into a functional reporter protein, such as a functional enzyme reporter. In such embodiments, the kit may optionally include the substrate for the assembled functional enzyme reporter, and instructions for use of the kit for detecting a specific antigen. In some embodiments of such kits, the specific analyte to be detected may be selected from any of the analytes disclosed herein. In some embodiments of such kits, the specific analyte to be detected may be selected from an antibody formed in response to an allergen, a bacterial infection, or a viral infection, a therapeutic antibody, or and autoantibody that binds a self-antigen.

Some embodiments within the scope of this disclosure may be detection reagents. Some detection reagents may include a targeting domain and a peptide fragment of a tripartite split reporter protein. The peptide fragment of the detection reagent may have a mass of less than 3 kDa. In some embodiments, the peptide fragment is 15, 14, 13, 12, 11, or 10 amino acids in length. In some embodiments, the peptide fragment has at least 80%, 90%, 95%, and/or 100% sequence identity to the sequence of SEQ ID NO 1. In other embodiments, the peptide fragment has at least 80%, 90%, 95%, and/or 100% sequence identity to the sequence of SEQ ID NO 2. The peptide fragment of a detection reagent may be capable of forming a complex with one or more other peptide fragments to form an intact split reporter protein.

Some embodiments may be nucleic acids. For example, some nucleic acids may include a sequence that includes a promoter, an insertion site, and a region that encodes a peptide fragment of a split reporter enzyme. The nucleic acid may be configured such that insertion of a sequence that encodes a targeting domain at the insertion site allows for expression of a fusion protein that includes the targeting domain and the peptide fragment. Stated differently, the sequence of the resulting nucleotide, which encodes a fusion protein, may be operably linked to a promoter.

Some embodiments include methods for detecting an analyte in a mixture (e.g., a mixture in a vessel). The method may include the step of delivering a plurality of agents into a mixture, wherein each of the agents includes a portion of a split reporter protein. For example, some methods may include the steps of delivering a first agent into the mixture, and delivering a second agent into the mixture. The first agent may include a first targeting domain and a first peptide fragment of the split reporter protein. The second agent may include a second targeting domain and a second peptide fragment of the split reporter protein. In some embodiments, the split reporter protein is a binary split reporter protein (i.e., the split reporter protein has only two fragments). In other embodiments (e.g., where the split reporter protein is a ternary split reporter protein), the method may further include the step of delivering a third agent into the mixture. The third agent may include or consist essentially of a third fragment of the split reporter protein. In some embodiments, the first agent and the second agent are delivered in substantially equimolar amounts (e.g., a ratio of 1:1 (+0.2)). In some embodiments, the first agent and the second agent are not delivered in substantially equimolar amounts. In some embodiments, the first agent and the second agent are delivered as purified proteins.

Upon delivery into the mixture, the first targeting domain of the first agent may bind to a first target region of the analyte. Similarly, the targeting domain of the second agent may bind to a second target region of the analyte. Such binding may increase the local concentration of these components. In embodiments that involve a binary split reporter protein, the first agent and the second agent may bind to one another to form an active complex. In embodiments that involve a ternary split reporter protein, the first agent and the second agent may bind (e.g., non-covalently) to a third agent to form an active complex. In both cases, the active complex is formed essentially only where the first agent and the second agent are in close proximity. These methods, in which binding of the individual peptide fragments to form an active complex is driven by the binding of targeting domains to an analyte, may be termed "target-binding activated complementation" or "target-engaged complementation."

In some embodiments, the first agent and the second agent are delivered to the mixture prior to delivery of the third agent. In other embodiments, the first agent, the second agent, and the third agent are simultaneously delivered to the mixture. Numerous different ordering of steps is possible, as will be understood by a skilled artisan having the benefit of this disclosure.

In some embodiments, the method further includes the step of delivering a substrate of the active complex into the mixture. Some methods may include the step of detecting light emitted from the mixture after the first agent, the second agent, and the third agent have been delivered to the mixture. The amount of light emitted from the mixture may be proportional to the amount of analyte that is contained therein. In some embodiments, the method is capable of detecting the analyte at concentrations of less than 5 pM, such as concentrations of less than 1 pM.

In some embodiments, the method is practiced outside of living cells. Stated differently, in some embodiments, the analyte to be detected is not disposed within a cell. In some embodiments, the analyte is detected in or from a cell lysate. In some embodiments, the method is carried out in a biological fluid. For example, some methods may be carried out in human serum or in a mixture that includes human serum. Other methods may be carried out in saliva or in a mixture that includes saliva. Other methods may be carried out in urine or in a mixture that includes urine. Detection of one or more analytes from other biological fluids is also contemplated.

In some embodiments, the method for detecting the analyte does not include a blocking step. Stated differently, in some embodiments, the method does not require delivery of a blocking agent, such as bovine serum albumin or milk proteins.

In some embodiments, the method for detecting the analyte does not include a wash step. Stated differently, in some embodiments, an unbound first agent and second agent need not be removed from the mixture prior to detection.

In some embodiments, the method for detecting the analyte does not involve immobilization of the analyte. In other words, in some embodiments, the analyte may be in solution (e.g., a homogeneous solution) when detected. In other embodiments, the analyte is immobilized onto a surface. In other embodiments, the analyte is present on the surface of a tissue or tissue sample (e.g., a prepared tissue sample mounted on a microscope slide).

In some embodiments, the method does not require the use of protein disulfide isomerase. Stated differently, in some methods, none of the first peptide fragment, the second peptide fragment, or the third peptide fragment contacts a protein disulfide isomerase.

FIG. 1 shows an embodiment of a split reporter system 100. The split reporter system 100 includes a first agent 110 and a second agent 120. The first agent 110 includes a first targeting domain 112 and a first peptide fragment 114 of a split reporter protein 101. The second agent 120 includes a second targeting domain 122 and a second peptide fragment 124 of the split reporter protein 101. Each targeting domain 112, 122 has an affinity to a particular target region 51, 52 of an analyte 50. In the depicted embodiment, the targeting domains are Fabs and the analyte 50 is a corresponding bivalent antigen.

When the first agent 110 and the second agent 120 are mixed with the antigen 50, the first targeting domain 112 of the first agent binds to a first epitope 51 of the antigen 50 and the second targeting domain 122 of the second agent 120 binds to the second epitope 52 of the antigen 50, thereby bringing the first peptide fragment 114 and the second peptide fragment 124 into close proximity. The close proximity of the first peptide fragment 114 to the second peptide fragment 124 leads to formation of an active reporter protein complex (i.e., intact split reporter protein 101). The active reporter protein complex can produce a detectable signal (e.g., fluorescence of luminescence). Thus, the signal produced by the active reporter protein complex may be used to detect the presence (and/or determine the quantity) of analyte 50 in a mixture.

Figure 2:
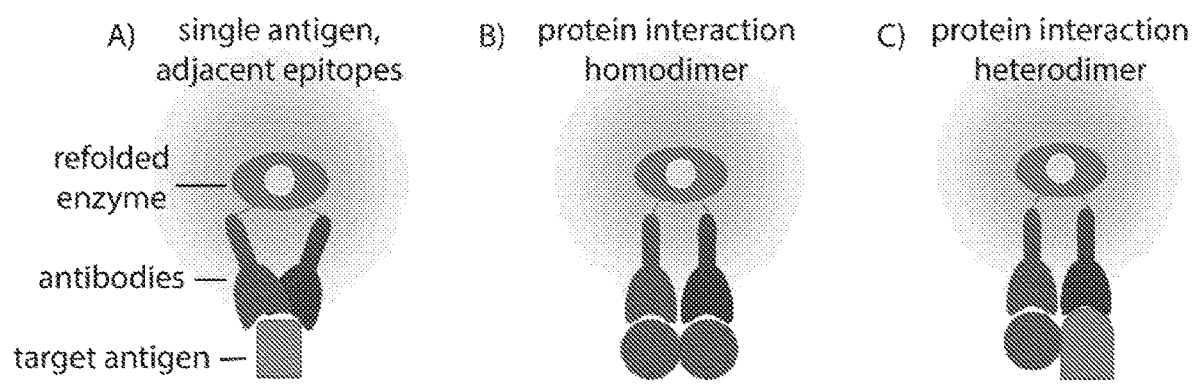
FIG. 2 is a schematic that shows alternative targeting modes for activating complementation in a split reporter system.

FIG. 2 is a schematic showing various targeting modes (FIGS. 2A-2C) for activating fragment complementation in a split reporter system. For example, FIG. 2A shows binding of targeting domains (e.g., antibodies) to adjacent target regions (e.g., epitopes) on a single bivalent analyte (e.g., antigen). FIG. 2B shows binding of targeting domains to identical target regions on separate proteins of a homomultimeric protein complex. And FIG. 2C shows binding of targeting domains to different proteins of a heteromultimeric protein complex. Any of the targeting modes shown in FIG. 2 may be used to detect an analyte.

Figure 3:
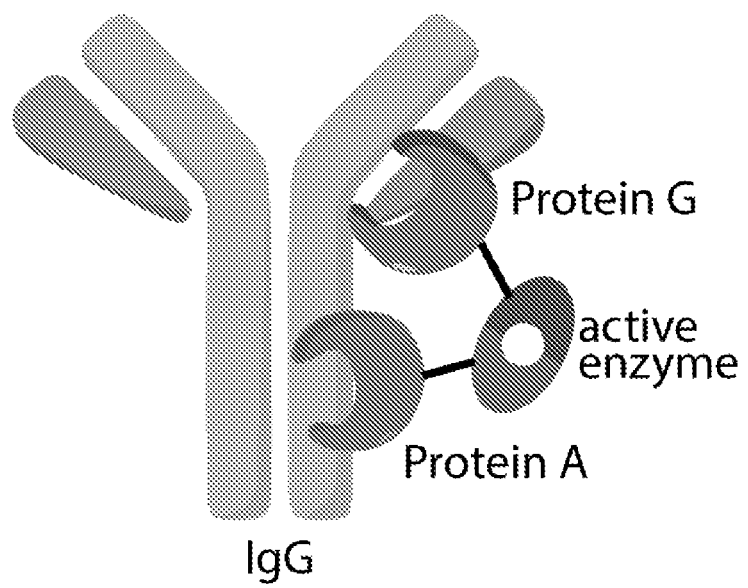
FIG. 3 is a schematic showing binding of fragment complementation components to an immunoglobulin antibody.

FIG. 3 is a schematic showing a fragment complementation system for detecting an antibody (e.g., IgG). In the depicted embodiment, a first agent includes (1) a first peptide fragment of a split reporter protein and (2) a first targeting domain (e.g., protein A) with affinity to a first target region of the antibody. The second agent includes (1) a second peptide fragment of a split reporter protein and (2) a second targeting domain (e.g., protein G) with affinity to a second target region of the antibody. When the first agent and the second agent are placed in a mixture that includes the antibody, the first agent and the second agent are drawn into proximity, which leads to formation of the split reporter protein complex.

Figure 4:
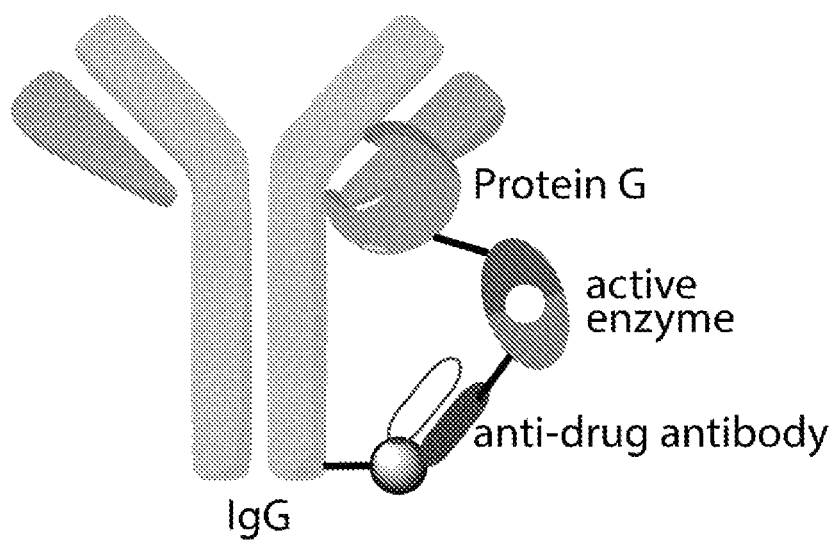
FIG. 4 is a schematic showing binding of fragment complementation components to a modified protein.

FIG. 4 is a schematic showing a fragment complementation system for detecting an antibody-drug conjugate. Such conjugates may be used, for example, to direct a drug to a particular location within a patient's body. In the depicted embodiment, the first agent includes a targeting domain with affinity to a drug that is attached to the antibody (e.g., via a linker), and the second agent includes a targeting domain (e.g., protein G) with affinity to a target region of the antibody. Such a fragment complementation system can be used to detect or quantify an antibody-drug conjugate in a mixture.

While the embodiments shown in FIGS. 1-4 are shown as two-component fragment complementation systems, a skilled artisan with the benefit of this disclosure will understand that analogous three-component fragment complementation systems are also within the scope of this disclosure.

Figure 5:
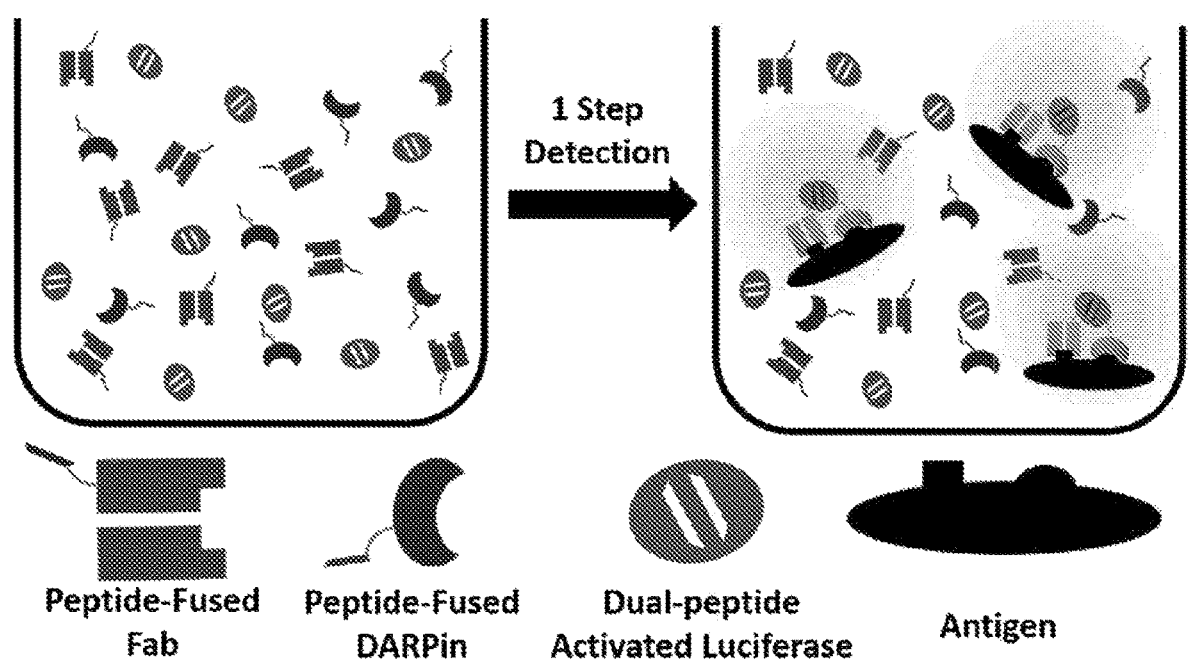
FIG. 5 is a schematic representation of a tripartite split reporter assay for detecting an analyte in a mixture.

FIG. 5 is a schematic showing detection of a single antigen via a tripartite fragment complementation system. More particularly, FIG. 5 shows a first agent that includes a first targeting domain (e.g., a Fab) and a first peptide fragment of a split reporter protein. The second agent includes a second targeting domain (e.g., a DARPin) and a second peptide fragment of a split reporter system. The embodiment shown in FIG. 5 also includes a third peptide fragment (i.e., a dual-peptide activated luciferase) of a split reporter system. When mixed in the presence of a bivalent antigen, the first agent and the second agent bind to different epitopes on the same bivalent antigen through their respective targeting domains. The first peptide fragment and the second peptide fragment may bind to the third peptide fragment to form an active split reporter protein complex (e.g., an active luciferase). In embodiments where the affinity of the first targeting domain and the second targeting domain to the antigen is significantly higher than the affinity of the components of the tripartite complex to each other, a signal generated from the activated complex (e.g., luminescence) may indicate the presence (or quantity) of antigen in a mixture. In some embodiments, one-step detection is possible. For example, an antigen may be added to a mixture that includes the three components of the tripartite fragment complementation system. The increase in signal from the activated complex may be used to detect and/or quantify the analyte.

Figure 6:
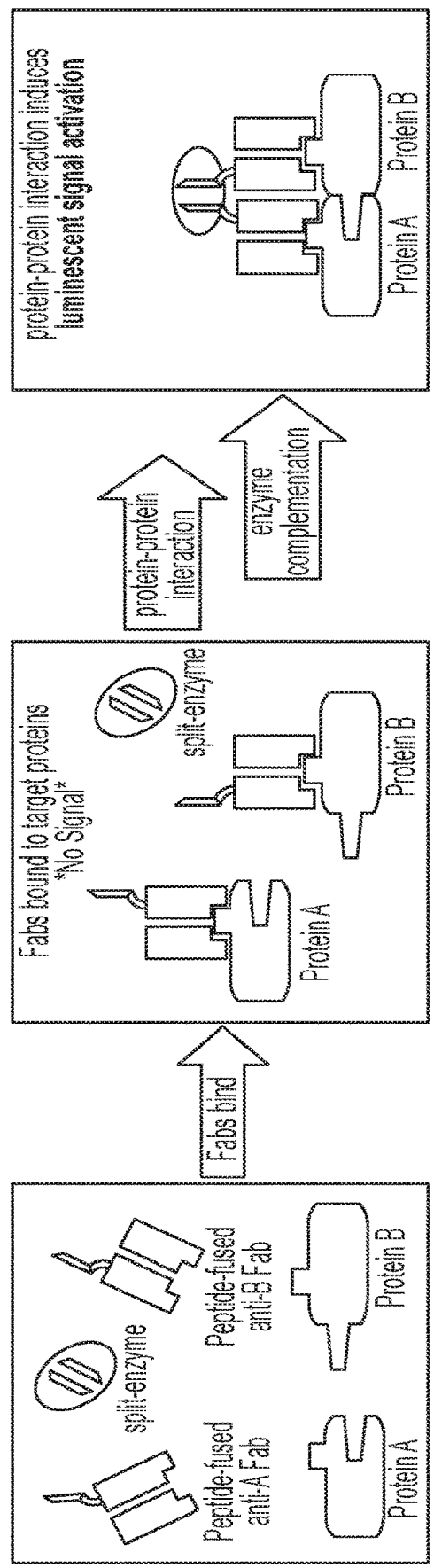
FIG. 6 is a schematic representation of a tripartite split reporter assay for detecting a molecular interaction.

FIG. 6 is a schematic that shows one embodiment for using a tripartite fragment complementation system to detect a protein-protein interaction. As shown in FIG. 6, the components of the fragment complementation system can be mixed with a pair of protein interaction partners. One agent of the fragment complementation system may bind to the first protein while a second agent of the fragment complementation system binds to a second protein. Upon (1) binding of the first protein to the second protein and (2) complementation with a third component of the fragment complementation system, an activated complex is formed, thereby allowing for detection of the interaction between the two proteins. In some embodiments, analogous detection can be accomplished where two proteins do not directly interact, but are in close proximity to one another.

Figure 7A:
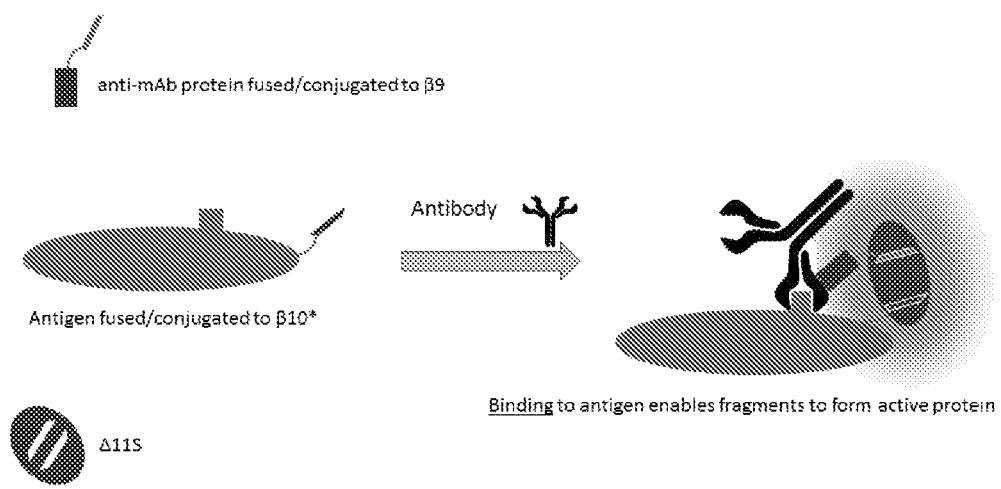
FIG. 7A is a schematic representation of a tripartite split reporter assay for detecting an antibody.
Figure 7B:
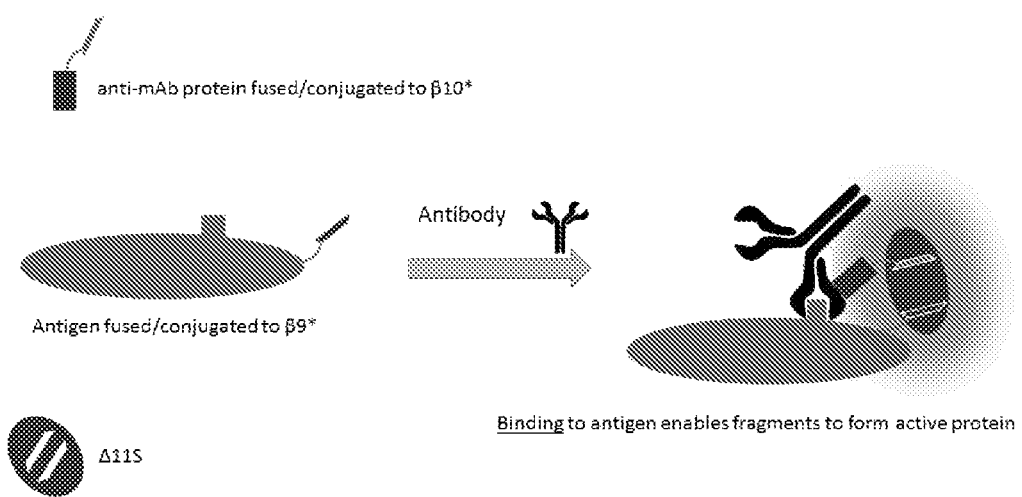
FIG. 7B is a schematic representation of a tripartite split reporter assay for detecting an antibody.

FIGS. 7A and 7B show alternative strategies for detection of an antibody (e.g., a therapeutic antibody or an autoantibody). In the schematics shown in FIGS. 7A and 7B, at least one component of the fragment complementation system is an agent that includes the corresponding antigen or epitope for the antibody. For example, in the depicted embodiments, a first agent includes a first peptide fragment and a first targeting domain that binds the antibody directly (e.g., an anti-mAb protein such as protein A, protein G, or protein L), while a second agent includes a second peptide fragment and a second targeting domain (e.g., the antigen or epitope to the targeted antibody). FIG. 7B differs from FIG. 7A in that, for FIG. 7A, the anti-mAb protein is fused or conjugated to β9 and the antigen is fused or conjugated to β10*. Conversely, in FIG. 7B, the anti-mAb protein is fused or conjugated to β10* while the antigen is fused or conjugated to β9. As shown in FIGS. 7A and 7B, binding of (1) the first targeting domain and the second targeting domain to the antibody and (2) the first peptide fragment and the second peptide fragment to a third fragment of the split reporter protein results in an active reporter protein complex, thereby allowing for detection of the antibody.

EXAMPLES

Recombinant Production of Split-Enzyme Reporter System Components

A tripartite split enzyme reporter system was engineered starting from NanoBiT®, a commercially available binary split enzyme reporter system for use in identifying protein-protein interactions. NanoBiT® includes an 11-amino acid peptide fragment (1.3 kDa) referred to as 114 and a 159-amino acid peptide fragment (18 kDa) referred to as 11S. The two fragments, when bound to one another, form a 10-stranded beta-barrel protein, with the 11S peptide fragment corresponding to the first nine beta stands of the protein, and 114 corresponding to the tenth beta strand.

Figure 8:
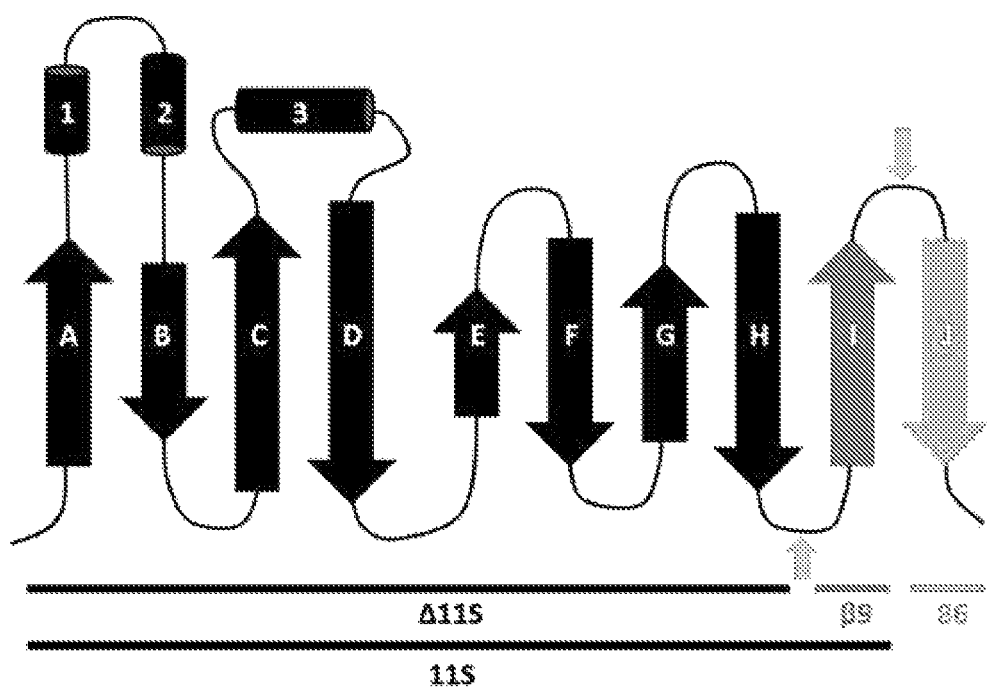
FIG. 8 is a topological representation of an engineered split luciferase. (β10* is sometimes referred to as "86" in the drawings.)

To develop the tripartite split enzyme, the 11S fragment was effectively split into two components: an 11-amino acid peptide (β9) corresponding to the most C-terminal amino acids of 11S, and a 148-amino acid peptide (A11S, 16.5 kDa) corresponding to the most N-terminal amino acids of 11S. Further, instead of using 114 (a relatively low affinity peptide, apparent $K_D$ of 190 M) for the remaining β10 peptide fragment, a peptide "β10*" (VSGWRLFKKIS) with higher affinity (apparent $K_D$ of ~700 nM) for the remaining portions of the complex was used. In short, the tripartite enzyme reporter system included (1) a relatively large N-terminal fragment (Δ11S) that includes the first eight beta strands of the intact complex, (2) a relatively short peptide fragment (β9) that corresponds with the ninth beta strand, and (3) another relatively short peptide fragment (β10*) that corresponds with the tenth beta strand. Topological representations of the peptide fragments are depicted in FIG. 8. (β10* is sometimes referred to as 86 in the drawings.)

To generate the fragments of the tripartite split enzyme system, Δ11S was produced recombinantly, while β9 and β10* were synthesized by solid-phase peptide synthesis.

Enzymatic Activity and Kinetics of Split Enzyme System

Figure 9:
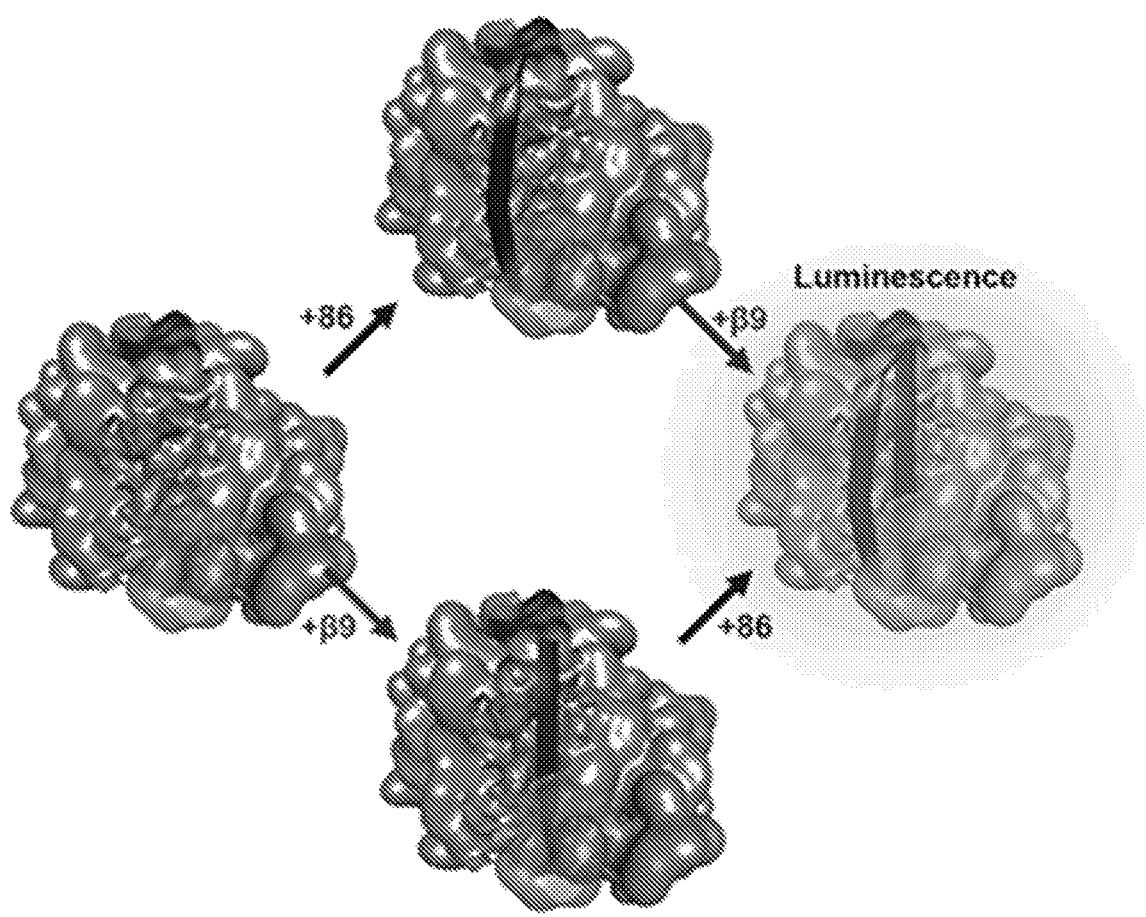
FIG. 9 is a structural model of different binding states for a tripartite split reporter protein.
Figure 10:
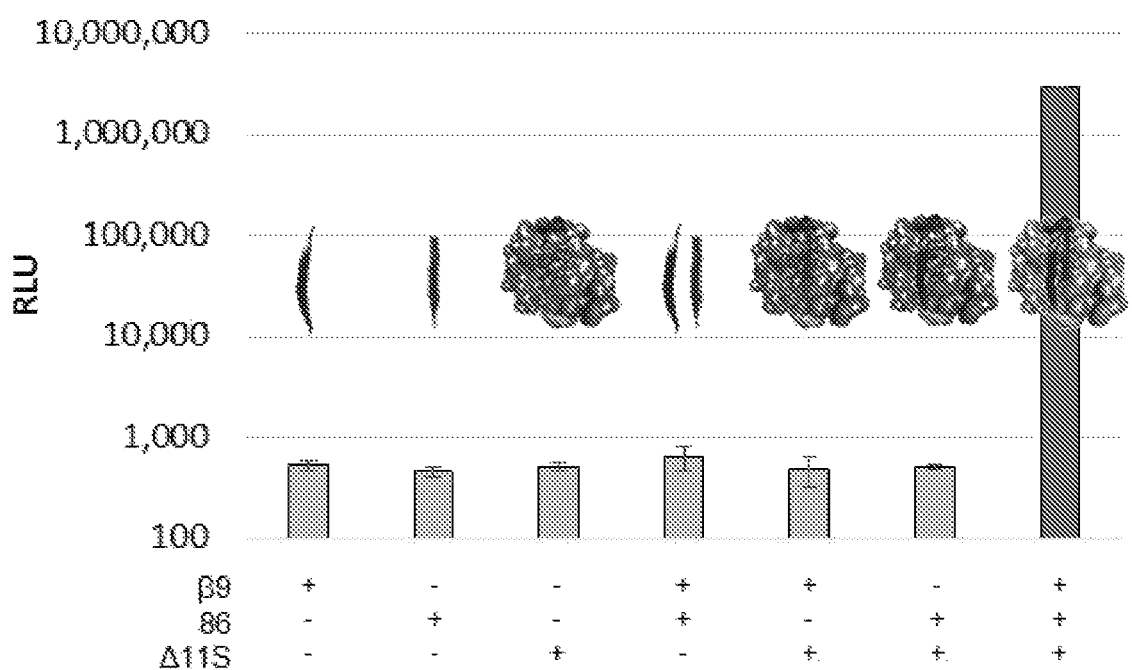
FIG. 10 is a bar graph showing luminescence of mixtures that have different components of a split reporter protein.

To confirm that the components of the reporter system were active only when all three peptide fragments were present as envisioned in the structural models shown in FIG. 9, the activity of various combinations of the peptide fragments (each at 1 μM concentration) was investigated in the presence of a substrate (furimazine). As shown in FIG. 10, the mixture of all three components is the only combination that produced significant luminescence. These findings confirmed that these fragments can be used to create a luminescent complementation system.

Figure 11:
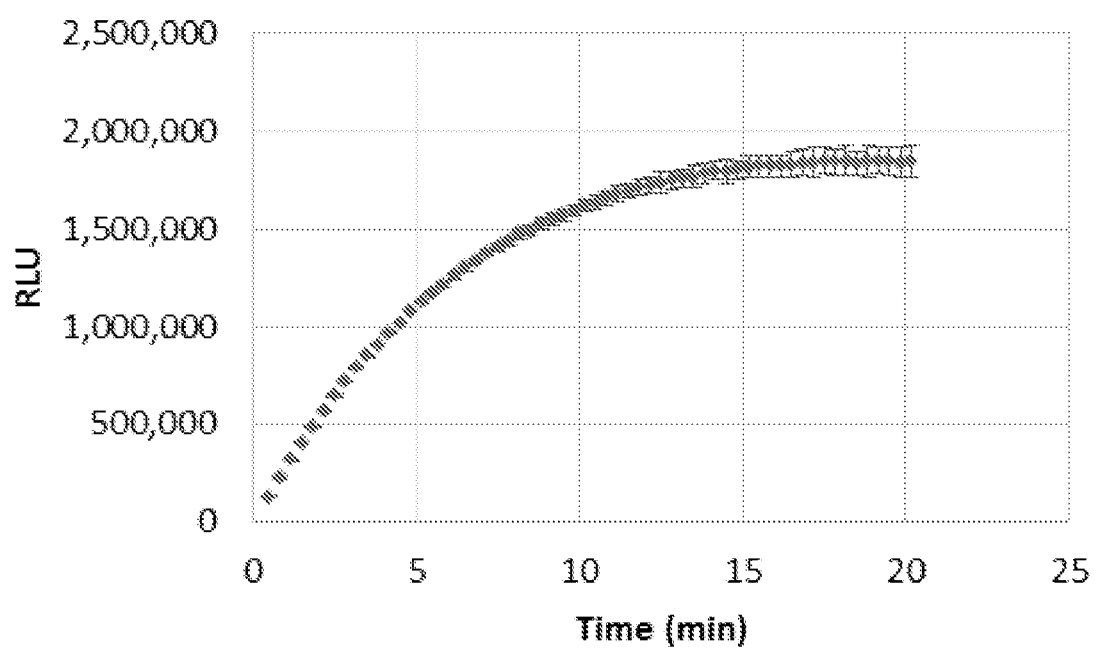
FIG. 11 is a scatterplot showing luminescence as a function of time for an analyte-detection assay.

Further, the luminescent signal was monitored after the addition of Δ11S (1 μM) into a solution that included both β9 and β10* (each at 1 μM). The results, as depicted in FIG. 11, show that, under the reaction conditions, 90% of the maximal signal was obtained within approximately 10 minutes, demonstrating that complex formation can be rapid.

Molecular Modeling and Screening to Identify Antibody Pairs for Target-Engaged Complementation in the Presence of HER2

Epidermal growth factor receptor 2 (HER2 or ErbB-2) was chosen for development and validation of a target-engaged complementation system. HER2 is a highly characterized biomarker (Kurebayashi, J., Breast Cancer 8, 45-51 (2001); Ross, J. S. et al. Mol Cell Proteomics 3, 379-98 (2004); Ross, J. S., et al., Oncologist 8, 307-25 (2003); Yu & Hung, Oncogene 19, 6115-21 (2000)) that has been the focus of significant research efforts stemming from its role in oncogenesis, including breast (Menard et al., J Cell Physiol 182, 150-62 (2000)), ovarian (Teplinsky & Muggia, Gynecol Oncol 135, 364-70 (2014); McAlpine et al., BMC Cancer 9, 433 (2009)), uterine (Santin et al., Clin Cancer Res 8, 1271-79 (2002); Todeschini et al., Br J Cancer 105, 1176-82 (2011)), gastric (Jorgensen, J. T., World J Gastroenterol 20, 4526-35 (2014); Hechtman & Polydorides, Arch Pathol Lab Med 136, 691-97 (2012)), and lung (Heinmoller et al., Clin Cancer Res 9, 5238-43 (2003)) cancers. HER2 expression levels can be used to diagnose and differentiate patients (Wesola & Jelen, Adv Clin Exp Med 24, 899-903 (2015)). Further, the extracellular domain of HER2 is often shed from cells, and its detection in serum can be used to monitor treatment and recurrence (Di Gioia et al., Clin Chim Acta 430, 86-91 (2014); Witzel et al., Breast Cancer Res Treat 123, 437-445 (2010); Esteva et al., Breast Cancer Res 7, R436-443 (2005)). Quantifying HER2 levels through targeted-engaged complementation can be simple and rapid, and may reduce the potential for error inherent to the multi-step protocols of typical immunoassays.

Figure 12:
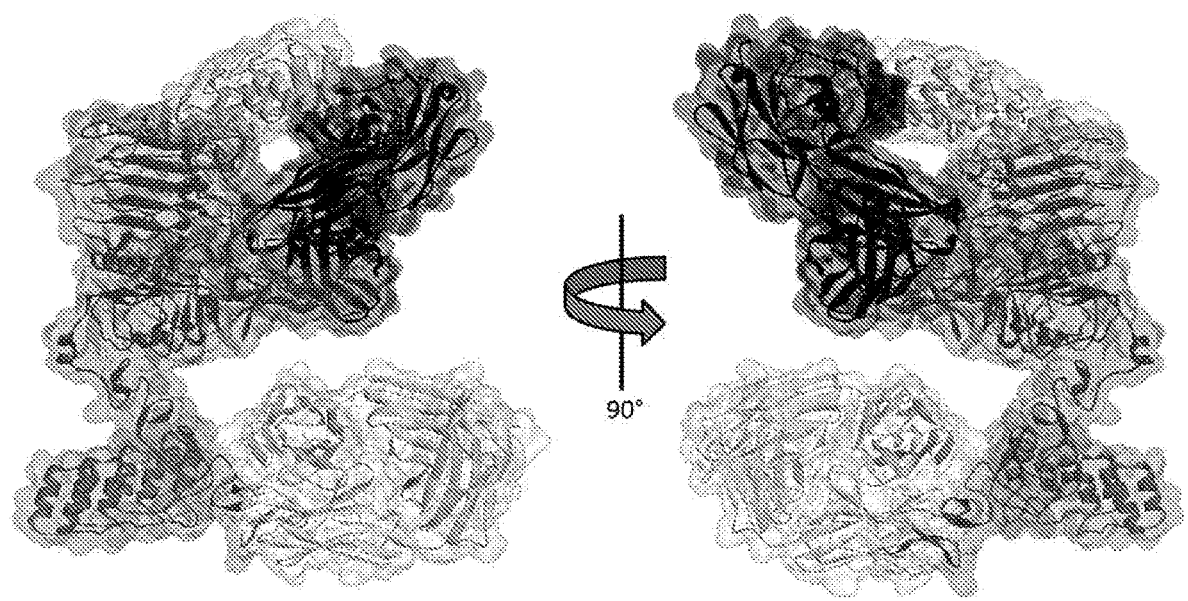
FIG. 12 is a molecular model of HER2 bound to various targeting domains.

Molecular modeling was used to identify proximal, but non-overlapping epitopes on HER2. More specifically, crystal structures in the Protein Data Bank of antibodies and other binders bound to HER2 were analyzed by superimposing the HER2 portion of the crystal structures (Trastuzumab, PDB ID: 1N8Z; Pertuzumab, PDB ID: 1S78; DARPin G3, PDB ID: 4HRN; and DARPin 9.29, PDB ID: 4HRL (see e.g., Cho et al., Nature 421, 756-60 (2003); Zhou et al., J Biol Chem 286, 31676-83 (2011); Fisher et al., J Mol Biol 402, 217-29 (2010); Eigenbrot et al., PNAS 107, 15039-44 (2010)). The superimposed structures are shown in FIG. 12. Four HER2 binders were selected based primarily on their non-competitive binding of HER2 (see FIG. 12). The selected binders included two antibodies (Trastuzumab and Pertuzumab) (Franklin et al., Cancer Cell 5, 317-28 (2004); Pegram et al., J Clin Oncol 16, 2659-71 (1998); Walshe et al., Clin Breast Cancer 6, 535-39 (2006); Plosker & Keam, Drugs 66, 449-75 (2006); Jost et al., Structure 21, 1979-91 (2013); Owen et al., J Control Release 172, 395-404 (2013); Lewis et al., Nat Biotechnol 32, 191-98 (2014); Epa et al., PLOS One 8, e59163 (2013); Zahnd et al., J Mol Biol 369, 1015-28 (2007); Carter et al., PNAS 89, 4285-89 (1992)) and two designed ankyrin repeated proteins (DARPins, G3 and 9.29). Both Trastuzumab and Pertuzumab are FDA-approved drugs for the treatment of HER2-positive breast cancer. As shown in FIG. 12, each of these binders binds to separate regions of the extracellular domain of HER2. While Trastuzumab binds domain IV close to the cell surface and does not interfere with HER2 oligomerization, Pertuzumab binds the protruding knob of domain II that is necessary for dimerization. Like Trastuzumab, DARPin G3 also binds domain IV, but binds the opposite side from the Trastuzumab binding site. DARPin 9.29 binds domain I adjacent to Pertuzumab, suggesting that these two binders would be suitable binding domains for a target-engaged complementation pair. All four of these proteins bind HER2 with high affinity ($K_D$ values between 0.09 nM and 3 nM), and do so on four distinct epitopes, suggesting that any two of them could yield a functional target-engaged complementation pair. As such, these binders were selected for screening. In addition to these binders that bind to characterized epitopes, an additional antibody that has not been crystallized but is known to not compete with Trastuzumab for binding—73J—was also screened.

To screen for functional target-engaged complementation pairs, constructs were designed in which each peptide fragment is fused to all five binders (either on the N- or C-terminus). For the antibodies, a fragment antigen binding fragment (Fab) was used, providing the opportunity to make a fusion at either of the light or heavy chain termini. Selecting one of each of the N- and C-termini produced a set of fusion protein fragments for screening (10 fusions with (9×10 fusions with β10* for a total of 100 possible pairs). For each of these fusions, a linker of 18 amino acids (SEQ ID NO 4) was used between the binder and the peptide. If fully extended, the linker is capable of spanning ~70 angstroms, suggesting that the termini of each binding pair should be within ~140 angstroms. As determined by molecular modeling, and shown in Table 1 (below), all pairs of termini are within this distance. (The measured distances ranged from 43-141 angstroms.)

TABLE 1

| Distance between potential binding pairs (angstroms) | | | | | | | | | | |
|---|---|---|---|---|---|---|---|---|---|---|
| | β9-LPert | PertH-β9 | β9-HTras | TrasH-β9 | β9-L73J | 73JH-β9 | β9-9.29 | 9.29-β9 | β9-G3 | G3-β9 |
| β10*-LPert | | | 47 | 43 | | | 67 | 56 | 97 | 66 |
| PertH-β10* | | | 92 | 93 | | | 69 | 52 | 141 | 121 |
| β10*-HTras | 47 | 92 | | | | | 93 | 100 | 47 | 55 |
| TrasH-β10* | 43 | 93 | | | | | 108 | 97 | 111 | 73 |
| β10*-L73J | | | | | | | | | | |
| 73JH-β10* | | | | | | | | | | |
| β10*-9.29 | 67 | 69 | 93 | 108 | | | | | 102 | 87 |
| 9.29-β10* | 56 | 52 | 100 | 97 | | | | | 132 | 104 |
| β10*-G3 | 97 | 141 | 47 | 111 | | | 102 | 132 | | |
| G3-β10* | 66 | 121 | 55 | 73 | | | 87 | 104 | | |

To identify functional target-engaged complementation pairs, all 20 fusions were expressed in *E. coli*. The SEQ ID numbers corresponding to nucleotide sequences and amino acid sequences for the fusion proteins are set forth in Table 2.

TABLE 2

| Sequence Listings | |
|---|---|
| β9-L73J | SEQ ID NO 5 (nucleotide) |
| | SEQ ID NO 6 (amino acid: β9-His Tag-light chain) |
| | SEQ ID NO 7 (amino acid: heavy chain) |
| β10*-L73J | SEQ ID NO 8 (nucleotide) |
| | SEQ ID NO 9 (amino acid: β10*-His Tag-light chain) |
| | SEQ ID NO 10 (amino acid: heavy chain) |
| 73JH-β9 | SEQ ID NO 11 (nucleotide) |
| | SEQ ID NO 12 (amino acid: light chain) |
| | SEQ ID NO 13 (amino acid: heavy chain-His Tag-β9) |
| 73JH-β10* | SEQ ID NO 14 (nucleotide) |
| | SEQ ID NO 15 (amino acid: light chain) |
| | SEQ ID NO 16 (amino acid: heavy chain-His Tag-β9) |
| β9-HTras | SEQ ID NO 17 (nucleotide) |
| | SEQ ID NO 18 (amino acid: light chain) |
| | SEQ ID NO 19 (amino acid: β9-His Tag-heavy chain) |
| β10*-HTras | SEQ ID NO 20 (nucleotide) |
| | SEQ ID NO 21 (amino acid: light chain) |
| | SEQ ID NO 22 (amino acid: β10*-His Tag-heavy chain) |
| TrasH-β9 | SEQ ID NO 23 (nucleotide) |
| | SEQ ID NO 24 (amino acid: light chain) |
| | SEQ ID NO 25 (amino acid: heavy chain-His Tag-β9) |
| TrasH-β10* | SEQ ID NO 26 (nucleotide) |
| | SEQ ID NO 27 (amino acid: light chain) |
| | SEQ ID NO 28 (amino acid: heavy chain-His Tag-β10*) |
| β9-LPert | SEQ ID NO 29 (nucleotide) |
| | SEQ ID NO 30 (amino acid: β9-His Tag-light chain) |
| | SEQ ID NO 31 (amino acid: heavy chain) |
| β10*-LPert | SEQ ID NO 32 (nucleotide) |
| | SEQ ID NO 33 (amino acid: β10*-His Tag-light chain) |
| | SEQ ID NO 34 (amino acid: heavy chain) |
| PertH-β9 | SEQ ID NO 35 (nucleotide) |
| | SEQ ID NO 36 (amino acid: light chain) |
| | SEQ ID NO 37 (amino acid: heavy chain- His Tag-β9) |
| PertH-β10* | SEQ ID NO 38 (nucleotide) |
| | SEQ ID NO 39 (amino acid: light chain) |
| | SEQ ID NO 40 (amino acid: heavy chain-His Tag-β10*) |
| β9-G3 | SEQ ID NO 41 (nucleotide) |
| | SEQ ID NO 42 (amino acid: β9-His Tag-G3) |
| β10*-G3 | SEQ ID NO 43 (nucleotide) |
| | SEQ ID NO 44 (amino acid: β10*-His Tag-G3) |
| G3-β9 | SEQ ID NO 45 (nucleotide) |
| | SEQ ID NO 46 (amino acid: His Tag-G3-β9) |
| G3-β10* | SEQ ID NO 47 (nucleotide) |
| | SEQ ID NO 48 (amino acid: His Tag-G3-β10*) |
| β9-9.29 | SEQ ID NO 49 (nucleotide) |
| | SEQ ID NO 50 (amino acid: β9-His Tag-9.29) |
| β10*-9.29 | SEQ ID NO 51 (nucleotide) |
| | SEQ ID NO 52 (amino acid: β10*-His Tag-9.29) |
| 9.29-β9 | SEQ ID NO 53 (nucleotide) |
| | SEQ ID NO 54 (amino acid: 9.29-His Tag-β9) |
| 9.29-β10* | SEQ ID NO 55 (nucleotide) |
| | SEQ ID NO 56 (amino acid: 9.29-His Tag-β10*) |

Figure 13:
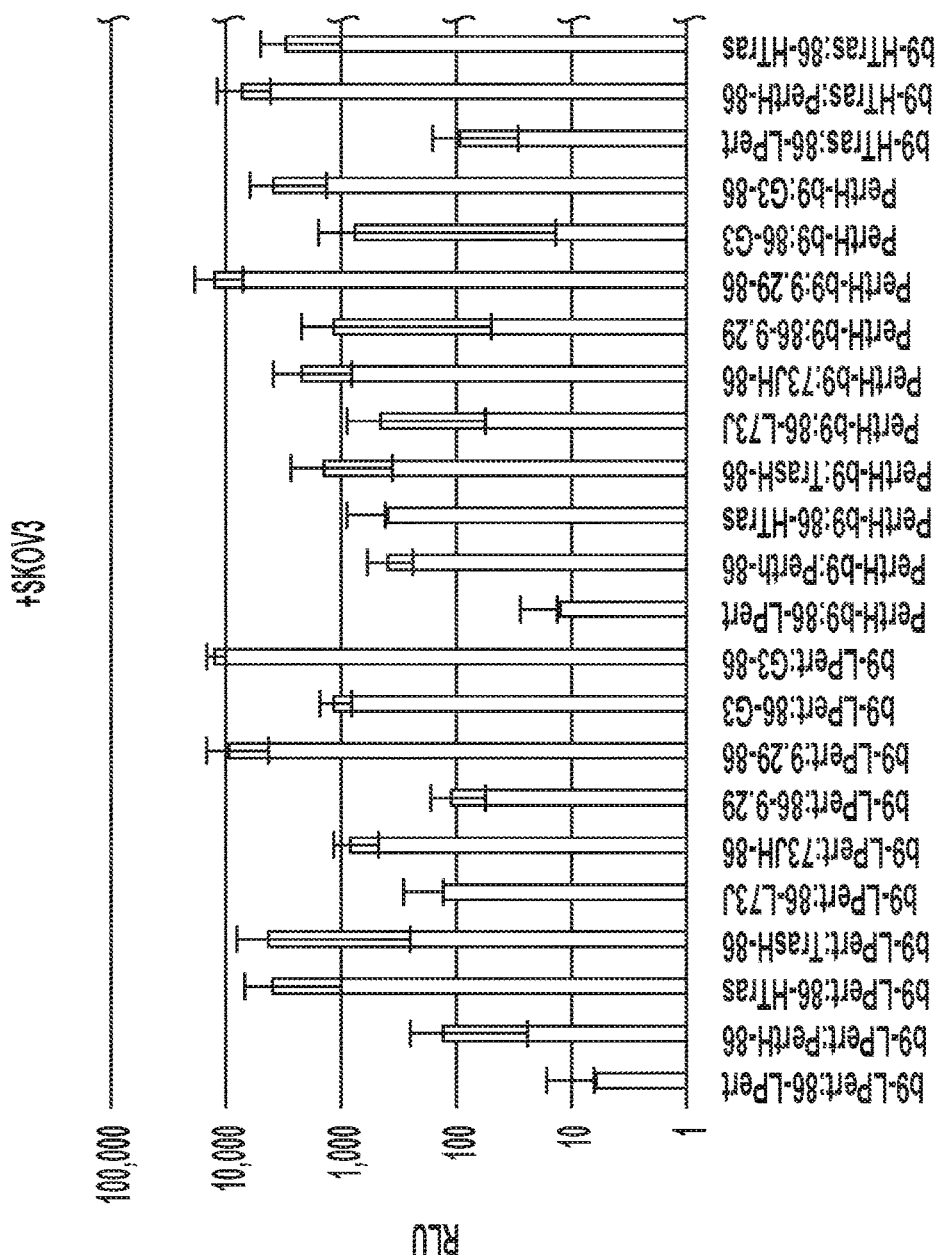
FIG. 13 is a bar chart showing luminescence of various targeted split enzyme reporter systems in the presence of a target antigen.
Figure 14:
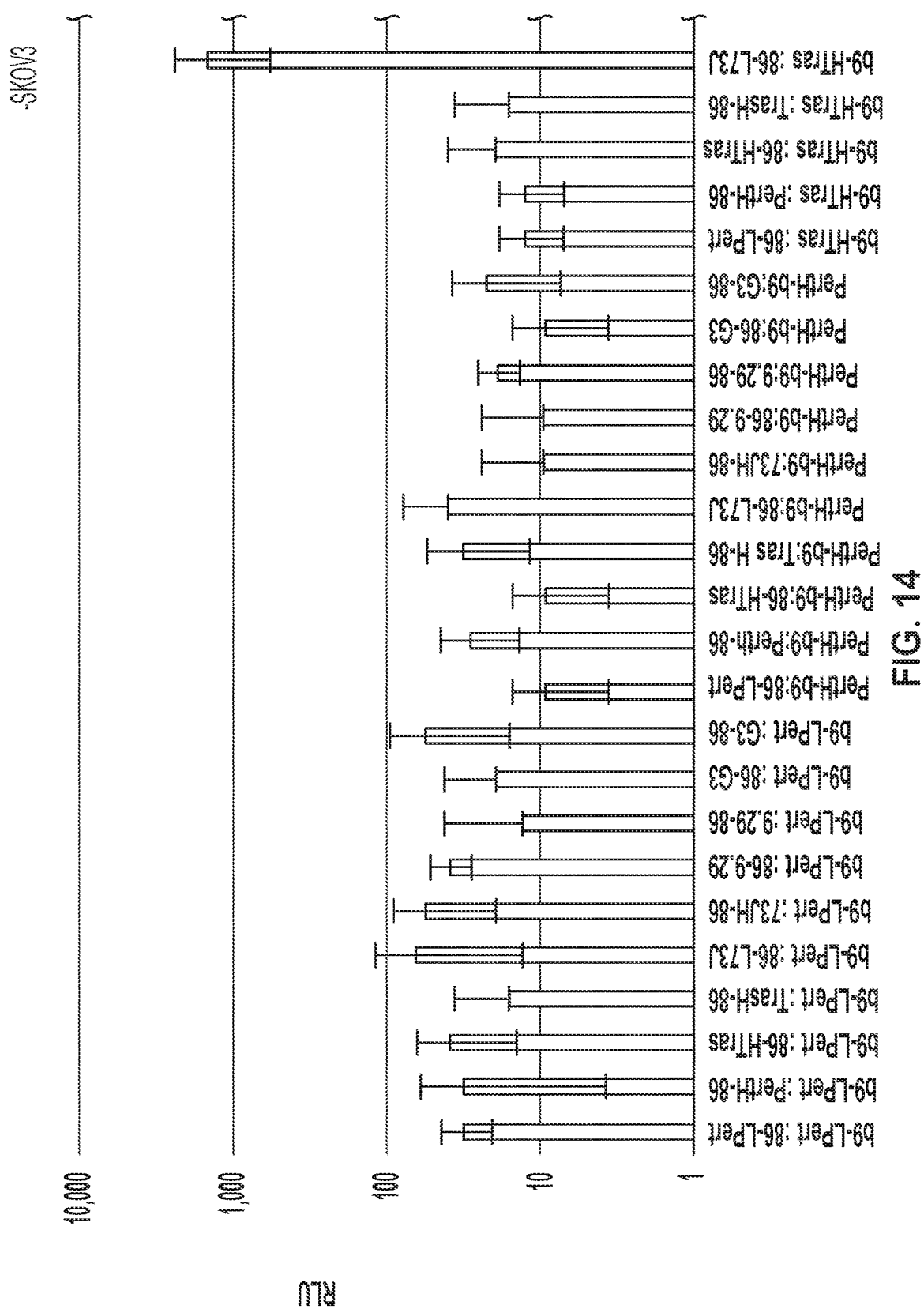
FIG. 14 is a bar chart showing luminescence of various targeted split enzyme reporter systems in the absence of a target antigen.
Figure 14:
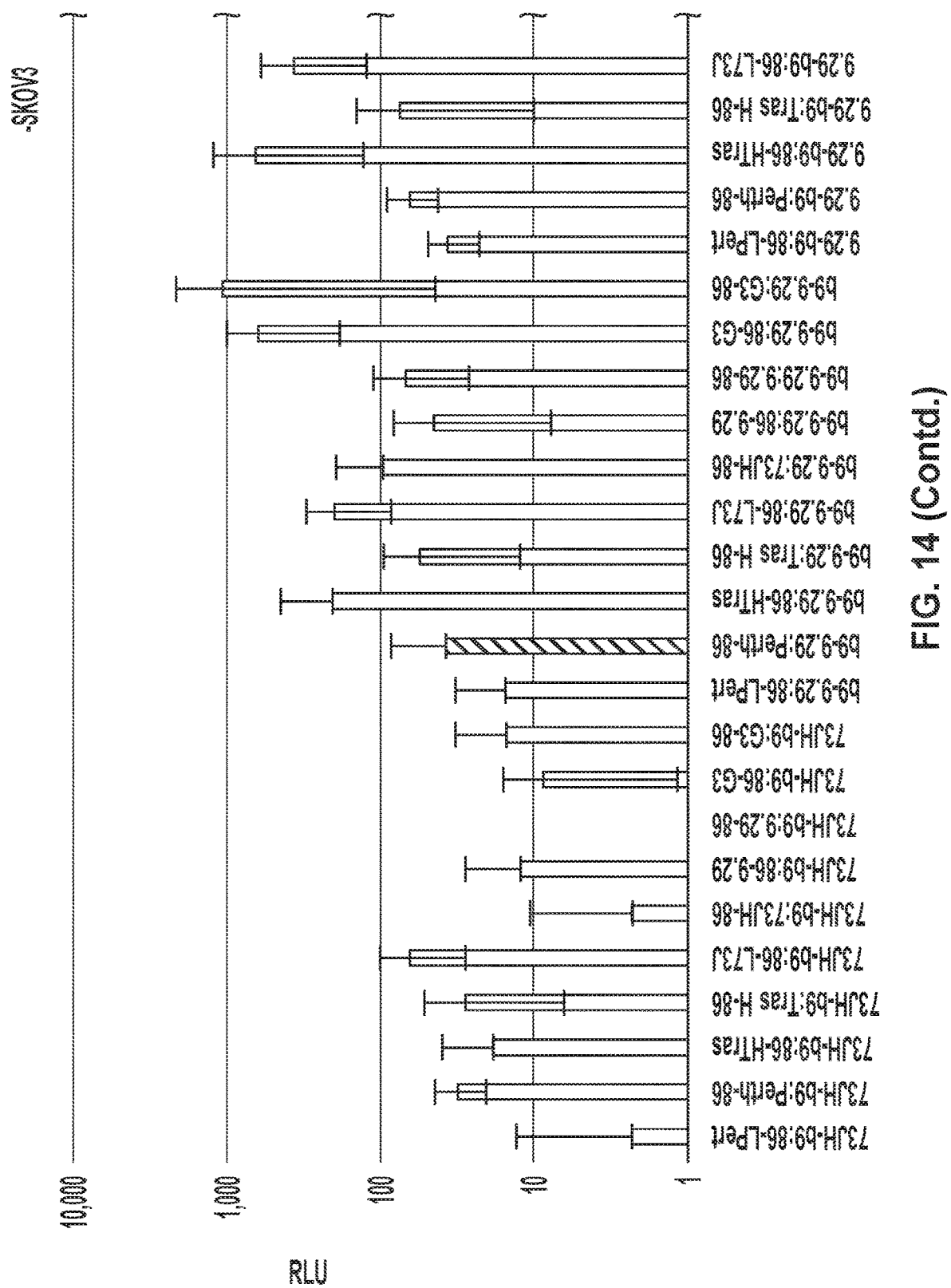
Figure 14:
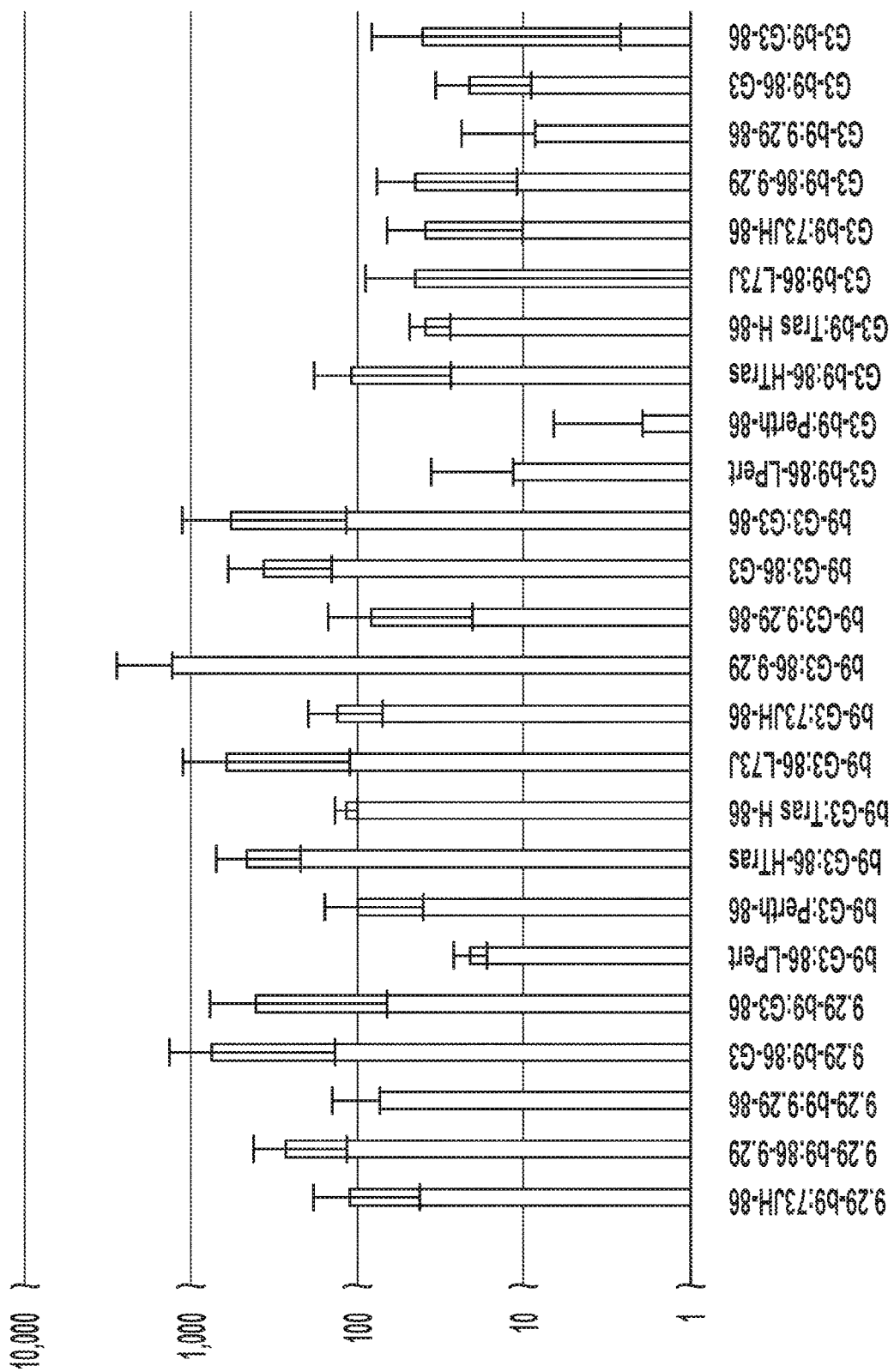

The cells were then lysed, and the concentration was normalized through luminescence. All possible pairs were screened on HER2+ SKOV3 cells. More particularly, cells were incubated with the two binder fusion proteins at ambient temperature. The cells were then washed, Δ11S and substrate (furimazine) were added, and luminescence was measured. The results are shown in FIGS. 13-14, with the −SKOV3 cells of FIG. 14 serving as a control.

The average signal-to-background results from this screen (as performed on three separate days) are summarized in Table 3.

TABLE 3

| Signal-to-Background Measurements (Ratio of Relative Luminescence Units) | | | | | | | | | | |
|---|---|---|---|---|---|---|---|---|---|---|
| | β9-LPert | PerH-β9 | β9-HTras | TrasH-β9 | β9-L73J | 73JH-β9 | β9-9.29 | 9.29-β9 | β9-G3 | G3-β9 |
| β10*-LPert | 0 ± 0 | 0 ± 0 | 3 ± 2 | 1 ± 1 | 1 ± 1 | 1 ± 1 | 2 ± 1 | 2 ± 2 | 2 ± 0 | 3 ± 1 |
| PertH-β10* | 4 ± 3 | 11 ± 4 | 211 ± 81 | 128 ± 31 | 367 ± 221 | 38 ± 17 | 671 ± 284 | 345 ± 130 | 65 ± 29 | 122 ± 80 |
| β10*-HTras | 108 ± 78 | 11 ± 12 | 80 ± 49 | 6 ± 4 | 7 ± 2 | 18 ± 13 | 167 ± 153 | 2 ± 1 | 5 ± 1 | 45 ± 26 |
| TrasH-β10* | 114 ± 104 | 40 ± 29 | 11 ± 7 | 6 ± 3 | 83 ± 71 | 9 ± 8 | 44 ± 22 | 60 ± 45 | 33 ± 26 | 61 ± 39 |
| β10*-L73J | 4 ± 4 | 12 ± 11 | 3 ± 1 | 6 ± 3 | 2 ± 1 | 3 ± 1 | 173 ± 208 | 9 ± 4 | 21 ± 23 | 126 ± 102 |
| 73JH-β10* | 23 ± 9 | 60 ± 37 | 170 ± 43 | 25 ± 12 | 6 ± 3 | 7 ± 2 | 81 ± 52 | 39 ± 26 | 219 ± 91 | 95 ± 35 |
| β10*-9.29 | 3 ± 1 | 31 ± 28 | 38 ± 26 | 5 ± 6 | 93 ± 72 | 4 ± 2 | 13 ± 13 | 1 ± 1 | 4 ± 4 | 12 ± 6 |
| 9.29-β10* | 265 ± 137 | 346 ± 135 | 40 ± 4 | 29 ± 14 | 597 ± 352 | 13 ± 5 | 99 ± 49 | 5 ± 3 | 122 ± 84 | 75 ± 48 |
| 8β10*G3 | 32 ± 8 | 21 ± 20 | 87 ± 45 | 15 ± 10 | 197 ± 80 | 21 ± 14 | 36 ± 13 | 11 ± 12 | 7 ± 3 | 28 ± 12 |
| G3-β10* | 353 ± 63 | 103 ± 62 | 508 ± 108 | 118 ± 58 | 1358 ± 455 | 47 ± 29 | 19 ± 12 | 31 ± 27 | 12 ± 7 | 93 ± 37 |

Within this set, each pair was tested with both possible orientations of the peptides (e.g., G3-β10*: TrasH-39 and G3-β9:TrasH-β10*). There was little correlation between the results obtained upon swapping the peptide fused to each binder. Furthermore, only four of the top 20 pairs involved 39 as a C-terminal fusion. Similarly, four (but not the same four found with C-terminal 39) out of the top 20 pairs involved β10* as an N-terminal fusion. Together, the data suggest that the complementation system functions preferentially, but not exclusively, when β9 is an N-terminal fusion and β10* is a C-terminal fusion. Twenty-three pairs produced a signal (relative luminescence units) at least 100-fold higher than background. The top two pairs—β9-L73J:G3-β10* and β9-9.29: PertH-β10*—were selected for further characterization and analysis.

Validation of Target-Engaged Complementation

Figure 15:
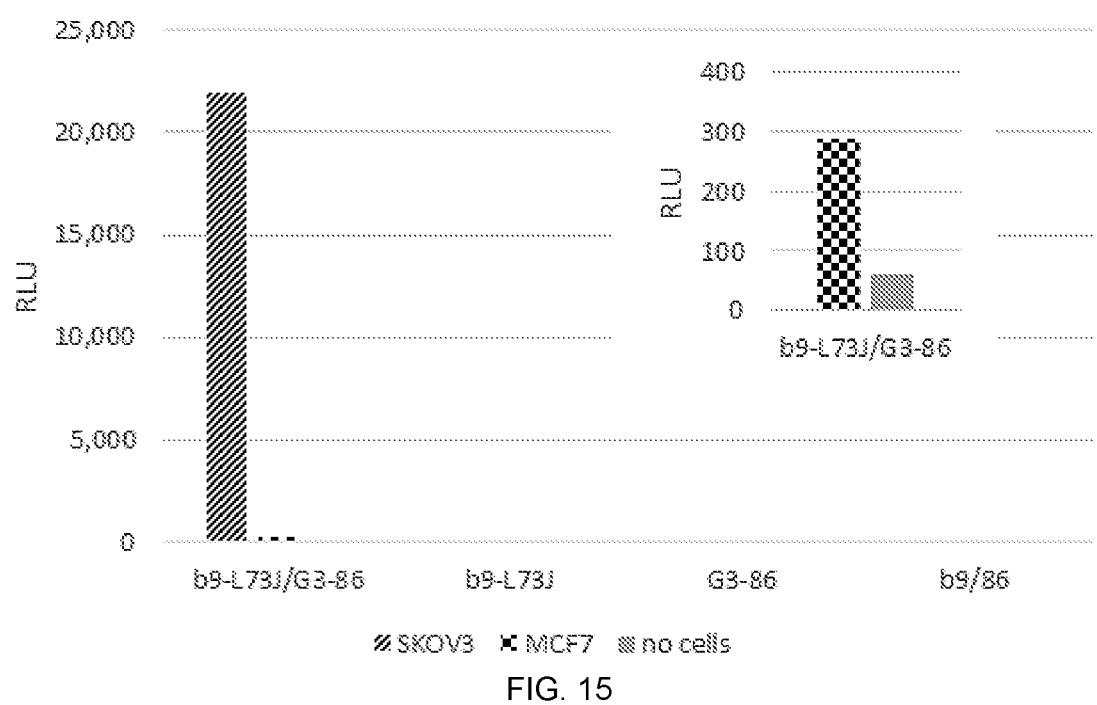
FIG. 15 is a bar graph depicting luminescent activity of various split enzyme reporter systems.
Figure 16:
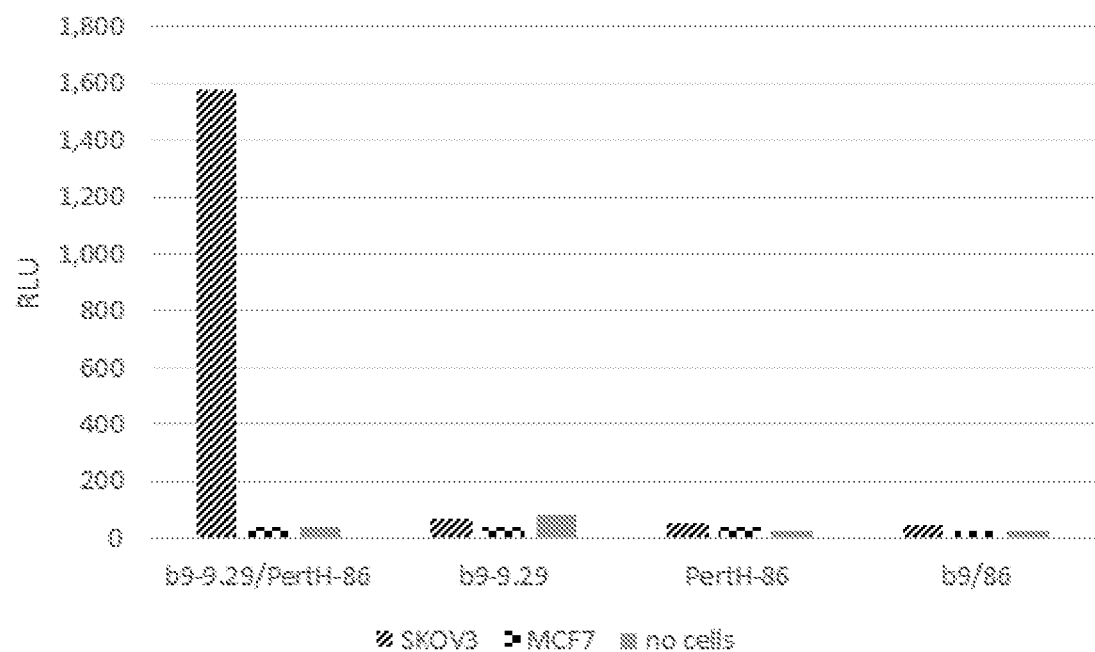
FIG. 16 is a bar graph depicting luminescent activity of various split enzyme systems.

Unpurified antibody and DARPin fusions (β9-L73J:G3-β10* and β9-9.29: PertH-β10*) from lysates were validated by their binding to HER2+ SKOV3 cells as described above. As shown in FIGS. 15-16, in the absence of HER2 (no cells), negligible signal is generated. Similarly, no significant luminescence was produced when less than all of the components of the fragment complementation system were added. However, when the proper pair of fusion proteins was introduced into the system, a luminescent signal was produced. The assay also distinguished between low (MCF-7) and high (SKOV3) HER2 expressing cells. See FIGS. 15-16.

Subsequently, the same assay was run with purified fusion proteins. More particularly, the β9-L73J:G3-β10* and β9-9.29:PertH-β10* fusion proteins were produced recombinantly in E. coli. Each of these fusion proteins included a His-Tag, enabling purification using standard immobilized metal affinity chromatography (IMAC) procedures. Block et al., 463 Methods Enzymol 439-73 (2009). The purified proteins retained ≥90% of the activity of the originating lysate, even after storage for over one month.

Figure 17:
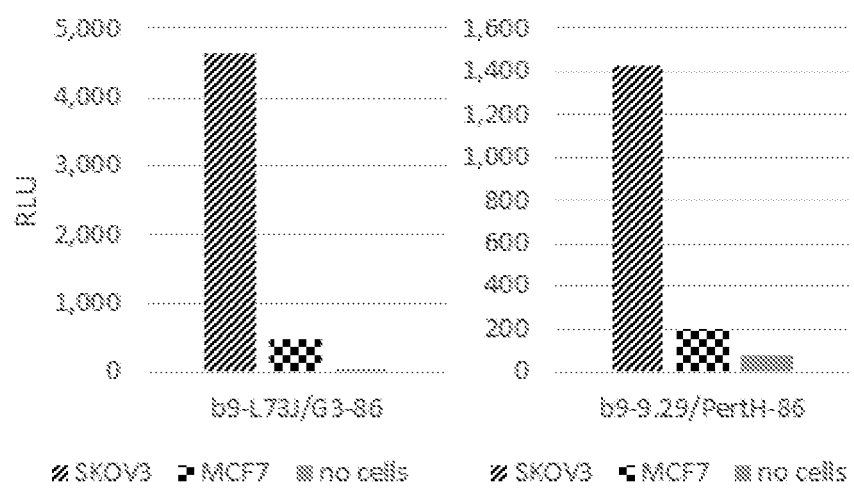
FIG. 17 is a bar graph depicting luminescent activity of two targeted split enzyme reporter systems using purified fusions.
Figure 18:
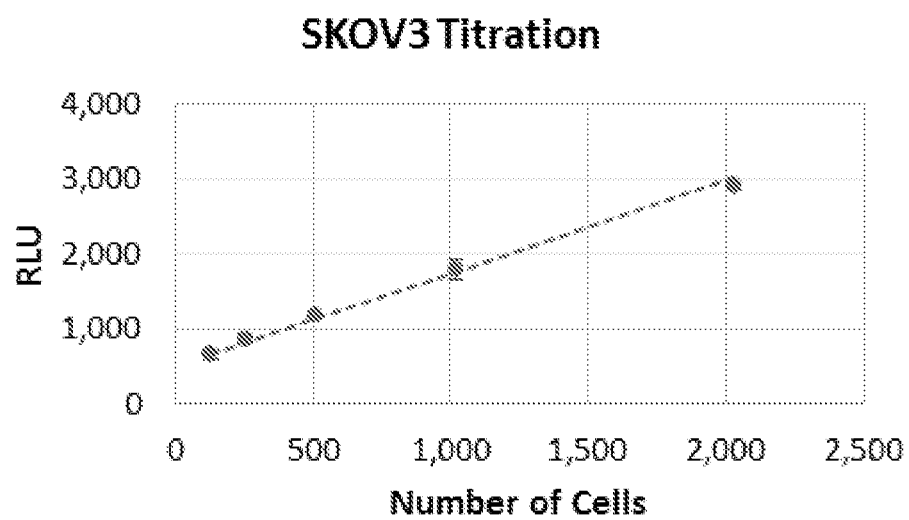
FIG. 18 is a plot showing luminescent activity as a function of the number of HER2$^+$ cells.

The data for the purified fusion proteins is shown in FIGS. 17 and 18. As shown in these figures, the purified proteins could be used to detect and quantify HER2, and could be used to differentiate between low (MCF-7) and high (SKOV3) HER2-expressing cells.

Immunoassay without Wash Step

HER2+ SKOV3 cells were introduced into wells of a multi-well plate. β9-binder, β10*-binder, Δ11S, and furimazine were added to each well. In contrast to other HER2 assays described herein, the unbound antibodies were not washed away. In other words, luminescence was detected without any intervening wash step.

Figure 19:
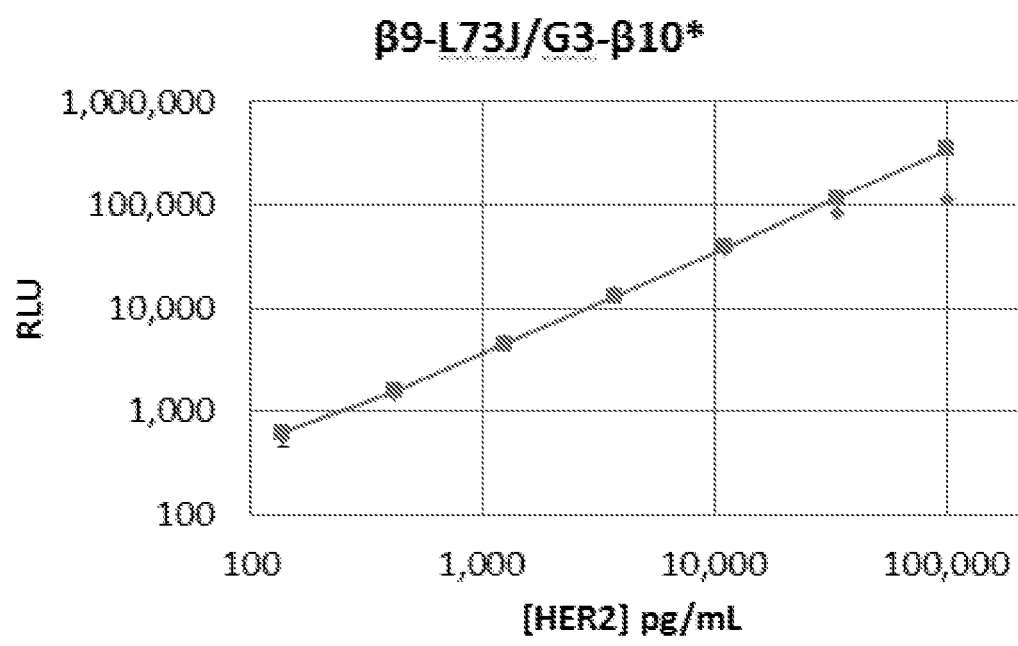
FIG. 19 is a plot showing luminescent activity of a targeted split enzyme reporter system as a function of HER2 concentration.
Figure 20:
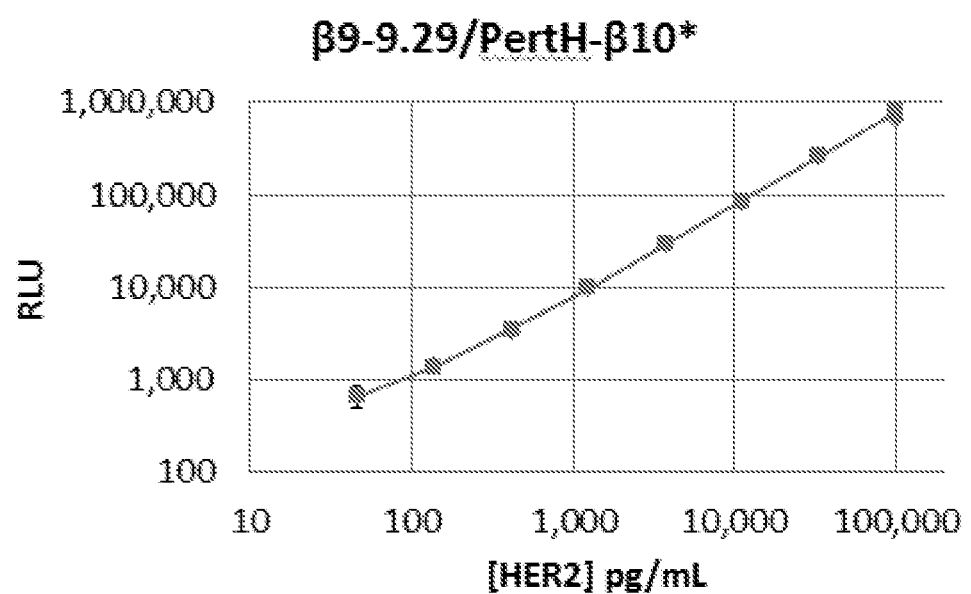
FIG. 20 is a plot showing luminescent activity of another targeted split enzyme reporter system as a function of HER2 concentration.

The concentration of each fusion protein was tailored so as to provide sufficient binder to bind the antigen (i.e., HER2) while keeping the concentration of the peptide relatively low so as to minimize complementation (and background signal) in the absence of the antigen. To this end, the concentration of each fusion in both target-engaged complementation pairs was optimized. Low nM concentrations were found to be appropriate. The resulting luminescence data collected two hours after incubation is shown in FIGS. 19-20. More particularly, FIG. 19 provides data for β9-L73J/G3-β10* target-engaged complementation. And FIG. 20 provides data for β9-9.29/PertH-β10* target-engaged complementation.

Figure 21:
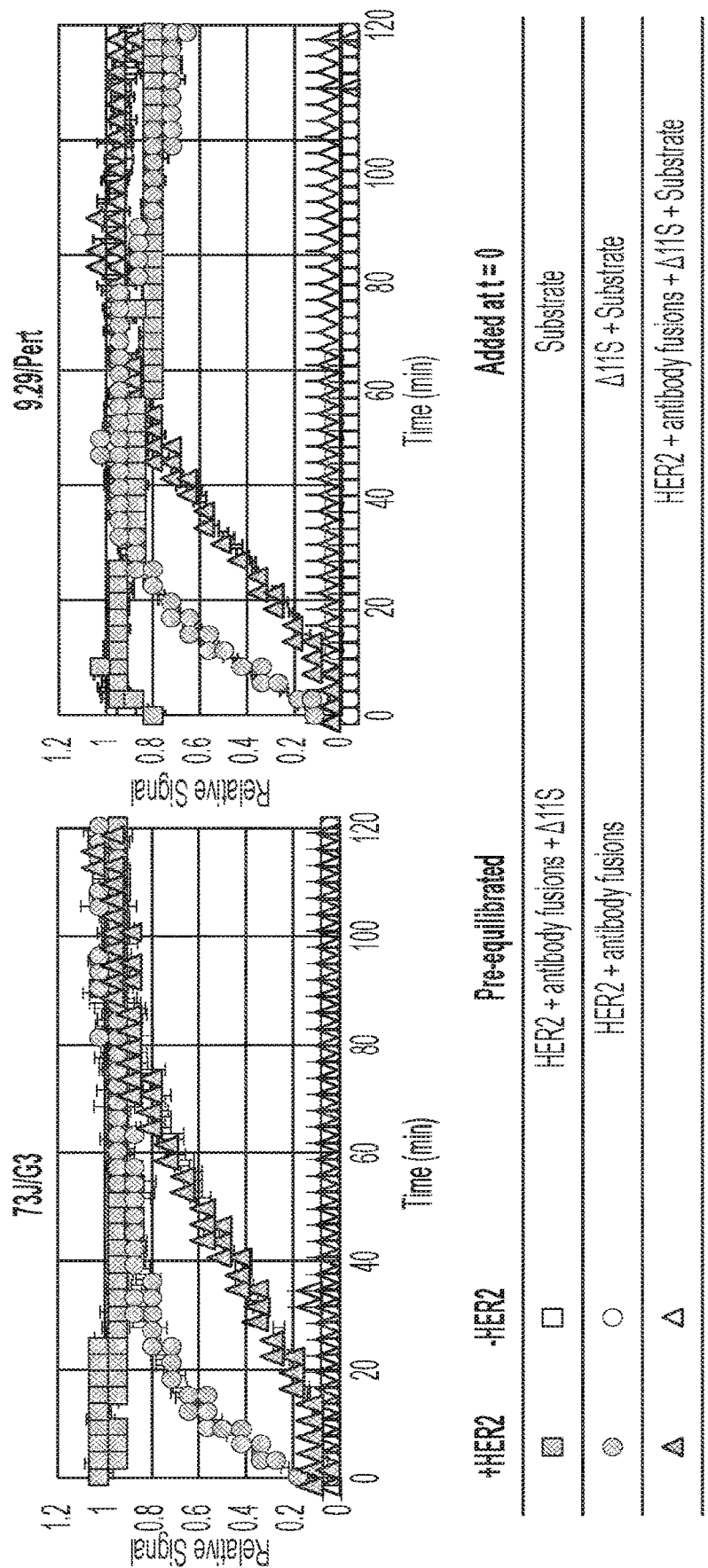
FIG. 21 includes scatterplots that illustrate the binding kinetics of components of a targeted split enzyme reporter system.

In assays such as this one, where each of the three components of the tripartite split enzyme are added at once, the binding kinetics may influence the optimal time for measuring luminescence. In addition to binding of the targeting domain (e.g., Fab or DARPin) to the analyte (e.g., HER2), Δ11S also needs to bind to β9/β10* to form the active luciferase complex. To evaluate when to measure the signal and to differentiate binding of the targeting domain from formation of the luciferase complex, kinetics studies were performed. As shown in FIG. 21, the signal kinetics from an experiment where each component of the target-engaged complementation system (and substrate) is simultaneously added to the mixture (HER2+β9-binder+β10*-binder+Δ11S+substrate; solid triangles) were compared to the kinetics where (1) both targeting domains (but not Δ11S or substrate) were pre-equilibrated with HER2 (HER2+β9-binder+β10*-binder) (closed circles) and (2) both targeting domains and Δ11S (but not substrate) were pre-equilibrated with HER2 (HER2+β9-binder+β10*-binder+Δ11S) (solid squares). When all components are pre-equilibrated with HER2 (solid squares), luminescence is immediately obtained. If Δ11S is not pre-equilibrated, but added with substrate to pre-equilibrated targeting domains (solid circles and solid triangles), the luminescent signal increases with time according to Δ11S binding and/or the formation of an active luciferase complex. The formation of the luciferase complex is slower for the 73J/G3 combination, reaching approximately 90% of the maximal signal at ~50 minutes, as compared to ~30 minutes for 9.29/Pertuzumab. Among other possibilities, this difference in rate may be a reflection of a larger distance of separation between the fused termini. As expected, when the targeting domains are not pre-equilibrated with HER2, an increased time was required to achieve the maximal signal, consistent with the requirement for both targeting domain and Δ11S binding. The kinetics data demonstrate that the maximal signal is obtained within two hours. Furthermore, for 9.29/Pertuzumab, signal-to-background of five was obtained within 20 minutes, demonstrating the feasibility of this relatively fast and simple single-step assay.

To determine the sensitivity of the assay, the following definitions were noted as outlined by Armbruster and Pry (Armbruster & Pry, Clin Biochem Rev 29 Suppl 1, S49-52 (2008)):

$$\text{Limit of Blank } (LoB) = \text{mean } RLU_{blank} + 1.645 \times SD_{blank}$$

$$\text{Limit of Detection } (LoD) = LoB + 1.645 \times SD_{low\ concentration\ sample}$$

As opposed to using the definition for the limit of detection and extrapolating to a concentration that had not actually been tested, the LoD was defined as the lowest concentration measured that produced a signal greater than the LoB+1.645 times the standard deviation. For 73J/G3, the LoD was 137 pg/mL and the linear range extended up to a concentration of 11 ng/ml. The combination of 9.29 and Pertuzumab was found to exceed these capabilities in terms of both the limit of detection and the linear range. The LoD for this pair was determined to be 45 pg/mL. Although 100 ng/ml seems to be close to lying within the linear range, the small standard deviation of this assay would suggest that it does not, and the highest concentration assayed that remained in the linear range was 33 ng/mL. A previous demonstration using complementation to detect HER2 reported the ability to detect 500 pM HER2 (Stains et al. ACS Chem Biol 5, 943-52 (2010)). These results demonstrate the ability to detect sub-picomolar concentrations (0.7 pM), an improvement of approximately 500-fold. Further, commercially available ELISA kits report sensitivities in the range of 8-24 pg/mL with linear ranges up to approximately 5 ng/ml. The sensitivity and dynamic range demonstrated here is comparable to the sensitivity and dynamic range of these commercially available ELISA assays. This is particularly impressive, considering that many standard ELISA kits involve signal amplification by binding multiple antibodies per antigen and/or multiple enzymes per antibody. In contrast, for every pair of bound targeting domains, the signal demonstrated here is limited to the signal generated from a single active luciferase complex that is formed via target-engaged complementation.

Analyte Detection in Human Serum

Figure 22:
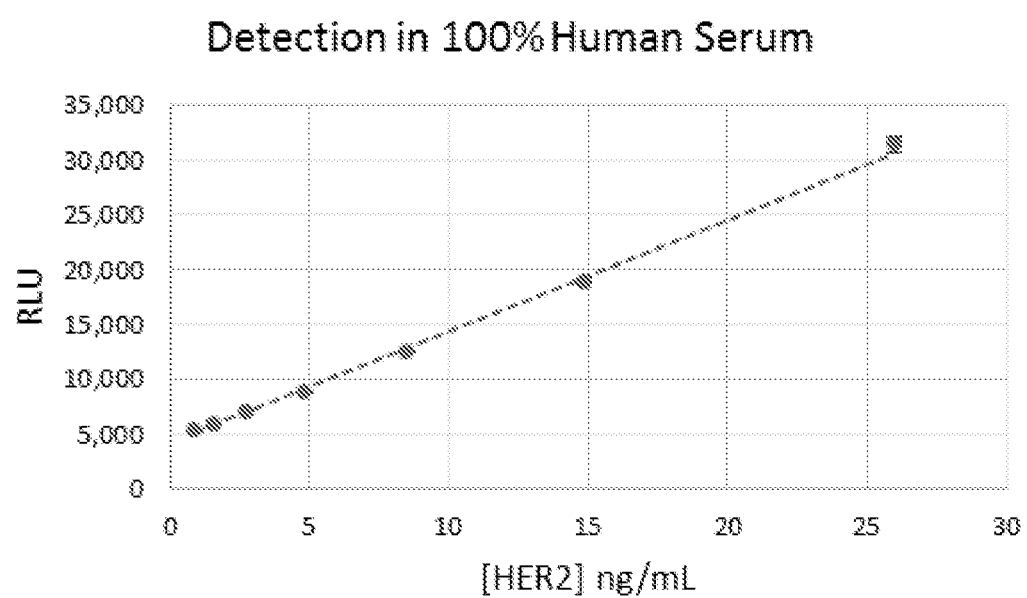
FIG. 22 is a graph showing luminescent activity as a function of HER2 concentration in human serum.

As soluble HER2 may be used to monitor the treatment efficacy and recurrence of cancer (see, e.g., Tse et al., *Cancer Treat Rev* 38, 133-42 (2012); Mokuyasu et al., *Rinsho Byori* 60, 612-20 (2012); Cook et al., *Anticancer Res* 21, 1465-70 (2001)), a target-engaged complementation reporter was used to investigate detection of HER2 in human serum. As the threshold for elevated HER2 in serum has been established at >15 ng/ml, HER2 was spiked into human serum at low ng/ml concentrations. A target-engaged complementation assay was then performed using the combination of 9.29 and Pertuzumab (for 39-9.29/PertH-β10*). Given the complex nature and high concentration of proteins in serum, serum is a particularly challenging mixture for a solution-based application of target-engaged complementation. Despite these challenges, target-engaged complementation successfully differentiated between small differences in HER2 concentrations and was linear across the low ng/ml range as shown in FIG. 22. This demonstrates that target-engaged complementation can be used to differentiate between biologically relevant concentrations of HER2 in human serum.

The foregoing data show that HER2 can be quantified via a simple, rapid, and sensitive method. The method is generalizable to other analytes (e.g., proteins) of interest. Further, while the data disclosed herein is most analogous to a traditional ELISA, analogous methods may be used in immunocytochemistry and immunohistochemistry as well.

Figure 23:
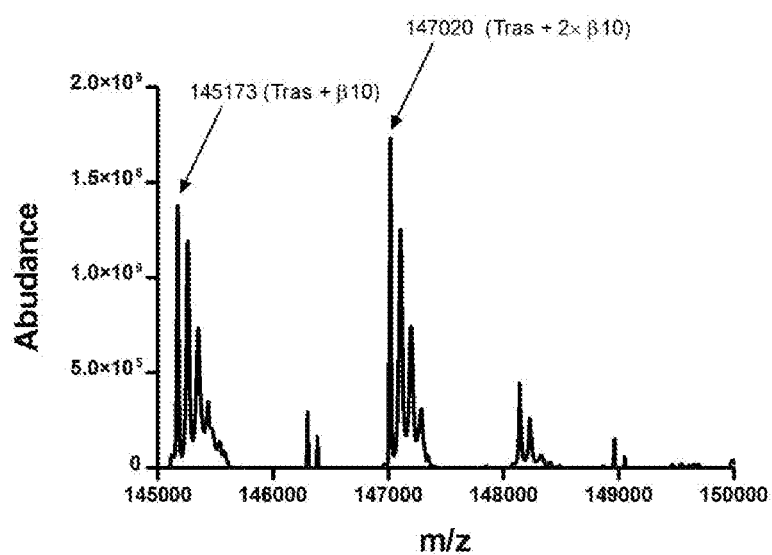
FIG. 23 provides mass spectrometry data of a chemically conjugated agent that includes a peptide fragment and a targeting domain.
Figure 24:
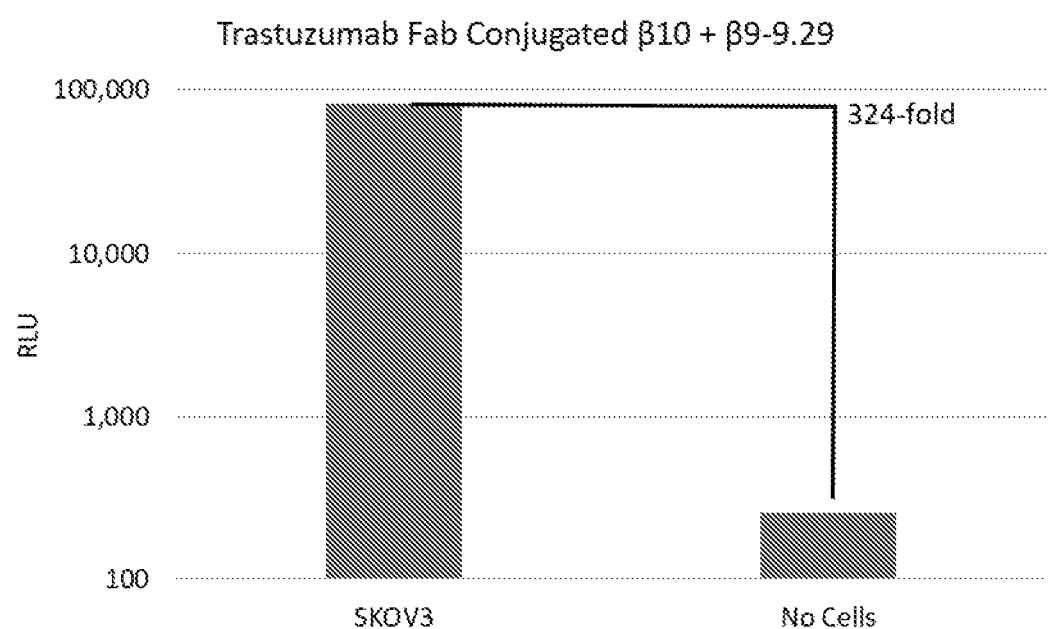
FIG. 24 is a bar graph showing luminescence from a targeted split enzyme reporter system that includes a chemically conjugated peptide fragment.

Target-Engaged Complementation with Split Enzyme Fragments that are Produced by Chemical Conjugation A maleimide-β10* peptide was chemically conjugated to the full IgG form of Trastuzumab using 2-iminothiolane. Conjugation was verified by mass spectrometry as shown in FIG. 23. The mass spectrometry data showed that either one or two β10* fragments were conjugated per antibody. The utility of the chemically conjugated fragment for use in target-engaged complementation was then investigated by combining the chemically conjugated fragment with complementary peptide fragments (β9-9.29 and Δ11S) in the presence and the absence of HER2+ cells (SKOV3). The results are shown in FIG. 24. A 324-fold increase in signal was observed in the presence of HER2+ cells, demonstrating that a chemically conjugated peptide fragment can be used for target-engaged complementation.

Figure 25:
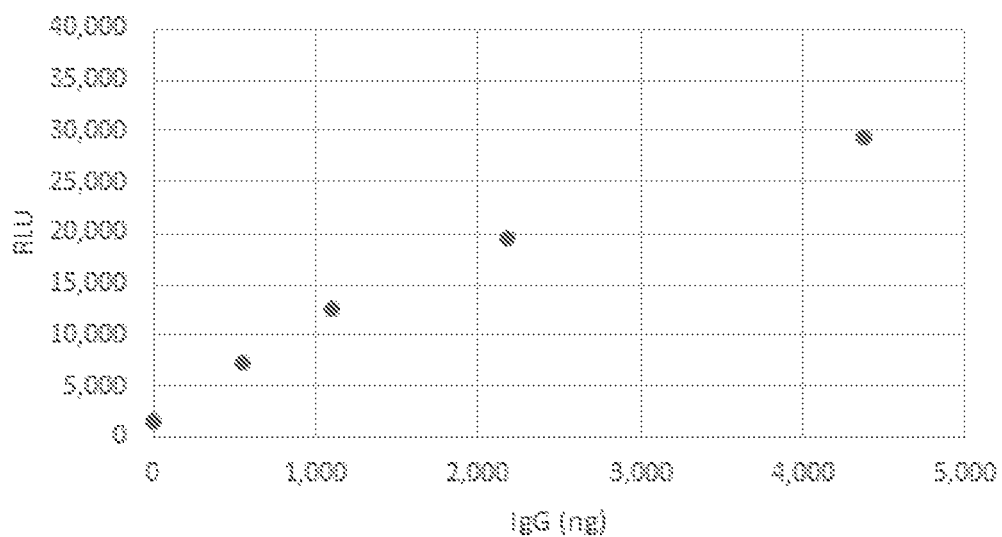
FIG. 25 is a scatterplot showing luminescent detection of IgG with a split enzyme reporter system having a first peptide fragment that is conjugated to Protein A and a second peptide fragment that is conjugated to Protein G.
Figure 26:
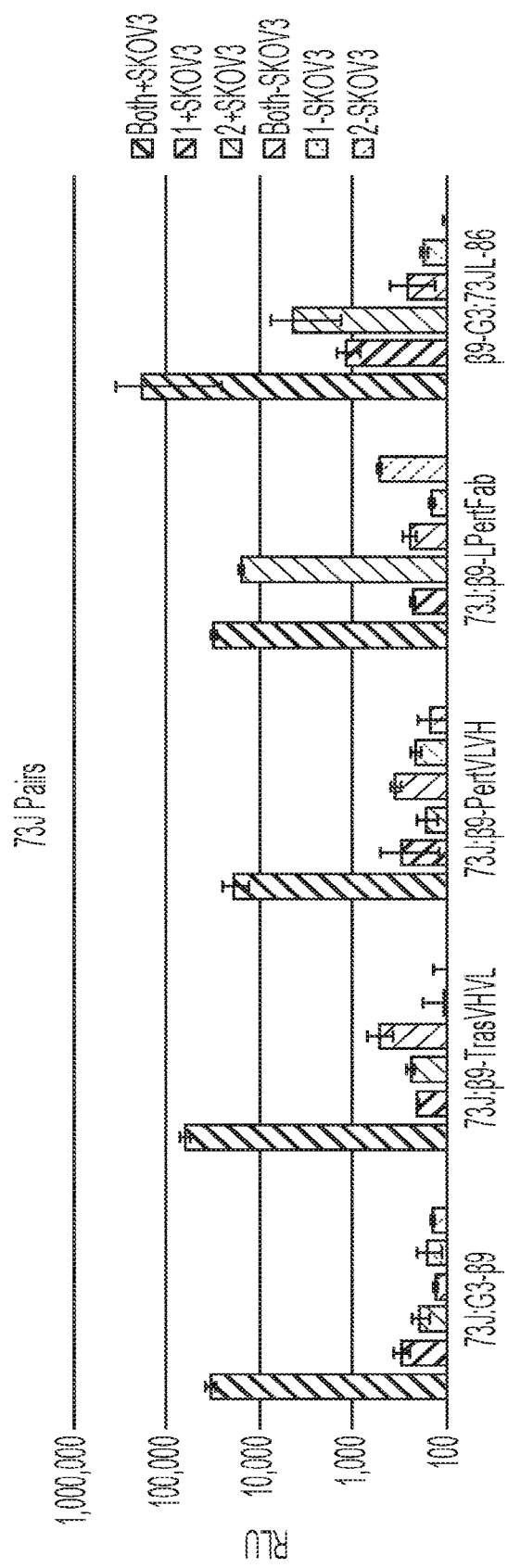
FIG. 26 is a bar chart showing luminescence generated by various targeted split reporter systems.
Figure 27:
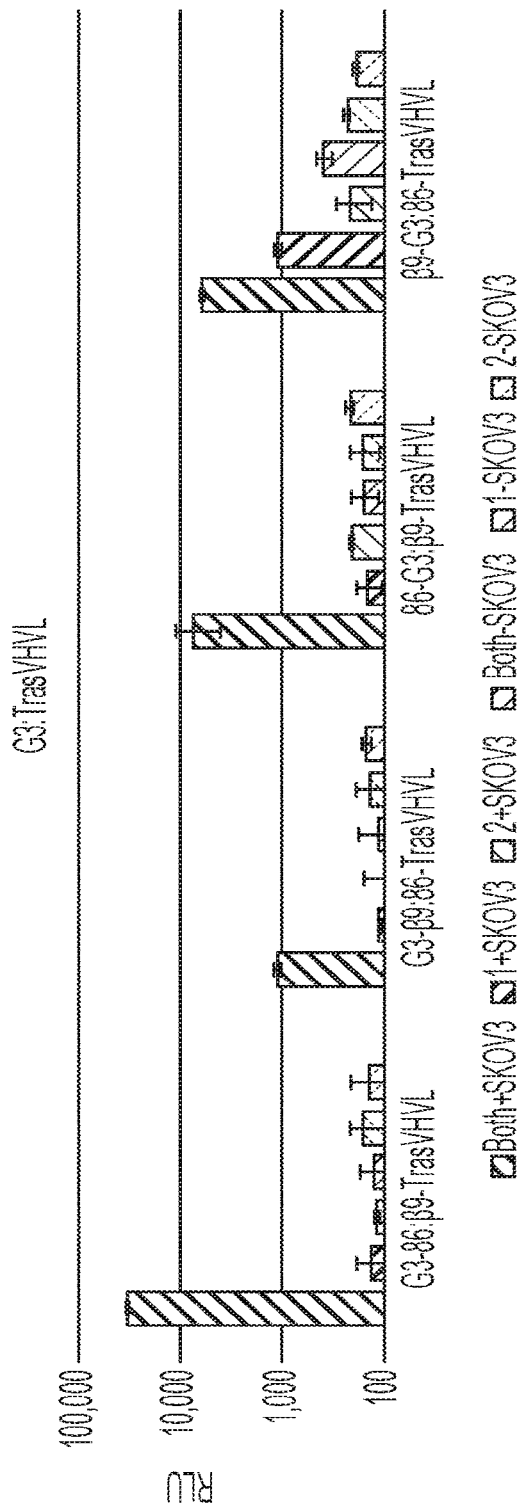
FIG. 27 is a bar chart showing luminescence generated by various targeted split reporter systems.
Figure 28:
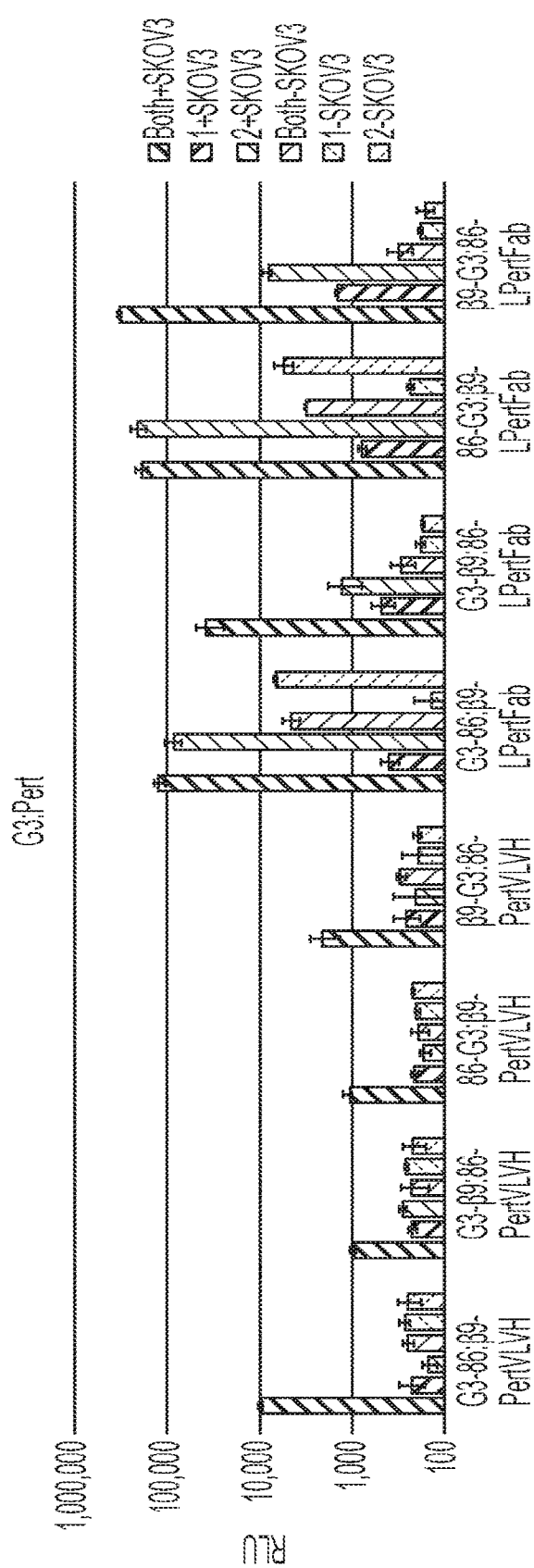
FIG. 28 is a bar chart showing luminescence generated by various targeted split reporter systems.
Figure 29:
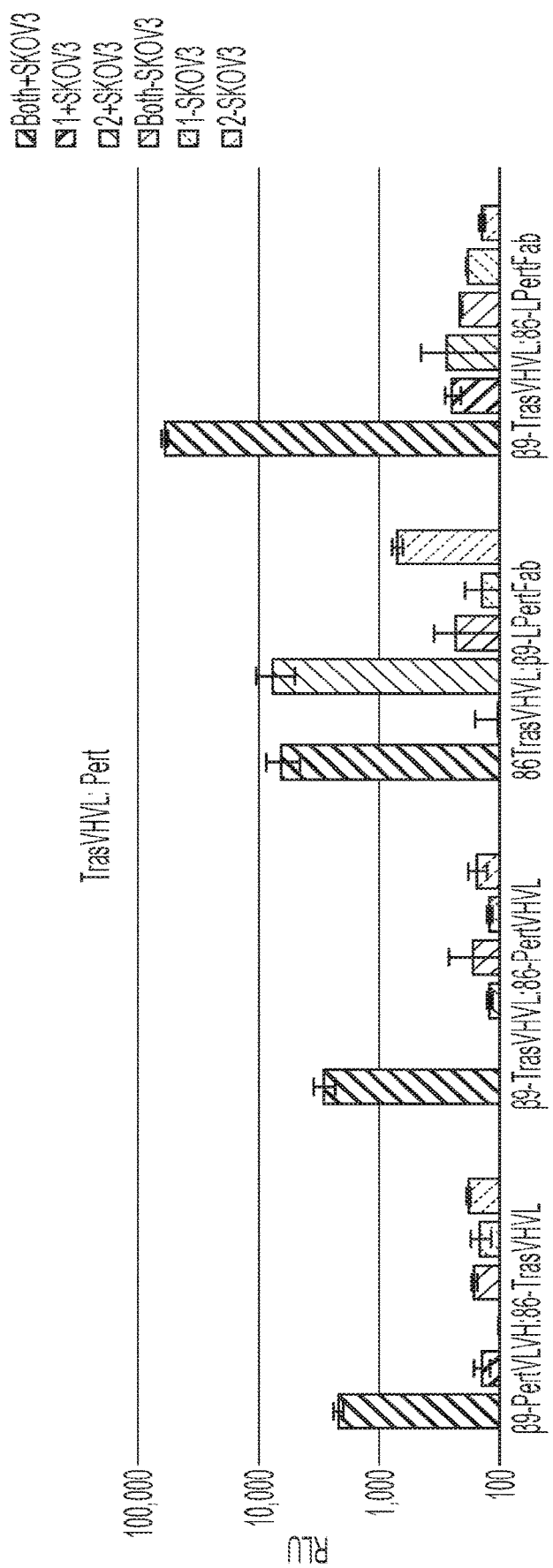
FIG. 29 is a bar chart showing luminescence generated by various targeted split reporter systems.

Target-Engaged Complementation Using Protein A and Protein G as Targeting Domains A split reporter system was used to detect IgG in solution. More specifically, a Protein A-β10* fusion protein and a Protein G-89 fusion protein were produced recombinantly. The ability of these peptide fragments to detect IgG (based on the affinity of Protein A and Protein G for IgG) was evaluated by target-engaged complementation. More specifically, the two fusion protein fragments were combined with Δ11S in the presence of various amounts of IgG, and luminescence was measured. The resulting data is shown in FIG. 25. The data show that increased luminescent signal is generated with increasing concentrations of IgG, and that this target-engaged complementation system can be used to assess IgG concentrations in solution.

Further Target-Engaged Complementation Studies

The various fusion proteins shown in FIGS. 26-29 were recombinantly produced. More particularly, 73J and PertFab domains were produced as Fabs, G3 was produced as a DARPin, and TrasVHVL and PertVLVH were produced as single-chain variable fragments (scFv). Each fragment of each split enzyme reporter system was combined with various other fragments of the split enzyme reporter system. For example, as shown in the first set of bar graphs of FIG. 26 for 73J-β10*: G3-β9, each of the following combinations of elements was combined with Δ11S and substrate in either the presence or the absence of HER2+ cells: (1) 73J-β10* and G3-β9, (2) 73J-β10* alone, and (3) G3-β9 alone. Similar tests were carried out for twenty other protein complexes. The results shown in FIGS. 26-29 show that a wide variety of different targeting domains may be used for target-engaged complementation.

Detection of Adalimumab

Embodiments of the protein-fragment complementation system described herein (see FIG. 7 for a representative depiction) were used to detect adalimumab (also known as Humira), which is a monoclonal antibody with affinity to an epitope of tumor necrosis factor (TNF), also known as tumor necrosis factor alpha (TNFα). For instance, fusion proteins were created, where each fusion protein included both (1) a targeting domain (e.g., TNF, protein L, or Protein A) with affinity for adalimumab and (2) a peptide fragment β9 or β10* of a split reporter protein.

More particularly, Protein A (SpA), Protein L (PpL), and TNF (as a fusion to HaloTag® ("HT")) were expressed in *E. coli* (T7 SHuffle Express) as fusions with β9 or β10* at the N- or C-terminus. A lysate was prepared by sonicating the cells and centrifuging to separate out the insoluble material. Each TNF lysate was tested in combination with the opposite peptide (β9 with β10, or β10 with β9) fusion of Protein A and Protein L diluted in PBST. The luminescence produced in the absence (−Adal) or presence (+Adal) of 10 μg/mL adalimumab is shown in the bar graph of FIG. 30. The values shown are the averages from three replicate wells±standard deviation. The sequence listings for some of the fusion proteins (and corresponding nucleotide sequences) are identified in Table 4.

TABLE 4

| Sequence Listings | |
|---|---|
| HT-β9-TNF | SEQ ID NO 57 (nucleotide) |
| | SEQ ID NO 58 (amino acid) |
| HT-TNF-β9 | SEQ ID NO 59 (nucleotide) |
| | SEQ ID NO 60 (amino acid) |
| HT-β10*-TNF | SEQ ID NO 61 (nucleotide) |
| | SEQ ID NO 62 (amino acid) |
| HT-TNF-β10* | SEQ ID NO 63 (nucleotide) |
| | SEQ ID NO 64 (amino acid) |
| β9-TNF | SEQ ID NO 65 (nucleotide) |
| | SEQ ID NO 66 (amino acid) |
| TNF-β9 | SEQ ID NO 67 (nucleotide) |
| | SEQ ID NO 68 (amino acid) |
| β10*-TNF | SEQ ID NO 69 (nucleotide) |
| | SEQ ID NO 70 (amino acid) |
| TNF-β10* | SEQ ID NO 71 (nucleotide) |
| | SEQ ID NO 72 (amino acid) |
| β9-PpL | SEQ ID NO 73 (nucleotide) |
| | SEQ ID NO 74 (amino acid) |
| PpL-β9 | SEQ ID NO 75 (nucleotide) |
| | SEQ ID NO 76 (amino acid) |
| β10*-PpL | SEQ ID NO 77 (nucleotide) |
| | SEQ ID NO 78 (amino acid) |

TABLE 4-continued

Sequence Listings

| | |
|---|---|
| PpL-β10* | SEQ ID NO 79 (nucleotide) |
| | SEQ ID NO 80 (amino acid) |
| β9-SpA | SEQ ID NO 81 (nucleotide) |
| | SEQ ID NO 82 (amino acid) |
| SpA-β9 | SEQ ID NO 83 (nucleotide) |
| | SEQ ID NO 84 (amino acid) |
| β10*-SpA | SEQ ID NO 85 (nucleotide) |
| | SEQ ID NO 86 (amino acid) |
| SpA-β10* | SEQ ID NO 87 (nucleotide) |
| | SEQ ID NO 88 (amino acid) |
| β9-SpGA1 | SEQ ID NO 89 (nucleotide) |
| | SEQ ID NO 90 (amino acid) |
| SpGA1-β9 | SEQ ID NO 91 (nucleotide) |
| | SEQ ID NO 92 (amino acid) |
| β10*-SpGA1 | SEQ ID NO 93 (nucleotide) |
| | SEQ ID NO 94 (amino acid) |
| SpGA1-β10* | SEQ ID NO 95 (nucleotide) |
| | SEQ ID NO 96 (amino acid) |

Figure 30:
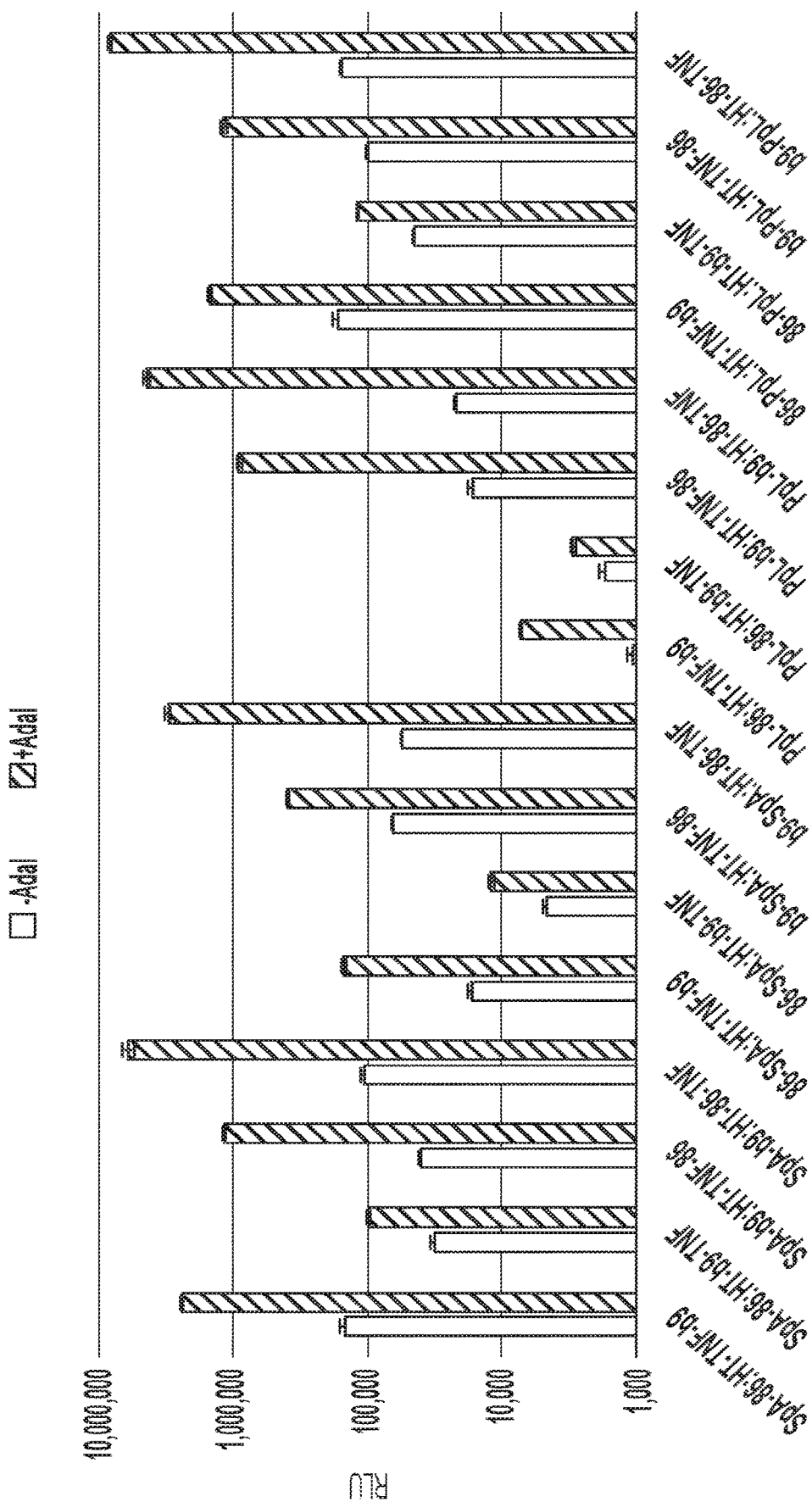
FIG. 30 is a bar chart showing luminescence generated by various targeted split enzyme reporter systems.
Figure 31:
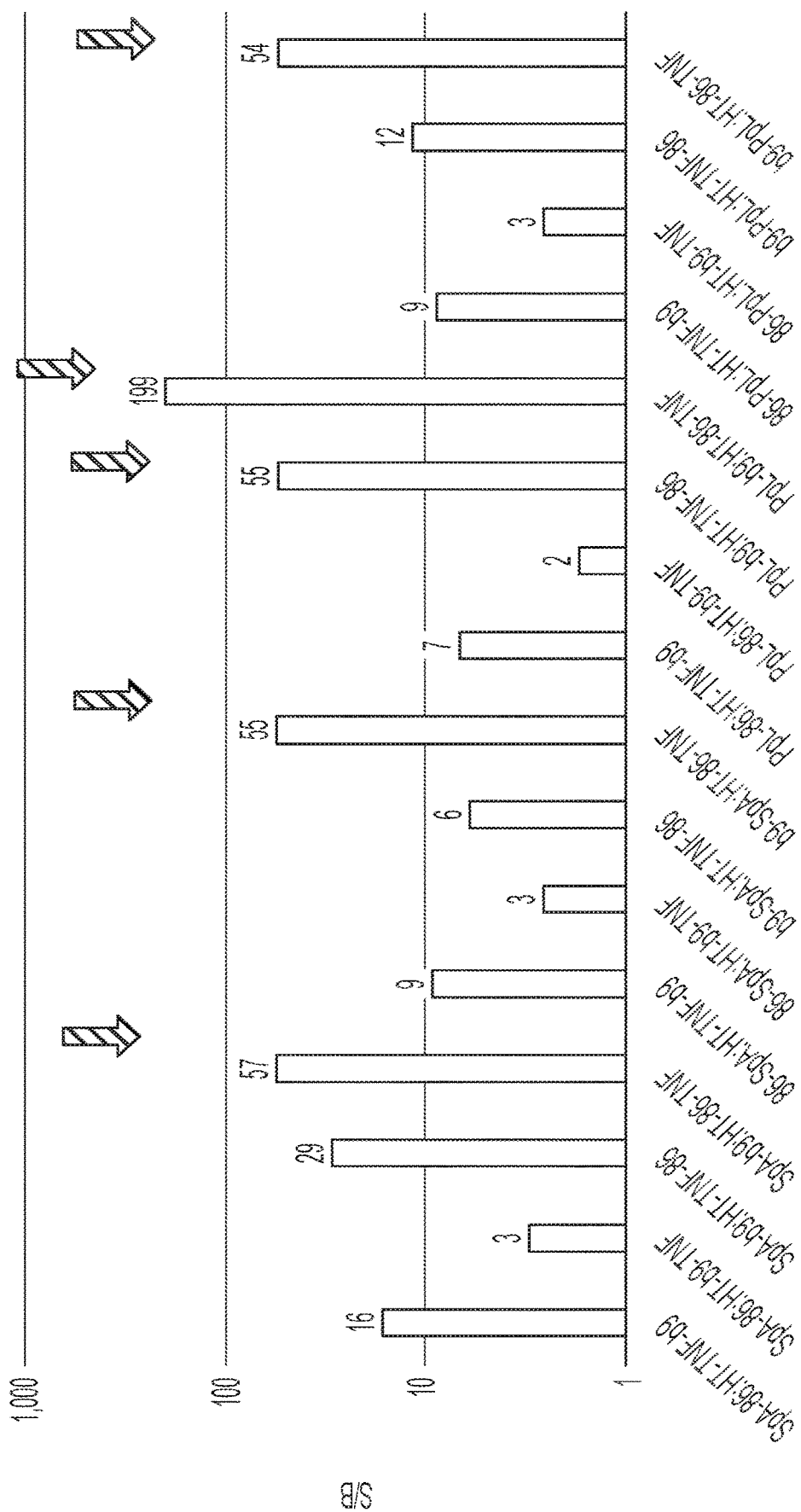
FIG. 31 is a bar chart showing the signal-to-background ratio for luminescence generated by the targeted split enzyme reporter systems of FIG. 32.

As shown in FIG. 30, increased luminescent signal was observed in the presence of adalimumab, demonstrating that the assay may be used to detect the antibody. The ratio of signal to noise for each pair of fusion proteins is shown in FIG. 31. Signal-to-background values were determined by dividing the luminescence produced in the presence of adalimumab (+Adal) by the luminescence produced in the absence of adalimumab (−Adal).

Four of the pairs of fusion proteins (protein A-β9:HT-β10*-TNF; β9-protein A:HT-β10*-TNF; protein L-β9:HT-TNF-β10*; protein L-β9:HT-β10*-TNF) were selected for further studies based on the high signal-to-noise ratio observed in the experiments reported in FIGS. 30 and 31.

Figure 32:
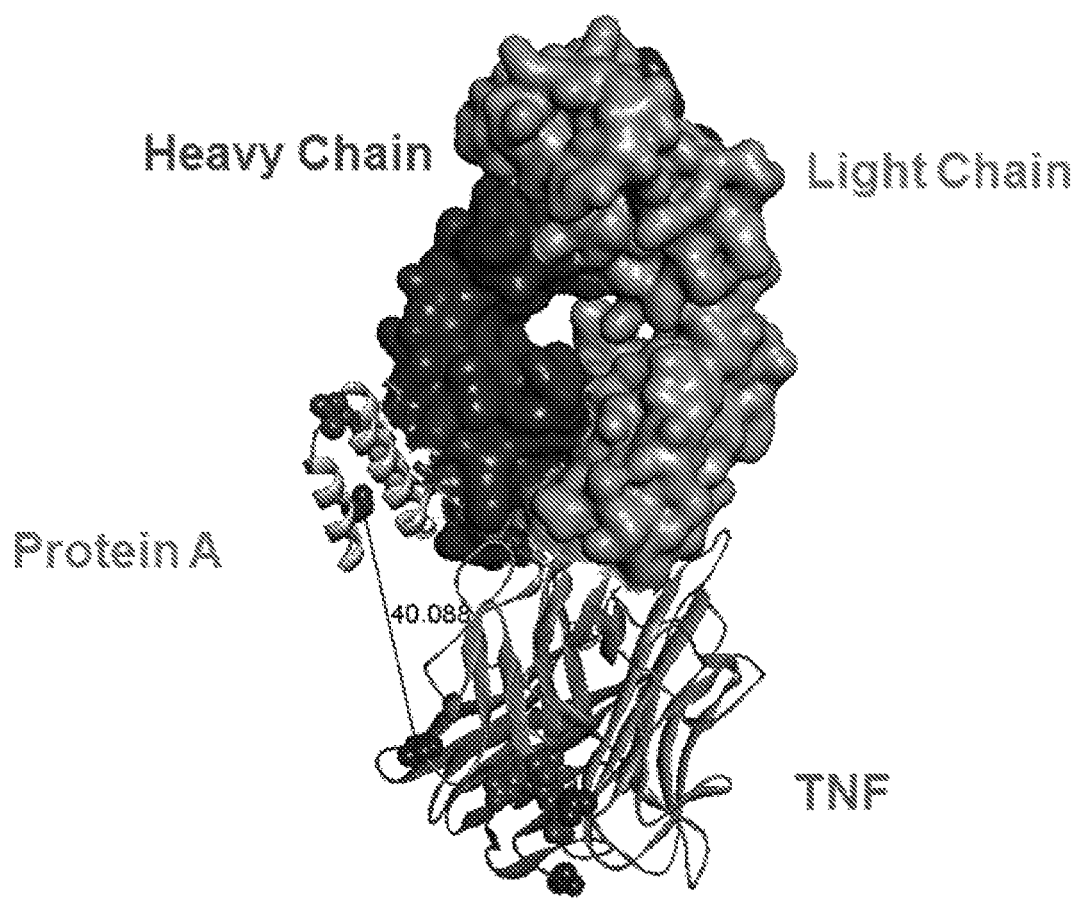
FIG. 32 is a structural model showing the binding of protein A and tumor necrosis factor (TNF) to adalimumab.
Figure 33:
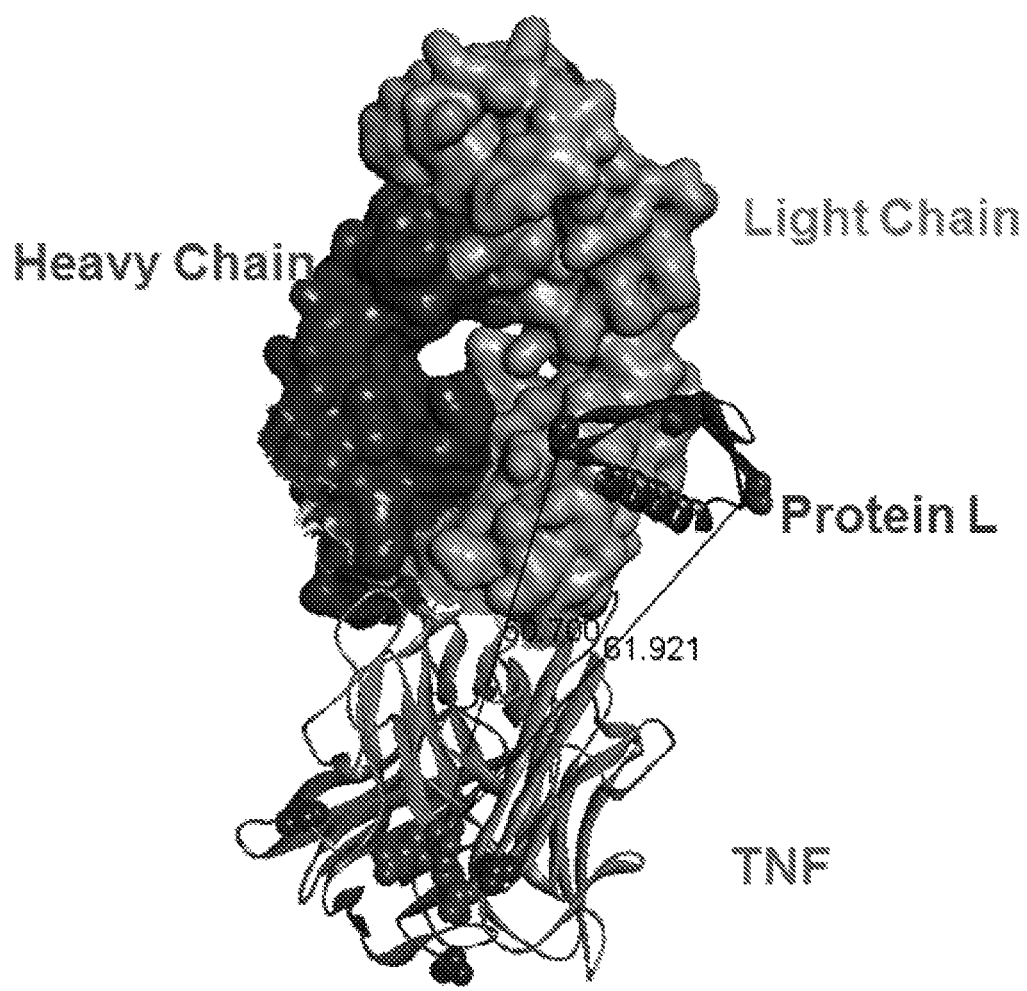
FIG. 33 is a structural model showing the binding of protein L and tumor necrosis factor to adalimumab.

For example, the four pairs of fusion proteins were used to detect adalimumab and infliximab (another antibody with affinity for TNF). Infliximab is shown bound to TNF and protein A in FIG. 32 and bound to TNF and protein L in FIG. 33. More particularly, infliximab was superimposed with trastuzumab using crystal structures in which infliximab is bound to TNF (PDB ID: 4G3Y) and trastuzumab is bound by Protein A and Protein L (PDB ID: 4HKZ). Once superimposed, trastuzumab was removed leaving infliximab, Protein A, Protein L, and TNF in their expected positions within the complex. The distance from the N-terminus of Protein A to the N-terminus of TNF was estimated to be 40 Å as shown in FIG. 32. The distance from the N-terminus and C-terminus of Protein L to the C-terminus of TNF were estimated to be 50.7 Å and 61.9 Å, respectively, as shown in FIG. 33.

Figure 34:
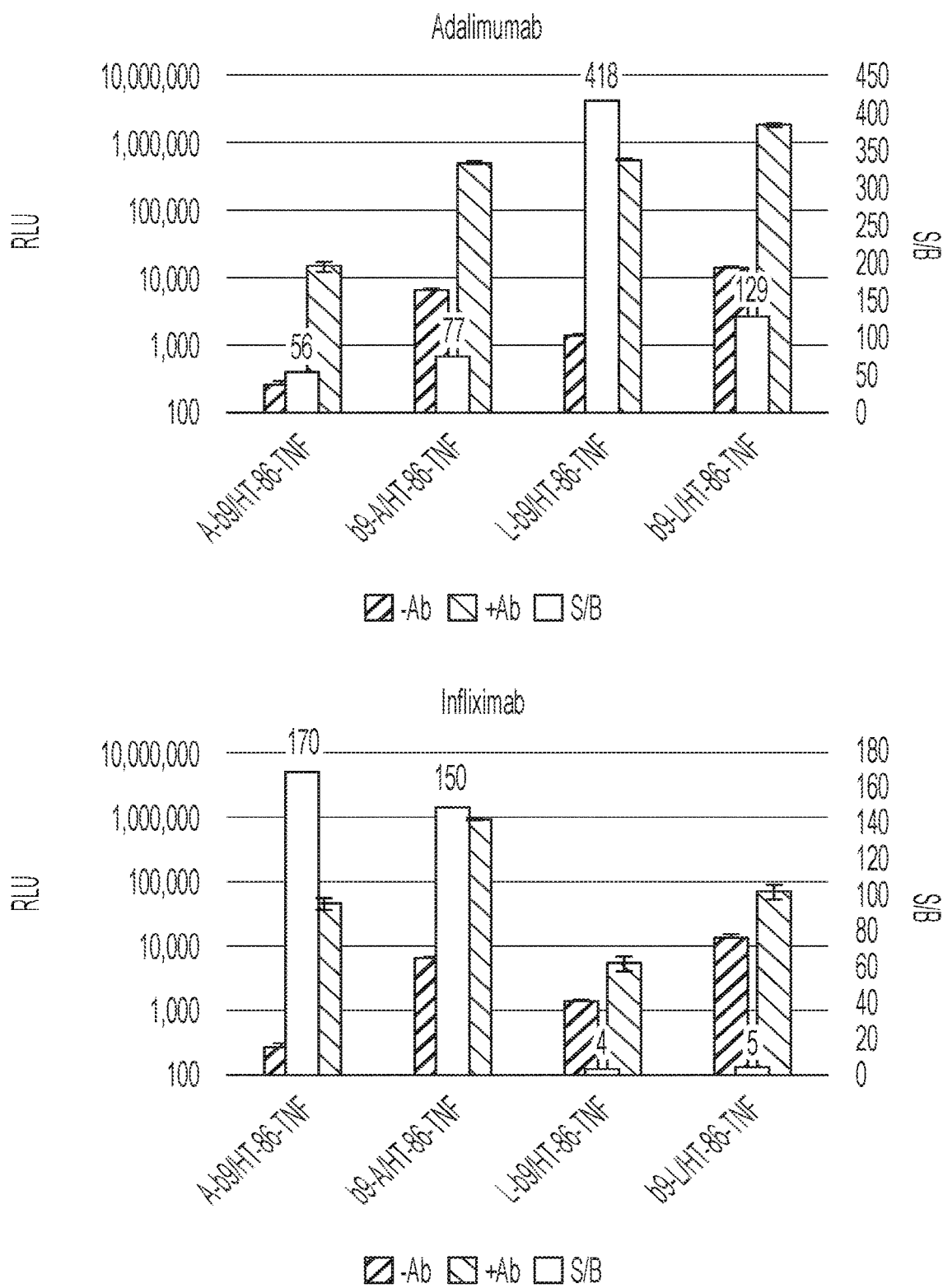
FIG. 34 is a bar chart showing both luminescence and the signal-to-background ratio for various split enzyme reporter systems.

A lysate of HaloTag®-β10*-TNF was tested combination with β9 at the N- and C-terminus of Protein A and Protein L. The luminescence in the absence of antibody (−Ab) or presence of 10 µg/mL antibody (+Ab) is shown (FIG. 34; left y-axis) as well as the signal-to-background ratio (FIG. 34; +Ab signal divided by −Ab signal; right y-axis). Values shown are the averages from three replicate measurement±standard deviation.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Each of the references cited herein is hereby incorporated by reference in its entirety. Further, reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:

1. A kit comprising for detecting an analyte in a mixture, the kit comprising:
   a first agent comprising a first targeting domain for binding to the analyte and a first peptide fragment of a split reporter protein;
   a second agent comprising a second targeting domain for binding to the analyte and a second peptide fragment of the split reporter protein;
   a third agent comprising a third fragment of the split reporter protein;
   wherein the first targeting domain is configured to selectively bind to a first target region of the analyte and the second targeting domain is configured to selectively bind to a second target region of the analyte, and the first and second target regions of the analyte are different from one another; and
   wherein the third agent is configured to bind to the first and second agents to form an active reporter complex.

2. The kit of claim 1, wherein the first peptide fragment has a mass of less than 3 kDa.

3. The kit of claim 1, wherein the second peptide fragment has a mass of less than 3 kDa.

4. The kit of claim 1, wherein the first targeting domain and the second targeting domain are each independently selected from the group consisting of an antibody, a designed ankyrin repeat protein, an affibody, a monobody, and an aptamer, or portions thereof.

5. The kit of claim 4, wherein at least one of the first targeting domain and the second targeting domain is an antibody or a portion thereof.

6. The kit of claim 4, wherein at least one of the first targeting domain and the second targeting domain is a fragment antigen binding fragment (Fab) or a single-chain variable fragment.

7. The kit of claim 4, wherein at least one of the first targeting domain and the second targeting domain is a designed ankyrin repeat protein.

8. The kit of claim 1, wherein the analyte is a monomeric protein.

9. The kit of claim 8, wherein the first target region and the second target region are different in structure.

10. The kit of claim 8, wherein the first target region and the second target region are substantially identical in structure, but are located at separate sites on the monomeric protein.

11. The kit of claim 1, wherein the analyte is a multimeric protein complex.

12. The kit of claim 11, wherein the first targeting domain and the second targeting domain bind to adjacent proteins of the multimeric protein complex.

13. The kit of claim 11, wherein the multimeric protein complex is a homomultimeric protein complex.

14. The kit of claim 11, wherein the multimeric protein complex is a heteromultimeric protein complex.

15. The kit of claim 1, wherein the first target region and the second target region are separated by less than 300 angstroms.

16. The kit of claim 1, wherein the split reporter protein is a beta-barrel protein.

17. The kit of claim 1, wherein the split reporter protein is a split enzyme, and wherein the kit further comprises a substrate of the split enzyme.

18. The kit of claim 17, wherein the enzymatic activity of the enzyme on the substrate results in emission of a detectable signal.

19. The kit of claim 18, wherein the split enzyme is a split luciferase, and the detectable signal is luminescence.

20. The kit of claim 17, wherein the split enzyme catalyzes the conversion of furimazine to furimamide.

21. The kit of claim 17, wherein the first peptide fragment is less than or equal to 11 amino acids in length.

22. The kit of claim 17, wherein the second peptide fragment is less than or equal to 11 amino acids in length.

23. The kit of claim 17, wherein the first peptide fragment and the second peptide fragment are each 11 amino acids in length.

24. The kit of claim 17, wherein the third peptide fragment has a mass of between 16 kDa and 17 kDa.

25. The kit of claim 1, wherein the split reporter protein is a split fluorescent protein.

26. The kit of claim 25, wherein the split fluorescent protein is a split green fluorescent protein.

27. The kit of claim 1, wherein one or both of the first agent and the second agent are recombinant fusion proteins.

28. The kit of claim 1, wherein the first agent, the second agent, and the third agent are configured to combine to form a non-covalent complex of the split reporter protein.

* * * * *

SEQUENCE LISTING

```
Sequence total quantity: 96
SEQ ID NO: 1            moltype = AA  length = 11
FEATURE                 Location/Qualifiers
REGION                  1..11
                        note = synthetic polypeptide
source                  1..11
                        mol_type = protein
                        organism = synthetic construct
SEQUENCE: 1
VSGWRLFKKI S                                                                  11

SEQ ID NO: 2            moltype = AA  length = 11
FEATURE                 Location/Qualifiers
REGION                  1..11
                        note = synthetic polypeptide
```

```
source                      1..11
                            mol_type = protein
                            organism = synthetic construct
SEQUENCE: 2
GSMLFRVTIN S                                                                    11

SEQ ID NO: 3                moltype = AA  length = 148
FEATURE                     Location/Qualifiers
REGION                      1..148
                            note = synthetic polypeptide
source                      1..148
                            mol_type = protein
                            organism = synthetic construct
SEQUENCE: 3
MVFTLEDFVG DWEQTAAYNL DQVLEQGGVS SLLQNLAVSV TPIQRIVRSG ENALKIDIHV    60
IIPYEGLSAD QMAQIEEVFK VVYPVDDHHF KVILPYGTLV IDGVTPNMLN YFGRPYEGIA   120
VFDGKKITVT GTLWNGNKII DERLITPD                                      148

SEQ ID NO: 4                moltype = AA  length = 18
FEATURE                     Location/Qualifiers
REGION                      1..18
                            note = synthetic polypeptide
source                      1..18
                            mol_type = protein
                            organism = synthetic construct
SEQUENCE: 4
GGGSGHHHHH HHHGGGSG                                                              18

SEQ ID NO: 5                moltype = DNA  length = 1549
FEATURE                     Location/Qualifiers
misc_feature                1..1549
                            note = beta-9-L73J (light chain) nucleotide sequence
source                      1..1549
                            mol_type = other DNA
                            organism = synthetic construct
SEQUENCE: 5
atgggtagta tgctgtttcg tgttaccatt aacagcggtg gtggtagcgg tcatcatcac    60
caccatcacc atcatggtgg tggcagtggt atggcaagcg atattcagat gacccagagc   120
ccgagcagcc tgagcgcaag cgttggtgat cgtgttacca ttacctgtcg tgcaagccag   180
agcgttagca gcgcggttgc atggtatcag cagaaaccgg gtaaagcacc gaaactgctg   240
atttatagcg caagcagcct gtatagcggt gttccgagcc gttttagcgg tagccgtagc   300
ggcaccgatt ttaccctgac cattagcagc ctgcagccgg aagattttgc aacctattat   360
tgtcagcagg gctattatta cccgtttacc tttggtcagg gcaccaaagt tgaaattaaa   420
cgtaccgttg cagcaccgag cgttttttatc tttccgccta gcgatagcca gctgaaaagc   480
ggtacagcca gcgttgtttg tctgctgaat aactttttatc gcgtgaagc aaaagttcag   540
tggaaagttg ataatgcact gcagagcggt aatagccaag aaagcgttac cgaacaggat   600
agcaaagata gcacctatag cctgagcagc acctgaccc tgaccaaaagc agattatgaa   660
aaacacaaag tgtatgcctg cgaagttacc catcagggtc tgagcagtcc ggttaccaaa   720
agctttaatc gtggtgaatg ttaattaact cgaggctgag caaagcagac tactaataac   780
ataaagtcta cgccggacgc atcgtggccc tagtacgcaa gttcacgtaa aaagggtaac   840
tagaggttga ggtgattttta tggaaattag cgaagttcag ctggttgaaa acgggttggtg   900
tctggttcag cctggtggta gcctgcgtct gagctgtgca gcaagcggtt ttaatctgta  960
tagcagctat attcattggg ttcgtcaggc accgggtaaa ggtctggaat gggttgcaag  1020
catttatccg tatagctcat ataccagcta tgccgatagc gttaaaggtc gttttaccat  1080
tagccgcagat accagcaaaa ataccgcata cctgcagatg aatagtctgc gtgcagagga  1140
taccgcagtg tattattgtg cacgttatta tggtttcgcc atggattatt ggggtcaggg  1200
caccctggtt accgttagca gcgcaagcac caaaggtccg agcgttttttc cgctggcacc  1260
gagcagcaaa agcaccagcg gtggcaccgc agcactgggt tgtctggtta agatattttt  1320
tccggaaccg gttaccgtga gctggaatag cggtgcactg accagtggtg ttcataccctt  1380
tccggcagtt ctgcagagca gcggtctgta tagtctgagc agcgttgtta ccgttccgag  1440
cagtagcctg ggcacccaga cctatatttg taatgttaat cataaaccga gcaacaccaa  1500
agtggataaa aaagttgaac cgaaaagctg cgataaaacc catacctaa                  1549

SEQ ID NO: 6                moltype = AA  length = 247
FEATURE                     Location/Qualifiers
REGION                      1..247
                            note = Beta9-His Tag-light chain
source                      1..247
                            mol_type = protein
                            organism = synthetic construct
SEQUENCE: 6
MGSMLFRVTI NSGGGSGHHH HHHHGGGSG MASDIQMTQS PSSLSASVGD RVTITCRASQ     60
SVSSAVAWYQ QKPGKAPKLL IYSASSLYSG VPSRFSGSRS GTDFTLTISS LQPEDFATYY   120
CQQGYYYPFT FGQGTKVEIK RTVAAPSVFI FPPSDSQLKS GTASVVCLLN NFYPREAKVQ   180
WKVDNALQSG NSQESVTEQD SKDSTYSLSS TLTLSKADYE KHKVYACEVT HQGLSSPVTK   240
SFNRGEC                                                             247

SEQ ID NO: 7                moltype = AA  length = 229
FEATURE                     Location/Qualifiers
```

-continued

```
REGION                    1..229
                          note = heavy chain
source                    1..229
                          mol_type = protein
                          organism = synthetic construct
SEQUENCE: 7
MEISEVQLVE SGGGLVQPGG SLRLSCAASG FNLYSSYIHW VRQAPGKGLE WVASIYPYSS      60
YTSYADSVKG RFTISADTSK NTAYLQMNSL RAEDTAVYYC ARYYGFAMDY WGQGTLVTVS     120
SASTKGPSVF PLAPSSKSTS GGTAALGCLV KDYFPEPVTV SWNSGALTSG VHTFPAVLQS     180
SGLYSLSSVV TVPSSSLGTQ TYICNVNHKP SNTKVDKKVE PKSCDKTHT                 229

SEQ ID NO: 8              moltype = DNA  length = 1549
FEATURE                   Location/Qualifiers
misc_feature              1..1549
                          note = Beta10*-L73J
source                    1..1549
                          mol_type = other DNA
                          organism = synthetic construct
SEQUENCE: 8
atggtgagcg gttggcgtct gttcaaaaaa atcagcggtg gtggtagcgg tcatcatcac      60
caccatcacc atcatggtgg tggcagtggt atggcaagcg atattcagat gacccagagc     120
ccgagcagcc tgagcgcaag cgttggcgat cgtgttacca ttacctgtcg tgcaagccag     180
agcgttagca gcgcggttgc atggtatcag cagaaaccgg gtaaagcacc gaaactgctg     240
atttatagcg caagcagcct gtatagcggt gttccgagcc gttttagcgg tagccgtagc     300
ggcaccgatt ttacccctgac cattagcagc ctgcagccgg aagattttgc aacctattat     360
tgtcagcagg gctattatta cccgtttacc tttggtcagg gcaccaaagt tgaaattaaa     420
cgtaccgttg cagcaccgag cgtttttatc tttccgccta gcgatagcca gctgaaaagc     480
ggtacagcca gcgttgtttg tctgctgaat aacttttatc cgcgtgaagc aaaagttcag     540
tggaaagttg ataatgcact gcagagcggt aatagccaag aaagcgttac cgaacaggat     600
agcaaagata gcacctatag cctgagcagc acccctgaccc tgagcaaagc agattatgaa     660
aaacacaaag tgtatgcctg cgaagttacc catcagggtc tgagcagtcc ggttaccaaa     720
agctttaatc gtggtgaatg ttaattaact cgaggctgag caaagcagac tactaataac     780
ataaagtcta cgccggacgc atcgtggccc tagtacgcaa gttcacgtaa aaagggtaac     840
tagaggttga ggtgattta tggaaattag cgaagttcga acctggtgaaa gcggtggtgg     900
tctggttcag cctggtggta gcctgcgtct gagctgtgca gcaagcggtt ttaatctgta     960
tagcagctat attcattggg ttcgtcaggc accgggtaaa ggtctggaat gggttgcaag    1020
catttatccg tatagctcat ataccagcta tgccgatagc gttaaggtc gttttaccat    1080
tagcgcagat accagcaaaa ataccgcata cctgcagatg aatagtctgc gtgcagagga    1140
taccgcagtg tattattgtg cacgttatta tggtttcgc atggattatt gggtcagggg    1200
caccctggtt accgttagca gcgcaagcac caaaggtccg agcgttttc gctggcacc    1260
gagcagcaaa agcaccagcg gtggcaccgc agcactgggt tgtctggtta agattattt    1320
tccgaaccg gttaccgtga gctggaatag cggtgcactg accagtggtg ttcatacctt    1380
tccggcagtt ctgcagagca gcggtctgta tagtctgagc agcgttgtta ccgttccgag    1440
cagtagcctg ggcacccaga cctatatttg taatgttaat cataaaccga gcaacaccaa    1500
agtggataaa aaagttgaac cgaaaagctg cgataaaacc cataccctaa                1549

SEQ ID NO: 9              moltype = AA  length = 247
FEATURE                   Location/Qualifiers
REGION                    1..247
                          note = Beta10*-His Tag-light chain
source                    1..247
                          mol_type = protein
                          organism = synthetic construct
SEQUENCE: 9
MVSGWRLFKK ISGGGSGHHH HHHHGGGSG MASDIQMTQS PSSLSASVGD RVTITCRASQ       60
SVSSAVAWYQ QKPGKAPKLL IYSASSLYSG VPSRFSGSRS GTDFTLTISS LQPEDFATYY     120
CQQGYYYPFT FGQGTKVEIK RTVAAPSVFI FPPSDSQLKS GTASVVCLLN NFYPREAKVQ     180
WKVDNALQSG NSQESVTEQD SKDSTYSLSS TLTLSKADYE KHKVYACEVT HQGLSSPVTK     240
SFNRGEC                                                              247

SEQ ID NO: 10             moltype = AA  length = 229
FEATURE                   Location/Qualifiers
REGION                    1..229
                          note = heavy chain
source                    1..229
                          mol_type = protein
                          organism = synthetic construct
SEQUENCE: 10
MEISEVQLVE SGGGLVQPGG SLRLSCAASG FNLYSSYIHW VRQAPGKGLE WVASIYPYSS      60
YTSYADSVKG RFTISADTSK NTAYLQMNSL RAEDTAVYYC ARYYGFAMDY WGQGTLVTVS     120
SASTKGPSVF PLAPSSKSTS GGTAALGCLV KDYFPEPVTV SWNSGALTSG VHTFPAVLQS     180
SGLYSLSSVV TVPSSSLGTQ TYICNVNHKP SNTKVDKKVE PKSCDKTHT                 229

SEQ ID NO: 11             moltype = DNA  length = 1546
FEATURE                   Location/Qualifiers
misc_feature              1..1546
                          note = 73JH-Beta9
source                    1..1546
                          mol_type = other DNA
```

```
                        organism = synthetic construct
SEQUENCE: 11
atggcaagcg atattcagat gacccagagc ccgagcagcc tgagcgcaag cgttggtgat    60
cgtgttacca ttacctgtcg tgcaagccag agcgttagca gcgcggttgc atggtatcag   120
cagaaaccgg gtaaagcacc gaaactgctg atttatagcg caagcagcct gtatagcggt   180
gttccgagcc gttttagcgg tagccgtagc ggcaccgatt ttaccctgac cattagcagc   240
ctgcagccga agatttttgc aacctattat tgtcagcagg gctattatta cccgtttacc   300
tttggtcagg gcaccaaagt tgaaattaaa cgtaccgttg cagcaccgag cgttttttatc   360
tttccgccta gcgatagcca gctgaaaagc ggtacagcca gcgttgtttg tctgctgaat   420
aactttatc cgcgtgaagc aaaagttcag tggaaagttg ataatgcact gcagagcggt   480
aatagccaag aaagcgttac cgaacaggat agcaaagata gcacctatag cctgagcagc   540
accctgaccc tgagcaaagc agattatgaa aaacacaaag tgtatgcctg cgaagttacc   600
catcagggtc tgagcagtcc ggttaccaaa agctttaatc gtggtgaatg ttaattaact   660
cgaggctgag caaagcagac tactaataac ataaagtcta cgccggacgc atcgtggccc   720
tagtacgcaa gttcacgtaa aaagggtaac tagaggttga ggtgatttta tggaaattag   780
cgaagttcag ctggttgaaa gcggtggtgg tctggttcag cctggtggta gcctgcgtct   840
gagctgtgca gcaagcggtt ttaatctgta tagcagctat attcattggg ttcgtcaggc   900
accgggtaaa ggtctggaat gggttgcaag catttatccg tatagctcat ataccagcta   960
tgccgatagc gttaaaggtc gttttaccat tagcgcagat accagcaaaa ataccgcata  1020
cctgcagatg aatagtctgc gtgcagagga taccgcagtg tattattgtg cacgttatta  1080
tggtttcgcc atggattatt ggggtcaggg caccctggtt accgttagca gcgcaagcac  1140
caaaggtccg agcgtttttc cgctggcacc gagcagcaaa agcaccagcg gtggcaccgc  1200
agcactgggt tgtctggtta agattattt ccggaaccg gttaccgtga gctggaatag  1260
cggtgcactg accagtggtg ttcatacctt tccggcagtt ctgcagagca gcggtctgta  1320
tagtctgagc agcgttgtta ccgttccgag cagtagcctg gcacccaga cctatatttg  1380
taatgttaat cataaaccga gcaacaccaa agtggataaa aaagttgaac cgaaaagctg  1440
cgataaaacc cataccggtg gtggtagcgg tcatcatcac caccatcacc atcatggtgg  1500
tggcagtggt ggtagtatgc tgtttcgtgt taccattaac agctaa              1546

SEQ ID NO: 12           moltype = AA  length = 217
FEATURE                 Location/Qualifiers
REGION                  1..217
                        note = light chain
source                  1..217
                        mol_type = protein
                        organism = synthetic construct
SEQUENCE: 12
MASDIQMTQS PSSLSASVGD RVTITCRASQ SVSSAVAWYQ QKPGKAPKLL IYSASSLYSG    60
VPSRFSGSRS GTDFTLTISS LQPEDFATYY CQQGYYYPFT FGQGTKVEIK RTVAAPSVFI   120
FPPSDSQLKS GTASVVCLLN NFYPREAKVQ WKVDNALQSG NSQESVTEQD SKDSTYSLSS   180
TLTLSKADYE KHKVYACEVT HQGLSSPVTK SFNRGEC                            217

SEQ ID NO: 13           moltype = AA  length = 258
FEATURE                 Location/Qualifiers
REGION                  1..258
                        note = heavy chain-His Tag-Beta9
source                  1..258
                        mol_type = protein
                        organism = synthetic construct
SEQUENCE: 13
MEISEVQLVE SGGGLVQPGG SLRLSCAASG FNLYSSYIHW VRQAPGKGLE WVASIYPYSS    60
YTSYADSVKG RFTISADTSK NTAYLQMNSL RAEDTAVYYC ARYYGFAMDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTG GGSGHHHHHH   240
HHGGGSGGSM LFRVTINS                                                 258

SEQ ID NO: 14           moltype = DNA  length = 1546
FEATURE                 Location/Qualifiers
misc_feature            1..1546
                        note = 73JH-Beta10*
source                  1..1546
                        mol_type = other DNA
                        organism = synthetic construct
SEQUENCE: 14
atggcaagcg atattcagat gacccagagc ccgagcagcc tgagcgcaag cgttggtgat    60
cgtgttacca ttacctgtcg tgcaagccag agcgttagca gcgcggttgc atggtatcag   120
cagaaaccgg gtaaagcacc gaaactgctg atttatagcg caagcagcct gtatagcggt   180
gttccgagcc gttttagcgg tagccgtagc ggcaccgatt ttaccctgac cattagcagc   240
ctgcagccgg aagatttttgc aacctattat tgtcagcagg gctattatta cccgtttacc   300
tttggtcagg gcaccaaagt tgaaattaaa cgtaccgttg cagcaccgag cgttttttatc   360
tttccgccta gcgatagcca gctgaaaagc ggtacagcca gcgttgtttg tctgctgaat   420
aactttatc cgcgtgaagc aaaagttcag tggaaagttg ataatgcact gcagagcggt   480
aatagccaag aaagcgttac cgaacaggat agcaaagata gcacctatag cctgagcagc   540
accctgaccc tgagcaaagc agattatgaa aaacacaaag tgtatgcctg cgaagttacc   600
catcagggtc tgagcagtcc ggttaccaaa agctttaatc gtggtgaatg ttaattaact   660
cgaggctgag caaagcagac tactaataac ataaagtcta cgccggacgc atcgtggccc   720
tagtacgcaa gttcacgtaa aaagggtaac tagaggttga ggtgatttta tggaaattag   780
cgaagttcag ctggttgaaa gcggtggtgg tctggttcag cctggtggta gcctgcgtct   840
gagctgtgca gcaagcggtt ttaatctgta tagcagctat attcattggg ttcgtcaggc   900
```

```
accgggtaaa ggtctggaat gggttgcaag catttatccg tatagctcat ataccagcta   960
tgccgatagc gttaaaggtc gttttaccat tagcgcagat accagcaaaa ataccgcata  1020
cctgcagatg aatagtctgc gtgcagagga taccgcagtg tattattgtg cacgttatta  1080
tggtttcgcc atggattatt ggggtcaggg caccctggtt accgttagca gcgcaagcac  1140
caaaggtccg agcgtttttc cgctggcacc gagcagcaaa agcaccagcg gtggcaccgc  1200
agcactgggt tgtctggtta aagattattt tccggaaccg gttaccgtga gctggaatag  1260
cggtgcactg accagtggtg ttcatacctt tccggcagtt ctgcagagca gcggtctgta  1320
tagtctgagc agcgttgtta ccgttccgag cagtagcctg gcacccaga cctatatttg  1380
taatgttaat cataaaccga gcaacaccaa agtggataaa aaagttgaac cgaaaagctg  1440
cgataaaacc cataccggtg gtggtagcgg tcatcatcac caccatcacc atcatggtgg  1500
tggcagtggt gtgagcggtg ggcgtctgtt caaaaaaatc agctaa             1546

SEQ ID NO: 15          moltype = AA   length = 217
FEATURE                Location/Qualifiers
REGION                 1..217
                       note = light chain
source                 1..217
                       mol_type = protein
                       organism = synthetic construct
SEQUENCE: 15
MASDIQMTQS PSSLSASVGD RVTITCRASQ SVSSAVAWYQ QKPGKAPKLL IYSASSLYSG    60
VPSRFSGSRS GTDFTLTISS LQPEDFATYY CQQGYYYPFT FGQGTKVEIK RTVAAPSVFI   120
FPPSDSQLKS GTASVVCLLN NFYPREAKVQ WKVDNALQSG NSQESVTEQD SKDSTYSLSS   180
TLTLSKADYE KHKVYACEVT HQGLSSPVTK SFNRGEC                            217

SEQ ID NO: 16          moltype = AA   length = 258
FEATURE                Location/Qualifiers
REGION                 1..258
                       note = heavy chain-HisTag-Beta9
source                 1..258
                       mol_type = protein
                       organism = synthetic construct
SEQUENCE: 16
MEISEVQLVE SGGGLVQPGG SLRLSCAASG FNLYSSYIHW VRQAPGKGLE WVASIYPYSS    60
YTSYADSVKG RFTISADTSK NTAYLQMNSL RAEDTAVYYC ARYYGFAMDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTG GGSGHHHHHH   240
HHGGGSGVSG WRLFKKIS                                                 258

SEQ ID NO: 17          moltype = DNA   length = 1555
FEATURE                Location/Qualifiers
misc_feature           1..1555
                       note = Beta9-HTras
source                 1..1555
                       mol_type = other DNA
                       organism = synthetic construct
SEQUENCE: 17
atggcaagcg atattcagat gacccagagc ccgagcagcc tgagcgcaag cgttggtgat    60
cgtgttacca ttacctgtcg tgcaagccag gatgttaata ccgcagttgc atggtatcag   120
cagaaaccgg gtaaagcacc gaaactgctg atttatagcg caagctttct gtatagcggt   180
gttccgagcc gttttagcgg tagccgtagc ggcaccgatt ttaccctgac cattagcagc   240
ctgcagccgg aagattttgc aacctattat tgtcagcagc attacaccac ccctccgacc   300
tttggtcagg gcaccaaagt tgaaattaaa cgtaccgttg cagcaccgag cgtttttatc   360
tttccgccta gcgatgagca gctgaaaagc ggtacagcca gcgttgtttg tctgctgaat   420
aactttatc cgcgtgaagc aaaagttcag tggaaagttg ataatgcact gcagagccgt   480
aatagccaag aaagcgttac gaacaggat agcaaagata gcacctatag cctgagcagc   540
accctgaccc tgagcaaagc agattatgaa aaacacaaag tgtatgcctg cgaagttacc   600
catcagggtc tgagcagtcc ggttaccaaa agctttaatc gtggtgaatg ttaattaact   660
cgaggctgag caaagcagac tactaataac ataaagtcta cgccggacgc atcgtggccc   720
tagtacgcaa gttcacgtaa aaagggtaac tagaggttga ggtgattttta tgggtagtat   780
gctgtttcgt gttaccatta acagcggtgg tggtagcggt catcatcacc accatcacca   840
tcatggtggt ggcagtggtg aaattagcga agttcagctg gttaaagcg gtggtggtct   900
ggttcagcct ggtggtagcc tgcgtctgag ctgtgcagca agcggttta acattaaaga   960
tacctatatc cactgggttc gtcaggcacc gggtaaaggt ctggaatggg ttgcacgtat  1020
ttatccgacc aatggttata ccgttatgc cgatagcgtt aaaggtcgtt ttaccattag  1080
cgcagatacc agcaaaaata ccgcatacct gcagatgaat agtctgcgtg cagaggatac  1140
cgcagtgtat tattgtagcc gttggggtgg tgatggtttt tatgcaatgg attattgggg  1200
tcagggcacc ctggttaccg ttagcagcgc aagcaccaaa ggtccgagcg ttttttccgct  1260
ggcaccggca agcaaaagca cagcggtgg caccgcagca ctggggttaaga  1320
ttattttccg gaaccggtta ccgtgagctg gaatagcggt gcactgacca gtggtgttca  1380
tacctttccg gcagttctgc agagcagcgg tctgtatagt ctgagcagcg ttgttaccgt  1440
tccgagcagt agcctgggca cccagaccta tatttgtaat gttaatcata aaccgagcaa  1500
caccaaagtg gataaaaag ttgaaccgaa agctgcgat aaaacccata cctaa         1555

SEQ ID NO: 18          moltype = AA   length = 217
FEATURE                Location/Qualifiers
REGION                 1..217
                       note = light chain
source                 1..217
```

```
                            mol_type = protein
                            organism = synthetic construct
SEQUENCE: 18
MASDIQMTQS PSSLSASVGD RVTITCRASQ DVNTAVAWYQ QKPGKAPKLL IYSASFLYSG        60
VPSRFSGSRS GTDFTLTISS LQPEDFATYY CQQHYTTPPT FGQGTKVEIK RTVAAPSVFI       120
FPPSDEQLKS GTASVVCLLN NFYPREAKVQ WKVDNALQSG NSQESVTEQD SKDSTYSLSS       180
TLTLSKADYE KHKVYACEVT HQGLSSPVTK SFNRGEC                                217

SEQ ID NO: 19              moltype = AA  length = 261
FEATURE                    Location/Qualifiers
REGION                     1..261
                           note = Beta9-His Tag-heavy chain
source                     1..261
                           mol_type = protein
                           organism = synthetic construct
SEQUENCE: 19
MGSMLFRVTI NSGGGSGHHH HHHHHGGGSG EISEVQLVES GGGLVQPGGS LRLSCAASGF        60
NIKDTYIHWV RQAPGKGLEW VARIYPTNGY TRYADSVKGR FTISADTSKN TAYLQMNSLR       120
AEDTAVYYCS RWGGDGFYAM DYWGQGTLVT VSSASTKGPS VFPLAPSSKS TSGGTAALGC       180
LVKDYFPEPV TVSWNSGALT SGVHTFPAVL QSSGLYSLSS VVTVPSSSLG TQTYICNVNH       240
KPSNTKVDKK VEPKSCDKTH T                                                 261

SEQ ID NO: 20              moltype = DNA  length = 1555
FEATURE                    Location/Qualifiers
misc_feature               1..1555
                           note = Beta10*-HTras
source                     1..1555
                           mol_type = other DNA
                           organism = synthetic construct
SEQUENCE: 20
atggcaagcg atattcagat gacccagagc ccgagcagcc tgagcgcaag cgttggtgat        60
cgtgttacca ttacctgtcg tgcaagccag gatgttaata ccgcagttgc atggtatcag       120
cagaaaccgg gtaaagcacc gaaactgctg atttatagcg caagctttct gtatagcggt       180
gttccgagcc gttttagcgg tagccgtagc ggcaccgatt ttacccttac cattagcagc       240
ctgcagccgg aagattttgc aacctattat tgtcagcagc attacaccac ccctccgacc       300
tttggtcagg gcaccaaagt tgaaattaaa cgtaccgttg cagcaccgag cgttttttatc      360
tttccgccta gcgatgagca gctgaaaagc ggtacagcca gcgttgtttg tctgctgaat       420
aacttttatc cgcgtgaagc aaaagttcag tggaaagttg ataatgcact gcagagcggt       480
aatagccaag aaaagcgttac cgaacaggat agcaaagata gcacctatag cctgagcagc       540
accctgaccc tgagcaaagc agattatgaa aaacacaaag tgtatgcctg cgaagttacc       600
catcagggtc tgagcagtcc ggttaccaaa agctttaatc gtggtgaatg ttaattaact       660
cgaggctgag caaagcagac tactaataac ataaagtcta cgccggacgc atcgtggccc       720
tagtacgcaa gttcacgtaa aaagggtaac tagaggttga ggtgattta tggtgagcgg       780
ttggcgtctg ttcaaaaaaa tcagcggtgg tggtagcggt catcatcacc accatcacca       840
tcatggtggt ggcagtggtg aaattagcga agttcagctg gttgaaagcg gtggtggtct       900
ggttcagcct ggtggtagcc tgcgtctgag ctgtgcagca agcggtttta acattaaaga       960
tacctatatc cactgggttc gtcaggcacc gggtaaaggt ctggaatggg ttgcacgtat      1020
ttatccgacc aatggttata cccgttatgc cgatagcgtt aaaggtcgtt ttaccattag      1080
cgcagatacc agcaaaaata ccgcataacct gcagatgaat agtctgcctg cagaggatac      1140
cgcagtgtat tattgtagcc gttggggtgg tgatggtttt tatgcaatgg attattgggg      1200
tcagggaacc ctggttaccg ttagcagcgc aagcaccaaa ggtccgagcg ttttttccgct      1260
ggcaccgagc agcaaaagca ccagcggtgg caccgcagca ctgggttgtc tggttaaaga      1320
ttatttttccg gaaccggtta ccgtgagctg gaatagcggt gcactgacca gtggtgttca      1380
tacctttccg gcagttctgc agagcagcgg tctgtatagt ctgagcagcg ttgttaccgt      1440
tccgagcagt agcctgggca cccagaccta tatttgtaat gttaatcata aaccgagcaa      1500
caccaaagtg gataaaaaag ttgaaccgaa aagctgcgat aaaacccata cctaa          1555

SEQ ID NO: 21              moltype = AA  length = 217
FEATURE                    Location/Qualifiers
REGION                     1..217
                           note = light chain
source                     1..217
                           mol_type = protein
                           organism = synthetic construct
SEQUENCE: 21
MASDIQMTQS PSSLSASVGD RVTITCRASQ DVNTAVAWYQ QKPGKAPKLL IYSASFLYSG        60
VPSRFSGSRS GTDFTLTISS LQPEDFATYY CQQHYTTPPT FGQGTKVEIK RTVAAPSVFI       120
FPPSDEQLKS GTASVVCLLN NFYPREAKVQ WKVDNALQSG NSQESVTEQD SKDSTYSLSS       180
TLTLSKADYE KHKVYACEVT HQGLSSPVTK SFNRGEC                                217

SEQ ID NO: 22              moltype = AA  length = 261
FEATURE                    Location/Qualifiers
REGION                     1..261
                           note = Beta10*-His Tag-heavy chain
source                     1..261
                           mol_type = protein
                           organism = synthetic construct
SEQUENCE: 22
MVSGWRLFKK ISGGGSGHHH HHHHHGGGSG EISEVQLVES GGGLVQPGGS LRLSCAASGF        60
```

NIKDTYIHWV RQAPGKGLEW VARIYPTNGY TRYADSVKGR FTISADTSKN TAYLQMNSLR 120
AEDTAVYYCS RWGGDGFYAM DYWGQGTLVT VSSASTKGPS VFPLAPSSKS TSGGTAALGC 180
LVKDYFPEPV TVSWNSGALT SGVHTFPAVL QSSGLYSLSS VVTVPSSSLG TQTYICNVNH 240
KPSNTKVDKK VEPKSCDKTH T 261

```
SEQ ID NO: 23            moltype = DNA   length = 1555
FEATURE                  Location/Qualifiers
misc_feature             1..1555
                         note = TrasH-Beta9
source                   1..1555
                         mol_type = other DNA
                         organism = synthetic construct
SEQUENCE: 23
```
atggcaagcg atattcagat gacccagagc ccgagcagcc tgagcgcaag cgttggtgat 60
cgtgttacca ttacctgtcg tgcaagccag gatgttaata ccgcagttgc atggtatcag 120
cagaaaccgg gtaaagcacc gaaactgctg atttatagcg caagcttcct gtatagcggt 180
gttccgagcc gttttagcgg tagccgtagc ggcaccgatt ttaccctgac cattagcagc 240
ctgcagccgg aagattttgc aacctattat tgtcagcagc attacaccac ccctccgacc 300
tttggtcagg gcaccaaagt tgaaattaaa cgtaccgttg cagcaccgag cgttttttatc 360
tttccgccta gcgatgagca gctgaaaagc ggtacagcca gcgttgtttg tctgctgaat 420
aacttttatc cgcgtgaagc aaaagttcag tggaaagttg ataatgcact gcagagcggt 480
aatagccaag aaaagcgttac cgaacaggat agcaaagata cacctatag cctgagcagc 540
accctgaccc tgagcaaagc agattatgaa aaacacaaag tgtatgcctg cgaagttacc 600
catcagggtc tgagcagtcc ggttaccaaa agctttaatc gtggtgaatg ttaattaact 660
cgaggctgag caaagcagac tactaataac ataaagtcta cgccggacgc atcgtggccc 720
tagtacgcaa gttcacgtaa aaagggtaac tagaggttga ggtgatttta tggaaattag 780
cgaagttcag ctggttgaaa gcggtggtgg tctggttcag cctggtggta gcctgcgtct 840
gagctgtgca gcaagcggtt ttaacattaa agataccttat atccactggg ttcgtcaggc 900
accgggtaaa ggtctggaat gggttgcacg tatttatccg accaatggtt ataccgttta 960
tgccgatagc gttaaaggtc gttttaccat tagcgcagat accagcaaaa ataccgcata 1020
cctgcagatg aatagtctgc gtgcagagga taccgcagtg tattattgta gccgttgggg 1080
tggtgatggt ttttatgcaa tggattattg gggtcagggc accctggtta ccgttagcag 1140
cgcaagcacc aaaggtccga gcgttttttcc gctggcaccg agcagcaaaa gcaccagcgg 1200
tggcaccgca gcactgggtt gtctggttaa agattatttt ccggaaccgg ttaccgtgag 1260
ctggaatagc ggtgcactga ccagtggtgt tcatacctttt ccggcagttc tgcagagcag 1320
cggtctgtat agtctgagca gcgttgttac cgttccgagc agtagcctgg cacccagac 1380
ctatatttgt aatgttaatc ataaaccgag caacaccaaa gtggataaaa aagttgaacc 1440
gaaaagctgc gataaaaccc ataccggtgg tggtagcggt catcatcacc accatcacca 1500
tcatggtggt ggcagtggtg gtagtatgct gtttcgtgtt accattaaca gctaa 1555

```
SEQ ID NO: 24            moltype = AA    length = 217
FEATURE                  Location/Qualifiers
REGION                   1..217
                         note = light chain
source                   1..217
                         mol_type = protein
                         organism = synthetic construct
SEQUENCE: 24
```
MASDIQMTQS PSSLSASVGD RVTITCRASQ DVNTAVAWYQ QKPGKAPKLL IYSASFLYSG 60
VPSRFSGSRS GTDFTLTISS LQPEDFATYY CQQHYTTPPT FGQGTKVEIK RTVAAPSVFI 120
FPPSDEQLKS GTASVVCLLN NFYPREAKVQ WKVDNALQSG NSQESVTEQD SKDSTYSLSS 180
TLTLSKADYE KHKVYACEVT HQGLSSPVTK SFNRGEC 217

```
SEQ ID NO: 25            moltype = AA    length = 261
FEATURE                  Location/Qualifiers
REGION                   1..261
                         note = heavy chain-His Tag-Beta9
source                   1..261
                         mol_type = protein
                         organism = synthetic construct
SEQUENCE: 25
```
MEISEVQLVE SGGGLVQPGG SLRLSCAASG FNIKDTYIHW VRQAPGKGLE WVARIYPTNG 60
YTRYADSVKG RFTISADTSK NTAYLQMNSL RAEDTAVYYC SRWGGDGFYA MDYWGQGTLV 120
TVSSASTKGP SVFPLAPSSK STSGGTAALG CLVKDYFPEP VTVSWNSGAL TSGVHTFPAV 180
LQSSGLYSLS SVVTVPSSSL GTQTYICNVN HKPSNTKVDK KVEPKSCDKT HTGGGSGHHH 240
HHHHGGGSG GSMLFRVTIN S 261

```
SEQ ID NO: 26            moltype = DNA   length = 1555
FEATURE                  Location/Qualifiers
misc_feature             1..1555
                         note = TrasH-Beta10*
source                   1..1555
                         mol_type = other DNA
                         organism = synthetic construct
SEQUENCE: 26
```
atggcaagcg atattcagat gacccagagc ccgagcagcc tgagcgcaag cgttggtgat 60
cgtgttacca ttacctgtcg tgcaagccag gatgttaata ccgcagttgc atggtatcag 120
cagaaaccgg gtaaagcacc gaaactgctg atttatagcg caagcttcct gtatagcggt 180
gttccgagcc gttttagcgg tagccgtagc ggcaccgatt ttaccctgac cattagcagc 240

```
ctgcagccgg aagatttttgc aacctattat tgtcagcagc attacaccac ccctccgacc   300
tttggtcagg gcaccaaagt tgaaattaaa cgtaccgttg cagcaccgag cgttttttatc   360
tttccgccta cgcgatgagca gctgaaaagc ggtacagcca gcgttgtttg tctgctgaat   420
aacttttatc cgcgtgaagc aaaagttcag tggaaagttg ataatgcact gcagagcggt   480
aatgccaag aaagcgttac cgaacaggat agcaaagata gcacctatag cctgagcagc   540
accctgaccc tgagcaaagc agattatgaa aaacacaaag tgtatgcctg cgaagttacc   600
catcagggtc tgagcagtcc ggttaccaaa agctttaatc gtggtgaatg ttaattaact   660
cgaggctgag caaagcagac tactaataac ataaagtcta cgccggacgc atcgtggccc   720
tagtacgcaa gttcacgtaa aaagggtaac tagaggttga ggtgattta tggaaattag   780
cgaagttcag ctggttgaaa gcggtggtgg tctgttcag cctggtggta gcctgcgtct   840
gagctgtgca gcaagcggtt taacattaa agatacctat atccactggg ttcgtcaggc   900
accgggtaaa ggtctggaat gggttgcacg tatttatccg accaatggtt atacccgtta   960
tgccgatagc gttaaaggtc gttttaccat tagcgcagat accagcaaaa ataccgcata  1020
cctgcagatg aatagtctgc gtgcagagga taccgcagtg tattattgta gccgttgggg  1080
tggtgatggt ttttatgcaa tggattattg gggtcagggc accctggtta ccgttagcag  1140
cgcaagcacc aaaggtccga cgttttttcc gctggcaccg agcagcaaaa gcaccagcgg  1200
tggcaccgca gcactgggtt gtctggttaa agattatttt ccggaaccgg ttaccgtgag  1260
ctggaatagc ggtgcactga ccagtggtgt tcataccttc ccggcagttc tgcagagcag  1320
cggtctgtat agtctgagca gcgttgttac cgttccgagc agtagcctgg caccccagac  1380
ctatatttgt aatgttaatc ataaaccgag caacaccaaa gtgggataaaa aagttgaacc  1440
gaaaagctgc gataaaaccc ataccggtgg tggtagcggc catcatcacc accatcacca  1500
tcatggtggt ggcagtggtg tgagcggttg gcgtctgttc aaaaaaatca gctaa         1555

SEQ ID NO: 27          moltype = AA   length = 217
FEATURE                Location/Qualifiers
REGION                 1..217
                       note = light chain
source                 1..217
                       mol_type = protein
                       organism = synthetic construct
SEQUENCE: 27
MASDIQMTQS PSSLSASVGD RVTITCRASQ DVNTAVAWYQ QKPGKAPKLL IYSASFLYSG     60
VPSRFSGSRS GTDFTLTISS LQPEDFATYY CQQHYTTPPT FGQGTKVEIK RTVAAPSVFI   120
FPPSDEQLKS GTASVVCLLN NFYPREAKVQ WKVDNALQSG NSQESVTEQD SKDSTYSLSS   180
TLTLSKADYE KHKVYACEVT HQGLSSPVTK SFNRGEC                            217

SEQ ID NO: 28          moltype = AA   length = 261
FEATURE                Location/Qualifiers
REGION                 1..261
                       note = heavy chain-His Tag-Beta10*)
source                 1..261
                       mol_type = protein
                       organism = synthetic construct
SEQUENCE: 28
MEISEVQLVE SGGGLVQPGG SLRLSCAASG FNIKDTYIHW VRQAPGKGLE WVARIYPTNG     60
YTRYADSVKG RFTISADTSK NTAYLQMNSL RAEDTAVYYC SRWGGDGFYA MDYWGQGTLV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSNTKVDK KVEPKSCDKT HTGGGSGHHH   240
HHHHHGGSG VSGWRLFKKI S                                              261

SEQ ID NO: 29          moltype = DNA   length = 1555
FEATURE                Location/Qualifiers
misc_feature           1..1555
                       note = Beta9-LPert
source                 1..1555
                       mol_type = other DNA
                       organism = synthetic construct
SEQUENCE: 29
atgggtagta tgctgtttcg tgttaccatt aacagcggtg gtggtagcgg tcatcatcac    60
caccatcacc atcatggtgg tggcagtggt atggcaagcg atattcagat gacccagagc   120
ccgagcagcc tgagcgcaag cgttggtgat cgtgttacca ttacctgtaa ggcaagccag   180
gatgttagca ttggtgttgc atggtatcag cagaaaccgg gtaaagcacc gaaactgctg   240
atttatagcg caagctatcg ttataccggt gttccgagcc gttttagcgg tagcggcagc   300
ggcaccgatt ttaccctgac cattagcagc ctgcagccgg aagatttttgc aacctattat   360
tgtcagcagt actacatcta tccgtacacc tttggtcagg gcaccaaagt tgaaattaaa   420
cgtaccgttg cagcaccgag cgttttttatc tttccgccta cgcgatgagca gctgaaaagc   480
ggtacagcca gcgttgtttg tctgctgaat aacttttatc cgcgtgaagc aaaagttcag   540
tggaaagttg ataatgcact gcagagcggt aatagccaag aaagcgttac cgaacaggat   600
agcaaagata gcacctatag cctgagcagc accctgaccc tgagcaaagc agattatgaa   660
aaacacaaag tgtatgcctg cgaagttacc catcagggtc tgagcagtcc ggttaccaaa   720
agctttaatc gtggtgaatg ttaattaact cgaggctgag caaagcagac tactaataac   780
ataaagtcta cgccggacgc atcgtggccc tagtacgcaa gttcacgtaa aaagggtaac   840
tagaggttga ggtgatttta tggaaattag cgaagttcag ctggttgaaa gcggtggtgg   900
tctgttcag cctggtggta gcctgcgtct gagctgtgca gcaagcggtt ttaacattaa    960
agatacctat atccactggg ttcgtcaggc accgggtaaa ggtctggaat gggttgcaga  1020
tgttaatccg aatagcggtg gtagcattta taaccagcgt tttaaggtc gttttaccct  1080
gagcgttgat cgtagcaaaa ataccctgta tctgcaaatg aatagtctgc gtgcagagga  1140
taccgcagtg tattattgtg cacgtaatct gggtccgagc ttctattttg attattgggg  1200
tcagggcacc ctggttaccg ttagcagcgc aagcaccaaa ggtccgagcg ttttttccgct  1260
```

```
ggcaccgagc agcaaaagca ccagcggtgg caccgcagca ctgggttgtc tggttaaaga  1320
ttatttccg  gaaccggtta ccgtgagctg aatagcggt  gcactgacca gtggtgttca   1380
tacctttccg gcagttctgc agagcagcgg tctgtatagt ctgagcagcg ttgttaccgt  1440
tccgagcagt agcctgggca cccagaccta tatttgtaat gttaatcata aaccgagcaa  1500
caccaaagtg gataaaaaag ttgaaccgaa aagctgcgat aaaacccata cctaa       1555

SEQ ID NO: 30          moltype = AA    length = 247
FEATURE                Location/Qualifiers
REGION                 1..247
                       note = Beta9-His Tag-light chain
source                 1..247
                       mol_type = protein
                       organism = synthetic construct
SEQUENCE: 30
MGSMLFRVTI NSGGGSGHHH HHHHHGGGSG MASDIQMTQS PSSLSASVGD RVTITCKASQ    60
DVSIGVAWYQ QKPGKAPKLL IYSASYRYTG VPSRFSGSGS GTDFTLTISS LQPEDFATYY   120
CQQYYIYPYT FGQGTKVEIK RTVAAPSVFI FPPSDEQLKS GTASVVCLLN NFYPREAKVQ   180
WKVDNALQSG NSQESVTEQD SKDSTYSLSS TLTLSKADYE KHKVYACEVT HQGLSSPVTK   240
SFNRGEC                                                             247

SEQ ID NO: 31          moltype = AA    length = 231
FEATURE                Location/Qualifiers
REGION                 1..231
                       note = heavy chain
source                 1..231
                       mol_type = protein
                       organism = synthetic construct
SEQUENCE: 31
MEISEVQLVE SGGGLVQPGG SLRLSCAASG FTFTDYTMDW VRQAPGKGLE WVADVNPNSG    60
GSIYNQRFKG RFTLSVDRSK NTLYLQMNSL RAEDTAVYYC ARNLGPSFYF DYWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH T            231

SEQ ID NO: 32          moltype = DNA   length = 1555
FEATURE                Location/Qualifiers
misc_feature           1..1555
                       note = Beta10*-LPert
source                 1..1555
                       mol_type = other DNA
                       organism = synthetic construct
SEQUENCE: 32
atggtgagcg gttggcgtct gttcaaaaaa atcagcggtg gtggtagcgg tcatcatcac    60
caccatcacc atcatggtgg tggcagtggt atggcagata tccagatgac ccagagcccg   120
ccgagcagcc tgagcgcaag cgttggtgat cgtgttacca ttacctgtaa ggcaagccag   180
gatgttagca ttggtgttgc atggtatcag cagaaaccgg gtaaagcacc gaaactgctg   240
atttatagcg caagctatcg ttataccggt gttccgagcc gttttagcgg tagcggcagc   300
ggcaccgatt ttaccctgac cattagcagc ctgcagccgg aagattttgc aacctattat   360
tgtcagcagt actacatcta tccgtacacc tttggtcagg gcaccaaagt tgaaattaaa   420
cgtaccgttg cagcaccgag cgttttttatc tttccgccta gcgatgagca gctgaaaagc   480
ggtacagcca gcgttgtttg tctgctgaat aactttatcc gcgtgaagc  aaaagttcag   540
tggaaagttg ataatgcact gcagagcggt aatagccaag aaagcgttac cgaacaggat   600
agcaaagata gcacctatag cctgagcagc acc ctgaccc tgagcaaagc agattatgaa   660
aaacacaaag tgtatgcctg cgaagttacc catcagggtc tgagcagtcc ggttaccaaa   720
agctttaatc gtggtgaatg ttaattaact cgaggctgag caaagcagac tactaataac   780
ataaagctct acgccggacgc atcgtggccc tagtacgaca gttcactaa aaagggtaac   840
tagaggttga ggtgatttta tggaaattag cgaagttcag ctggttgaaa gcggtggtga   900
tctggttcag cctggtggta gcctgcgtct gagctgtgca gcaagcggtt ttacctttac   960
cgattacacc atggattggg ttcgtcaggc accgggtaaa ggtctggaat gggttgcaga  1020
tgttaatccg aatagcggtg gtagcattta taaccagcgt tttaaaggtc gttttaccct  1080
gagcgttgat cgtagcaaaa ataccctgta tctgcaaatg aatagtctgc gtgcagagga  1140
taccgcagtg tattattgtg cacgtaatct gggtccgagc ttctatttttg attattgggg  1200
tcagggcacc ctggttaccg ttagcagcgc aagcaccaaa ggtccgagcg ttttttccgct  1260
ggcaccgagc agcaaaagca ccagcggtgg caccgcagca ctgggttgtc tggttaaaga  1320
ttatttccg  gaaccggtta ccgtgagctg aatagcggt  gcactgacca gtggtgttca   1380
tacctttccg gcagttctgc agagcagcgg tctgtatagt ctgagcagcg ttgttaccgt  1440
tccgagcagt agcctgggca cccagaccta tatttgtaat gttaatcata aaccgagcaa  1500
caccaaagtg gataaaaaag ttgaaccgaa aagctgcgat aaaacccata cctaa       1555

SEQ ID NO: 33          moltype = AA    length = 247
FEATURE                Location/Qualifiers
REGION                 1..247
                       note = Beta10*-His Tag-light chain
source                 1..247
                       mol_type = protein
                       organism = synthetic construct
SEQUENCE: 33
MVSGWRLFKK ISGGGSGHHH HHHHHGGGSG MASDIQMTQS PSSLSASVGD RVTITCKASQ    60
DVSIGVAWYQ QKPGKAPKLL IYSASYRYTG VPSRFSGSGS GTDFTLTISS LQPEDFATYY   120
CQQYYIYPYT FGQGTKVEIK RTVAAPSVFI FPPSDEQLKS GTASVVCLLN NFYPREAKVQ   180
```

```
WKVDNALQSG NSQESVTEQD SKDSTYSLSS TLTLSKADYE KHKVYACEVT HQGLSSPVTK   240
SFNRGEC                                                              247

SEQ ID NO: 34            moltype = AA  length = 231
FEATURE                  Location/Qualifiers
REGION                   1..231
                         note = heavy chain
source                   1..231
                         mol_type = protein
                         organism = synthetic construct
SEQUENCE: 34
MEISEVQLVE SGGGLVQPGG SLRLSCAASG FTFTDYTMDW VRQAPGKGLE WVADVNPNSG    60
GSIYNQRFKG RFTLSVDRSK NTLYLQMNSL RAEDTAVYYC ARNLGPSFYF DYWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH T            231

SEQ ID NO: 35            moltype = DNA  length = 1552
FEATURE                  Location/Qualifiers
misc_feature             1..1552
                         note = PertH-Beta9
source                   1..1552
                         mol_type = other DNA
                         organism = synthetic construct
SEQUENCE: 35
atggcaagcg atattcagat gacccagagc ccgagcagcc tgagcgcaag cgttggtgat    60
cgtgttacca ttacctgtaa ggcaagccag gatgttagca ttggtgttgc atggtatcag   120
cagaaaccgg gtaaagcacc gaaactgctg atttatagcg caagctatcg ttataccggt   180
gttccgagcc gttttagcgg tagcggcagc ggcaccgatt ttaccctgac cattagcagc   240
ctgcagccgg aagattttgc aacctattat tgtcagcagt actacatcta tccgtacacc   300
tttggtcagg gcaccaaagt tgaaattaaa cgtaccgttg cagcaccggt tttttatc    360
tttccgccta gcgatgagca gctgaaaagc ggtacagcca gcgttgtttg tctgctgaat   420
aactttttatc gcgtgaagc aaaagttcag tggaaagttg ataatgcact gcagagcggt   480
aatagccaag aaagcgttac gaacaggat agcaaagata gcacctatag cctgagcagc   540
accctgaccc tgagcaaagc agattatgaa aaacacaaag tgtatgcctg cgaagttacc   600
catcagggtc tgagcagtcc ggttaccaaa agctttaatc gtggtgaatg ttaattaact   660
cgaggctgag caaagcagac tactaataac ataaagtcta cgccggacgc atcgtggccc   720
tagtacgcaa gttcacgtaa aagggtaac tagaggttga ggtgatttta tggaaattag    780
cgaagttcag ctggttgaaa gcggtggtgg tctggttcag cctggtggta gcctgcgtct   840
gagctgtgca gcaagcggtt ttacctttac cgattacacc atggattggg ttcgtcaggc   900
accgggtaaa ggtctggaat gggttgcaga tgttaatccg aatagcggtg gtagcattta   960
taaccagcgt tttaaaggtc gttttaccct gagcgttgat cgtagcaaaa ataccctgta  1020
tctgcaaatg aatagtctgc gtgcagagga taccgcagtg tattattgtg cacgtaatct  1080
gggtccgagc ttctattttg attattgggg tcagggcacc gttaccgtta gcagcgc     1140
aagcaccaaa ggtccgagcg ttttttccgct ggcaccgagc agcaaaagca ccagcggtgg  1200
caccgcagca ctgggttgtc tggttaaaga ttattttccg gaaccggtta ccgtgagctg  1260
gaatagcggt gcactgacca gtggtgttca tacctttccg gcagttctgc agagcagcgg  1320
tctgtatagt ctgagcagcg ttgttaccgt tccgagcagt agcctgggca ccagacctga  1380
tatttgtaat gttaatcata aaccgagcaa caccaaagtg gataaaaaag ttgaaccgaa  1440
aagctgcgat aaaacccata ccggtggtgg tagcggtcat catcaccacc atcaccatca  1500
tggtggtggc agtggtggta gtgctgtt cgtgttacc attaacagct aa              1552

SEQ ID NO: 36            moltype = AA  length = 217
FEATURE                  Location/Qualifiers
REGION                   1..217
                         note = light chain
source                   1..217
                         mol_type = protein
                         organism = synthetic construct
SEQUENCE: 36
MASDIQMTQS PSSLSASVGD RVTITCKASQ DVSIGVAWYQ QKPGKAPKLL IYSASYRYTG    60
VPSRFSGSGS GTDFTLTISS LQPEDFATYY CQQYYIYPYT FGQGTKVEIK RTVAAPSVFI   120
FPPSDEQLKS GTASVVCLLN NFYPREAKVQ WKVDNALQSG NSQESVTEQD SKDSTYSLSS   180
TLTLSKADYE KHKVYACEVT HQGLSSPVTK SFNRGEC                            217

SEQ ID NO: 37            moltype = AA  length = 260
FEATURE                  Location/Qualifiers
REGION                   1..260
                         note = heavy chain- His Tag-Beta9
source                   1..260
                         mol_type = protein
                         organism = synthetic construct
SEQUENCE: 37
MEISEVQLVE SGGGLVQPGG SLRLSCAASG FTFTDYTMDW VRQAPGKGLE WVADVNPNSG    60
GSIYNQRFKG RFTLSVDRSK NTLYLQMNSL RAEDTAVYYC ARNLGPSFYF DYWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TGGGSGHHHH   240
HHHGGGSSGG SMLFRVTINS                                                260

SEQ ID NO: 38            moltype = DNA  length = 1552
```

| FEATURE | Location/Qualifiers |
|---|---|
| misc_feature | 1..1552 |
| | note = PertH-Beta10* |
| source | 1..1552 |
| | mol_type = other DNA |
| | organism = synthetic construct |

SEQUENCE: 38

```
atggcaagcg atattcagat gacccagagc ccgagcagcc tgagcgcaag cgttggtgat    60
cgtgttacca ttacctgtaa ggcaagccag gatgttagca ttggtgttgc atggtatcag   120
cagaaaccgg gtaaagcacc gaaactgctg atttatagcg caagctatcg ttataccggt   180
gttccgagcc gttttagcgg tagcggcagc ggcaccgatt ttaccctgac cattagcagc   240
ctgcagccga agattttgc aacctattat tgtcagcagt actacatcta tccgtacacc    300
tttggtcagg gcaccaaagt tgaaattaaa cgtaccgttg cagcaccgag cgttttatc    360
tttccgccta gcgatgagca gctgaaaagc ggtacagcca gcgttgtttg tctgctgaat   420
aactttatc cgcgtgaagc aaaagttcag tggaaagttg ataatgcact gcagagcggt   480
aatagccaag aaagcgttac cgaacaggat agcaaagata gcacctatag cctgagcagc   540
accctgaccc tgagcaaagc agattatgaa aaacacaaaa tgtatgcctg cgaagttacc   600
catcagggtc tgagcagtcc ggttaccaaa agctttaatc ggtgaatg ttaattaact     660
cgaggctgag caaagcagac tactaataac ataaagtcta cgccggacgc atcgtggccc   720
tagtacgcaa gttcacgtaa aagggtaac tagaggttga ggtgatttta tggaaattag    780
cgaagttcag ctggttgaaa gcggtggtgg tctggttcag cctggtggta gcctgcgtct   840
gagctgtgca gcaagcggtt ttaccttac gattacacc atggattgga ttcgtcaggc    900
accgggtaaa ggtctggaat gggttgcaga tgttaatccg aatagcggtg gtagcattta   960
taaccagcgt tttaaaggtc gttttaccct gagcgttgat cgtagcaaaa ataccctgta  1020
tctgcaaatg aatagtctgc gtgcagagga taccgcagtg tattattgtg cacgtaatct  1080
gggtccgagc ttctattttg attattgggg tcagggcacc ctggttaccg ttagcagcgc  1140
aagcaccaaa ggtccgagcg tttttccgct ggcaccgagc agcaaaagca ccagcggtgg  1200
caccgcagca ctgggttgtc tggttaaaga ttatttccg gaaccggtta ccgtgagctg   1260
gaatagcggt gcactgacca gtggtgttca tacctttccg gcagttctgc agagcagcgg  1320
tctgtatagt ctgagcagcg ttgttaccgt tccgagcagt agcctgggca cccagaccta  1380
tatttgtaat gttaatcata aaccgagcaa caccaaagtg gataaaaaag ttgaaccgaa  1440
aagctgcgat aaaacccata ccggtggtgg tagcggtcat catcaccac atcaccatca   1500
tggtggtggc agtggtgtga gcggttggcg tctgttcaaa aaaatcagct aa          1552
```

| SEQ ID NO: 39 | moltype = AA length = 217 |
|---|---|
| FEATURE | Location/Qualifiers |
| REGION | 1..217 |
| | note = light chain |
| source | 1..217 |
| | mol_type = protein |
| | organism = synthetic construct |

SEQUENCE: 39

```
MASDIQMTQS PSSLSASVGD RVTITCKASQ DVSIGVAWYQ QKPGKAPKLL IYSASYRYTG    60
VPSRFSGSGS GTDFTLTISS LQPEDFATYY CQQYYIYPYT FGQGTKVEIK RTVAAPSVFI   120
FPPSDEQLKS GTASVVCLLN NFYPREAKVQ WKVDNALQSG NSQESVTEQD SKDSTYSLSS   180
TLTLSKADYE KHKVYACEVT HQGLSSPVTK SFNRGEC                            217
```

| SEQ ID NO: 40 | moltype = AA length = 260 |
|---|---|
| FEATURE | Location/Qualifiers |
| REGION | 1..260 |
| | note = heavy chain-His Tag-Beta10* |
| source | 1..260 |
| | mol_type = protein |
| | organism = synthetic construct |

SEQUENCE: 40

```
MEISEVQLVE SGGGLVQPGG SLRLSCAASG FTFTDYTMDW VRQAPGKGLE WVADVNPNSG    60
GSIYNQRFKG RFTLSVDRSK NTLYLQMNSL RAEDTAVYYC ARNLGPSFYF DYWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TGGGSGHHHH   240
HHHHGGGSGV SGWRLFKKIS                                               260
```

| SEQ ID NO: 41 | moltype = DNA length = 465 |
|---|---|
| FEATURE | Location/Qualifiers |
| misc_feature | 1..465 |
| | note = Beta9-G3 |
| source | 1..465 |
| | mol_type = other DNA |
| | organism = synthetic construct |

SEQUENCE: 41

```
atgggtagta tgctgtttcg tgttaccatt aacagcggtg gtggtagcgg tcatcatcac    60
caccatcacc atcatggtgg tggcagtggt gatctgggta aaaaactgct ggaagcagca   120
cgtgcaggtc aggatgatga agttcgtatt ctgatggcaa atggtgcaga tgttaatgcc   180
aaagatgaat atggtctgac accgctgtat ctggcaaccg cacatggtca tctggaaatt   240
gttgaagttc tgctgaaaaa cggtgccgat gtgaatgcaa ttgatgcaat tggttttact   300
cctctgcatc tggcagcatt tattggccac ctggaaatcg ccgaggtgct gctgaaacat   360
ggtgcggacg ttaacgcaca ggataaattt ggtaaaccg cctttgatat tagcattggc    420
aatggcaatg aagatctggc agaaatcctg cagaaactga ctaa                    465
```

| SEQ ID NO: 42 | moltype = AA length = 154 |
|---|---|

| FEATURE | Location/Qualifiers |
|---|---|
| REGION | 1..154 |
| | note = Beta9-His Tag-G3 |
| source | 1..154 |
| | mol_type = protein |
| | organism = synthetic construct |

SEQUENCE: 42
```
MGSMLFRVTI NSGGGSGHHH HHHHHGGGSG DLGKKLLEAA RAGQDDEVRI LMANGADVNA   60
KDEYGLTPLY LATAHGHLEI EVVLLKNGAD VNAVDAIGFT PLHLAAFIGH LEIAEVLLKH  120
GADVNAQDKF GKTAFDISIG NGNEDLAEIL QKLN                              154
```

| SEQ ID NO: 43 | moltype = DNA   length = 465 |
|---|---|
| FEATURE | Location/Qualifiers |
| misc_feature | 1..465 |
| | note = Beta10*-G3 |
| source | 1..465 |
| | mol_type = other DNA |
| | organism = synthetic construct |

SEQUENCE: 43
```
atggtgagcg gttggcgtct gttcaaaaaa atcagcggtg gtggtagcgg tcatcatcac   60
caccatcacc atcatggtgg tggcagtggt gatctgggta aaaaactgct ggaagcagca  120
cgtgcaggtc aggatgatga agttcgtatt ctgatgcaaa atggtgcaga tgttaatgcc  180
aaagatgaat atggtctgac accgctgtat ctggcaaccg cacatggtca tctggaaatt  240
gttgaagttc tgctgaaaaa cggtgccgat gtgaatgcag ttgatgcaat tggttttact  300
cctctgcatc tggcagcatt tattggccac ctggaaatcg ccgaggtgct gctgaaacat  360
ggtgcggacg ttaacgcaca ggataaattt ggtaaaaccg cctttgatat tagcattggc  420
aatggcaatg aagatctggc agaaatcctg cagaaactga actaa                  465
```

| SEQ ID NO: 44 | moltype = AA   length = 154 |
|---|---|
| FEATURE | Location/Qualifiers |
| REGION | 1..154 |
| | note = Beta10*-His Tag-G3 |
| source | 1..154 |
| | mol_type = protein |
| | organism = synthetic construct |

SEQUENCE: 44
```
MVSGWRLFKK ISGGGSGHHH HHHHHGGGSG DLGKKLLEAA RAGQDDEVRI LMANGADVNA   60
KDEYGLTPLY LATAHGHLEI EVVLLKNGAD VNAVDAIGFT PLHLAAFIGH LEIAEVLLKH  120
GADVNAQDKF GKTAFDISIG NGNEDLAEIL QKLN                              154
```

| SEQ ID NO: 45 | moltype = DNA   length = 489 |
|---|---|
| FEATURE | Location/Qualifiers |
| misc_feature | 1..489 |
| | note = G3-Beta9 |
| source | 1..489 |
| | mol_type = other DNA |
| | organism = synthetic construct |

SEQUENCE: 45
```
atgcgtggta gccatcatca tcaccatcat ggtagcgatc tgggtaaaaa actgctggaa   60
gcagcacgtg caggtcagga tgatgaagtt cgtattctga tggcaaatgg tgcagatgtt  120
aatgccaaag atgaatatgg tctgacaccg ctgtatctgg caaccgcaca tggtcatctg  180
gaaattgttg aagttctgct gaaaaacggt gccgatgtga atgcagttga tgcaattggt  240
tttactcctc tgcatctggc agcatttatt ggccacctgg aaatcgccga ggtgctgctg  300
aaacatggtg cggacgttaa cgcacaggat aaatttggta aaaccgcctt tgatattagc  360
attggcaatg gcaatgaaga tctggcagaa atcctgcaga aactgaacgg tggtggtagc  420
ggtggtggtg gctcaggtgg cggtggttct ggtggtagta tgctgtttcg tgttaccatt  480
aacagctaa                                                          489
```

| SEQ ID NO: 46 | moltype = AA   length = 162 |
|---|---|
| FEATURE | Location/Qualifiers |
| REGION | 1..162 |
| | note = His Tag-G3-Beta9 |
| source | 1..162 |
| | mol_type = protein |
| | organism = synthetic construct |

SEQUENCE: 46
```
MRGSHHHHHH GSDLGKKLLE AARAGQDDEV RILMANGADV NAKDEYGLTP LYLATAHGHL   60
EIEVVLLKNG ADVNAVDAIG FTPLHLAAFI GHLEIAEVLL KHGADVNAQD KFGKTAFDIS  120
IGNGNEDLAE ILQKLNGGGS GGGGSGGGGS GGSMLFRVTI NS                     162
```

| SEQ ID NO: 47 | moltype = DNA   length = 489 |
|---|---|
| FEATURE | Location/Qualifiers |
| misc_feature | 1..489 |
| | note = G3-Beta10* |
| source | 1..489 |
| | mol_type = other DNA |
| | organism = synthetic construct |

SEQUENCE: 47
```
atgcgtggta gccatcatca tcaccatcat ggtagcgatc tgggtaaaaa actgctggaa   60
```

```
gcagcacgtg caggtcagga tgatgaagtt cgtattctga tggcaaatgg tgcagatgtt    120
aatgccaaag atgaatatgg tctgacaccg ctgtatctgg caaccgcaca tggtcatctg    180
gaaattgttg aagttctgct gaaaaacggt gccgatgtga atgcagttga tgcaattggt    240
tttactcctc tgcatctggc agcatttatt ggccacctgg aaatcgccga ggtgctgctg    300
aaacatggtg cggacgttaa cgcacaggat aaatttggta aaaccgcctt tgatattagc    360
attggcaatg gcaatgaaga tctggcagaa atcctgcaga aactgaacgg tggtggtagc    420
ggtggtggtg gctcaggtgg cggtggttct ggtgtgagcg gttggcgtct gttcaaaaaa    480
atcagctaa                                                            489

SEQ ID NO: 48        moltype = AA   length = 162
FEATURE              Location/Qualifiers
REGION               1..162
                     note = His Tag-G3-Beta10*
source               1..162
                     mol_type = protein
                     organism = synthetic construct
SEQUENCE: 48
MRGSHHHHHH GSDLGKKLLE AARAGQDDEV RILMANGADV NAKDEYGLTP LYLATAHGHL     60
EIVEVLLKNG ADVNAVDAIG FTPLHAAFI GHLEIAEVLL KHGADVNAQD KFGKTAFDIS     120
IGNGNEDLAE ILQKLNGGGS GGGGSGGGGS GVSGWRLFKK IS                       162

SEQ ID NO: 49        moltype = DNA   length = 567
FEATURE              Location/Qualifiers
misc_feature         1..567
                     note = Beta9-9.29
source               1..567
                     mol_type = other DNA
                     organism = synthetic construct
SEQUENCE: 49
atgggtagta tgctgtttcg tgttaccatt aacagcggtg gtggtagcgg tcatcatcac    60
caccatcacc atcatggtgg tggcagtggt ggtagcgatc tgggtaaaaa actgctggaa    120
gcagcacgtg caggtcagga tgatgaagtt cgtattctga tggcaaatgg tgcagatgtt    180
aatgccoatg attttatgg tattacaccg ctgcatctgg cagcaaattt tggtcatctg    240
gaaattgttg aagtgctgct gaaacatggt gccgatgtga acgcatttga ttatgataat    300
acccctctgc acctggctgc agatgctggc cacctgaaaa tcgtagaggt tctgctgaaa    360
tacggtgcgg acgttaatgc aagcgatcgt gatggtcata ccccactgca tctggcagcc    420
cgtgaaggcc atctggaaat cgtggaagta ctgctgaaaa atggcgcaga cgtgaatgca    480
caggataaat ttggtaaaac cccgtttgat ctggccattg ataatggcaa tgaagatatt    540
gccgaggtgc tgcagaaagc agcataa                                        567

SEQ ID NO: 50        moltype = AA   length = 188
FEATURE              Location/Qualifiers
REGION               1..188
                     note = Beta9-His Tag-9.29
source               1..188
                     mol_type = protein
                     organism = synthetic construct
SEQUENCE: 50
MGSMLFRVTI NSGGGSGHHH HHHHGGGSG GSDLGKKLLE AARAGQDDEV RILMANGADV      60
NAHDFYGITP LHLAANFGHL EIVEVLLKHG ADVNAFDYDN TPLHLAADAG HLEIVEVLLK     120
YGADVNASDR DGHTPLHLAA REGHLEIVEV LLKNGADVNA QDKFGKTPFD LAIDNGNEDI     180
AEVLQKAA                                                              188

SEQ ID NO: 51        moltype = DNA   length = 567
FEATURE              Location/Qualifiers
misc_feature         1..567
                     note = Beta10*-9.29
source               1..567
                     mol_type = other DNA
                     organism = synthetic construct
SEQUENCE: 51
atggtgagcg gttggcgtct gttcaaaaaa atcagcggtg gtggtagcgg tcatcatcac    60
caccatcacc atcatggtgg tggcagtggt ggtagcgatc tgggtaaaaa actgctggaa    120
gcagcacgtg caggtcagga tgatgaagtt cgtattctga tggcaaatgg tgcagatgtt    180
aatgccoatg attttatgg tattacaccg ctgcatctgg cagcaaattt tggtcatctg    240
gaaattgttg aagtgctgct gaaacatggt gccgatgtga acgcatttga ttatgataat    300
acccctctgc acctggctgc agatgctggc cacctgaaaa tcgtagaggt tctgctgaaa    360
tacggtgcgg acgttaatgc aagcgatcgt gatggtcata ccccactgca tctggcagcc    420
cgtgaaggcc atctggaaat cgtggaagta ctgctgaaaa atggcgcaga cgtgaatgca    480
caggataaat ttggtaaaac cccgtttgat ctggccattg ataatggcaa tgaagatatt    540
gccgaggtgc tgcagaaagc agcataa                                        567

SEQ ID NO: 52        moltype = AA   length = 188
FEATURE              Location/Qualifiers
REGION               1..188
                     note = Beta10*-His Tag-9.29
source               1..188
                     mol_type = protein
                     organism = synthetic construct
```

```
SEQUENCE: 52
MVSGWRLFKK ISGGGSGHHH HHHHHGGGSG GSDLGKKLLE AARAGQDDEV RILMANGADV    60
NAHDFYGITP LHLAANFGHL EIVEVLLKHG ADVNAFDYDN TPLHLAADAG HLEIVEVLLK   120
YGADVNASDR DGHTPLHLAA REGHLEIVEV LLKNGADVNA QDKFGKTPFD LAIDNGNEDI   180
AEVLQKAA                                                           188

SEQ ID NO: 53            moltype = DNA  length = 567
FEATURE                  Location/Qualifiers
misc_feature             1..567
                         note = 9.29-Beta9
source                   1..567
                         mol_type = other DNA
                         organism = synthetic construct
SEQUENCE: 53
atgggtagcg atctgggtaa aaaactgctg gaagcagcac gtgcaggtca ggatgatgaa    60
gttcgtattc tgatggcaaa tggtgcagat gttaatgccc atgatttta tggtattaca   120
ccgctgcatc tggcagcaaa ttttggtcat ctggaaattg ttgaagtgct gctgaaacat   180
ggtgccgatg tgaacgcatt tgattatgat aatacccctc tgcacctggc tgcagatgct   240
ggccacctgg aaatcgtaga ggttctgctg aaatacggtg cggacgttaa tgcaagcgat   300
cgtgatggtc atacccccact gcatctggca gcccgtgaag ccatctgga aatcgtggaa   360
gtactgctga aaaatggcgc agacgtgaat gcacaggata aatttggtaa aacccccgttt   420
gatctggcca ttgataatgg caatgaagat attgccgagg tgctgcagaa agcagcaggt   480
ggtggtagcg gtcatcatca ccaccatcac catcatggtg gtggcagtgg tggtagtatg   540
ctgtttcgtg ttaccattaa cagctaa                                      567

SEQ ID NO: 54            moltype = AA  length = 188
FEATURE                  Location/Qualifiers
REGION                   1..188
                         note = 9.29-His Tag-Beta9
source                   1..188
                         mol_type = protein
                         organism = synthetic construct
SEQUENCE: 54
MGSDLGKKLL EAARAGQDDE VRILMANGAD VNAHDFYGIT PLHLAANFGH LEIVEVLLKH    60
GADVNAFDYD NTPLHLAADA GHLEIVEVLL KYGADVNASD RDGHTPLHLA AREGHLEIVE   120
VLLKNGADVN AQDKFGKTPF DLAIDNGNED IAEVLQKAAG GGSGHHHHHH HHGGGSGGSM   180
LFRVTINS                                                           188

SEQ ID NO: 55            moltype = DNA  length = 567
FEATURE                  Location/Qualifiers
misc_feature             1..567
                         note = 9.29-Beta10*
source                   1..567
                         mol_type = other DNA
                         organism = synthetic construct
SEQUENCE: 55
atgggtagcg atctgggtaa aaaactgctg gaagcagcac gtgcaggtca ggatgatgaa    60
gttcgtattc tgatggcaaa tggtgcagat gttaatgccc atgatttta tggtattaca   120
ccgctgcatc tggcagcaaa ttttggtcat ctggaaattg ttgaagtgct gctgaaacat   180
ggtgccgatg tgaacgcatt tgattatgat aatacccctc tgcacctggc tgcagatgct   240
ggccacctgg aaatcgtaga ggttctgctg aaatacggtg cggacgttaa tgcaagcgat   300
cgtgatggtc atacccccact gcatctggca gcccgtgaag ccatctgga aatcgtggaa   360
gtactgctga aaaatggcgc agacgtgaat gcacaggata aatttggtaa aacccccgttt   420
gatctggcca ttgataatgg caatgaagat attgccgagg tgctgcagaa agcagcaggt   480
ggtggtagcg gtcatcatca ccaccatcac catcatggtg gtggcagtgg tgtgagcggt   540
tggcgtctgt tcaaaaaaat cagctaa                                      567

SEQ ID NO: 56            moltype = AA  length = 188
FEATURE                  Location/Qualifiers
REGION                   1..188
                         note = 9.29-His Tag-Beta10*
source                   1..188
                         mol_type = protein
                         organism = synthetic construct
SEQUENCE: 56
MGSDLGKKLL EAARAGQDDE VRILMANGAD VNAHDFYGIT PLHLAANFGH LEIVEVLLKH    60
GADVNAFDYD NTPLHLAADA GHLEIVEVLL KYGADVNASD RDGHTPLHLA AREGHLEIVE   120
VLLKNGADVN AQDKFGKTPF DLAIDNGNED IAEVLQKAAG GGSGHHHHHH HHGGGSGVSG   180
WRLFKKIS                                                           188

SEQ ID NO: 57            moltype = DNA  length = 1479
FEATURE                  Location/Qualifiers
misc_feature             1..1479
                         note = HT-Beta9-TNF
source                   1..1479
                         mol_type = other DNA
                         organism = synthetic construct
SEQUENCE: 57
atgaaacatc atcaccatca ccacgcagaa atcggtactg ctttccatt cgaccccat     60
```

```
tatgtggaag tcctgggcga gcgcatgcac tacgtcgatg ttggtccgcg cgatggcacc    120
cctgtgctgt tcctgcacgg taacccgacc tcctcctacg tgtggcgcaa catcatcccg    180
catgttgcac cgacccatcg ctgcattgct ccagacctga tcggtatggg caaatccgac    240
aaaccagacc tgggttattt cttcgacgac cacgtccgct tcatggatgc cttcatcgaa    300
gccctgggtc tggaagaggt cgtcctggtc attcacgact ggggctccgc tctgggtttc    360
cactgggcca agcgcaatcc agagcgcgtc aaaggtattg catttatgga gttcatccgc    420
cctatcccga cctgggacga atggccagaa tttgcccgcg agaccttcca ggccttccgc    480
accaccgacg tcggccgcaa gctgatcatc gatcagaacg tttttatcga gggtacgctg    540
ccgatgggtg tcgtccgccc gctgactgaa gtcgagatgg accattaccg cgagccgttc    600
ctgaatcctg ttgaccgcga gccactgtgg cgcttcccaa acgagctgcc aatcgccggt    660
gagccagcga acatcgtcgc gctggtcgaa gaatacatgg actggctgca ccagtcccct    720
gtcccgaagc tgctgttctg gggcaccca ggcgttctga tcccaccggc cgaagccgct    780
cgcctggcca aagcctgcc taactgcaag gctgtggaca tcggcccggg tctgaatctg    840
ctgcaagaag acaacccgga cctgatcggc agcgagatcg cgcgctggct gtcgacgctc    900
gagatttccg gcgagccaac cactgaggat ctgtactttc agggtagtat gctgtttcgt    960
gttaccatta acagcggtgg tggtagcggt ggtggtggca gtggtgttcg tagcagcagt   1020
cgtaccccga gcgataaacc ggttgcacat gttgttgcaa atccgcaggc cgaaggtcag   1080
ctgcagtggc tgaatcgtcg tgcaaatgca ctgctggcaa atggtgttga actgcgtgat   1140
aatcagctgg ttgttccgag cgaaggtctg tatctgattt atagccaggt tctgtttaaa   1200
ggtcaggtt gtccgagcac acatgttctg ctgacccata ccattagccg tattgcagtt   1260
agctatcaga ccaaagttaa tctgctgagc gcaattaaaa gcccgtgtca gcgtgaaaca   1320
ccggaaggtg ccgaagcaaa accgtggtat gaaccgattt atcttggtgg tgtttttcag   1380
ctggaaaagg gtgatcgtct gagcgcagaa attaatcgtc cggattatct ggattttgca   1440
gaaagcggtc aggtgtattt tggcattatt gcattataa                          1479

SEQ ID NO: 58            moltype = AA  length = 492
FEATURE                  Location/Qualifiers
REGION                   1..492
                         note = HT-Beta9-TNF
source                   1..492
                         mol_type = protein
                         organism = synthetic construct
SEQUENCE: 58
MKHHHHHHAE IGTGFPFDPH YVEVLGERMH YVDVGPRDGT PVLFLHGNPT SSYVWRNIIP     60
HVAPTHRCIA PDLIGMGKSD KPDLGYFFDD HVRFMDAFIE ALGLEEVVLV IHDWGSALGF    120
HWAKRNPERV KGIAFMEFIR PIPTWDEWPE FARETFQAFR TTDVGRKLII DQNVFIEGTL    180
PMGVVRPLTE VEMDHYREPF LNPVDREPLW RFPNELPIAG EPANIVALVE EYMDWLHQSP    240
VPKLLFWGTP GVLIPPAEAA RLAKSLPNCK AVDIGPGLNL LQEDNPDLIG SEIARWLSTL    300
EISGEPTTED LYFQGSMLFR VTINSGGGSG GGGSGVRSSS RTPSDKPVAH VVANPQAEGQ    360
LQWLNRRANA LLANGVELRD NQLVVPSEGL YLIYSQVLFK GQGCPSTHVL LTHTISRIAV    420
SYQTKVNLLS AIKSPCQRET PEGAEAKPWY EPIYLGGVFQ LEKGDRLSAE INRPDYLDFA    480
ESGQVYFGII AL                                                        492

SEQ ID NO: 59            moltype = DNA  length = 1482
FEATURE                  Location/Qualifiers
misc_feature             1..1482
                         note = HT-TNF-Beta9
source                   1..1482
                         mol_type = other DNA
                         organism = synthetic construct
SEQUENCE: 59
atgaaacatc atcaccatca ccacgcagaa atcggtactg gctttccatt cgacccccat     60
tatgtggaag tcctgggcga gcgcatgcac tacgtcgatg ttggtccgcg cgatggcacc    120
cctgtgctgt tcctgcacgg taacccgacc tcctcctacg tgtggcgcaa catcatcccg    180
catgttgcac cgacccatcg ctgcattgct ccagacctga tcggtatggg caaatccgac    240
aaaccagacc tgggttattt cttcgacgac cacgtccgct tcatggatgc cttcatcgaa    300
gccctgggtc tggaagaggt cgtcctggtc attcacgact ggggctccgc tctgggtttc    360
cactgggcca agcgcaatcc agagcgcgtc aaaggtattg catttatgga gttcatccgc    420
cctatcccga cctgggacga atggccagaa tttgcccgcg agaccttcca ggccttccgc    480
accaccgacg tcggccgcaa gctgatcatc gatcagaacg tttttatcga gggtacgctg    540
ccgatgggtg tcgtccgccc gctgactgaa gtcgagatgg accattaccg cgagccgttc    600
ctgaatcctg ttgaccgcga gccactgtgg cgcttcccaa acgagctgcc aatcgccggt    660
gagccagcga acatcgtcgc gctggtcgaa gaatacatgg actggctgca ccagtcccct    720
gtcccgaagc tgctgttctg gggcaccca ggcgttctga tcccaccggc cgaagccgct    780
cgcctggcca aagcctgcc taactgcaag gctgtggaca tcggcccggg tctgaatctg    840
ctgcaagaag acaacccgga cctgatcggc agcgagatcg cgcgctggct gtcgacgctc    900
gagatttccg gcgagccaac cactgaggat ctgtactttc agggtgttcg tagcagcagt    960
cgtaccccga gcgataaacc ggttgcacat gttgttgcaa atccgcaggc cgaaggtcag   1020
ctgcagtggc tgaatcgtcg tgcaaatgca ctgctggcaa atggtgttga actgcgtgat   1080
aatcagctgg ttgttccgag cgaaggtctg tatctgattt atagccaggt tctgtttaaa   1140
ggtcaggtt gtccgagcac acatgttctg ctgacccata ccattagccg tattgcagtt   1200
agctatcaga ccaaagttaa tctgctgagc gcaattaaaa gcccgtgtca gcgtgaaaca   1260
ccggaaggtg ccgaagcaaa accgtggtat gaaccgattt atcttggtgg tgtttttcag   1320
ctggaaaagg gtgatcgtct gagcgcagaa attaatcgtc cggattatct ggattttgca   1380
gaaagcggtc aggtgtattt tggcattatt gcattaggcg gtgttcagg tggtgcggt   1440
tctggtggta gatgctgtt tcgtgttacc attaacagct aa                       1482

SEQ ID NO: 60            moltype = AA  length = 493
FEATURE                  Location/Qualifiers
```

| | | | |
|---|---|---|---|
| REGION | 1..493 | | |
| | note = HT-TNF-Beta9 | | |
| source | 1..493 | | |
| | mol_type = protein | | |
| | organism = synthetic construct | | |

SEQUENCE: 60
```
MKHHHHHHAE IGTGFPFDPH YVEVLGERMH YVDVGPRDGT PVLFLHGNPT SSYVWRNIIP    60
HVAPTHRCIA PDLIGMGKSD KPDLGYFFDD HVRFMDAFIE ALGLEEVVLV IHDWGSALGF   120
HWAKRNPERV KGIAFMEFIR PIPTWDEWPE FARETFQAPF TTDVGRKLII DQNVFIEGTL   180
PMGVVRPLTE VEMDHYREPF LNPVDREPLW RFPNELPIAG EPANIVALVE EYMDWLHQSP   240
VPKLLFWGTP GVLIPPAEAA RLAKSLPNCK AVDIGPGLNL LQEDNPDLIG SEIARWLSTL   300
EISGEPTTED LYFQGVRSSS RTPSDKPVAH VVANPQAEGQ LQWLNRRANA LLANGVELRD   360
NQLVVPSEGL YLIYSQVLFK GQGCPSTHVL LTHTISRIAV SYQTKVNLLS AIKSPCQRET   420
PEGAEAKPWY EPIYLGGVFQ LEKGDRLSAE INRPDYLDFA ESGQVYFGII ALGGGSGGGG   480
SGGSMLFRVT INS                                                      493
```

| | | | |
|---|---|---|---|
| SEQ ID NO: 61 | moltype = DNA length = 1482 | | |
| FEATURE | Location/Qualifiers | | |
| misc_feature | 1..1482 | | |
| | note = HT-Beta10*-TNF | | |
| source | 1..1482 | | |
| | mol_type = other DNA | | |
| | organism = synthetic construct | | |

SEQUENCE: 61
```
atgaaacatc atcaccatca ccacgcagaa atcggtactg gctttccatt cgacccccat    60
tatgtggaag tcctgggcga gcgcatgcac tacgtcgatg ttggtccgcg cgatggcacc   120
cctgtgctgt tcctgcacgg taacccgacc tcctcctacg tgtggcgcaa catcatcccg   180
catgttgcac cgacccatcg ctgcattgct ccagacctga tcggtatggg caaatccgac   240
aaaccagacc tgggttattt cttcgacgac cacgtccgct tcatggatgc cttcatcgaa   300
gccctgggtc tggaagaggt cgtcctggtc attcacgact ggggctccgc tctgggtttc   360
cactgggcca agcgcaatcc agagcgcgtc aaaggtattg catttatgga gttcatccgc   420
cctatcccga cctgggacga atggccagaa tttgcccgcg agaccttcca ggccttccgc   480
accaccgacg tcgccgcaa gctgatcatc gatcagaacg tttttatcga gggtacgctg   540
ccgatgggtg tcgtccgccc gctgactgaa gtcgagatgg accattaccg cgagccgttc   600
ctgaatcctg ttgaccgcga gccactgtgg cgcttcccaa acgagctgcc aatcgccggt   660
gagccagcga acatcgtcgc gctggtcgaa gaatacatga actggctgca ccagtccct   720
gtcccgaagc tgctgttctg gggcacccca ggcgttctga tcccaccggc cgaagccgct   780
cgcctggcca aagcctgcc taactgcaag gctgtgacat cggccgggg tctgaatctg   840
ctgcaagaag acaacccga cctgatcggc agcgagatcg cgcgctggct gtcgacgctg   900
gagatttccg gcgagccaac cactgaggat ctgtactttc agggtgtgag cggttggcgt   960
ctgttcaaaa aaatcagcgg tggtggtagc ggtggtggtg gcagtggtgt tcgtagcagc  1020
agtcgtaccc gagcgataa accggttgca catgttgttg caaatccgca ggccgaaggt  1080
cagctgcagt ggctgaatcg tcgtgcaaat gcactggctg tgaactgcgt c           1140
gataatcagc tggttgttcc gagcgaaggt ctgtatctga tttatagcca ggttctgttt  1200
aaaggtcagg gttgtccgag cacacatgtt ctgctgaccc ataccattag ccgtattgca  1260
gttagctatc agaccaaagt taatctgcta gcgcaattaa aaagcccgtg tcagcgtgaa  1320
acaccggaag tgccgaagc aaaaccgtgg tatgaaccgt tttatcttgg tggtgttttt  1380
cagctggaaa agggtgatcg tctgagcgca gaaattaatc gtccggatta tctggatttt  1440
gcagaaagcg gtcaggtgta ttttggcatt attgcattat aa                     1482
```

| | | | |
|---|---|---|---|
| SEQ ID NO: 62 | moltype = AA length = 493 | | |
| FEATURE | Location/Qualifiers | | |
| REGION | 1..493 | | |
| | note = HT-Beta10*-TNF | | |
| source | 1..493 | | |
| | mol_type = protein | | |
| | organism = synthetic construct | | |

SEQUENCE: 62
```
MKHHHHHHAE IGTGFPFDPH YVEVLGERMH YVDVGPRDGT PVLFLHGNPT SSYVWRNIIP    60
HVAPTHRCIA PDLIGMGKSD KPDLGYFFDD HVRFMDAFIE ALGLEEVVLV IHDWGSALGF   120
HWAKRNPERV KGIAFMEFIR PIPTWDEWPE FARETFQAFR TTDVGRKLII DQNVFIEGTL   180
PMGVVRPLTE VEMDHYREPF LNPVDREPLW RFPNELPIAG EPANIVALVE EYMDWLHQSP   240
VPKLLFWGTP GVLIPPAEAA RLAKSLPNCK AVDIGPGLNL LQEDNPDLIG SEIARWLSTL   300
EISGEPTTED LYFQGVSGWR LFKKISGGGS GGGGSGVRSS SRTPSDKPVA HVVANPQAEG   360
QLQWLNRRAN ALLANGVELR DNQLVVPSEG LYLIYSQVLF KGQGCPSTHV LLTHTISRIA   420
VSYQTKVNLL SAIKSPCQRE TPEGAEAKPW YEPIYLGGVF QLEKGDRLSA EINRPDYLDF   480
AESGQVYFGI IAL                                                      493
```

| | | | |
|---|---|---|---|
| SEQ ID NO: 63 | moltype = DNA length = 1482 | | |
| FEATURE | Location/Qualifiers | | |
| misc_feature | 1..1482 | | |
| | note = HT-TNF-Beta10* | | |
| source | 1..1482 | | |
| | mol_type = other DNA | | |
| | organism = synthetic construct | | |

SEQUENCE: 63
```
atgaaacatc atcaccatca ccacgcagaa atcggtactg gctttccatt cgacccccat    60
tatgtggaag tcctgggcga gcgcatgcac tacgtcgatg ttggtccgcg cgatggcacc   120
cctgtgctgt tcctgcacgg taacccgacc tcctcctacg tgtggcgcaa catcatcccg   180
```

```
catgttgcac cgacccatcg ctgcattgct ccagacctga tcggtatggg caaatccgac  240
aaaccagacc tgggttattt cttcgacgca cacgtccgct tcatggatgc cttcatcgaa  300
gccctgggtc tggaagaggt cgtcctggtc attcacgact ggggctccgc tctgggtttc  360
cactgggcca agcgcaatcc agagcgcgtt aaaggtattg catttatgga gttcatccgc  420
cctatcccga cctgggacga atgggccaga atttgcccgc agaccttcca ggccttccgc  480
accaccgacg tcggccgcaa gctgatcatc gatcagaacg tttttatcga gggtacgctg  540
ccgatgggtg tcgtccgccc gctgactgaa gtcgagatgg accattaccg cgagccgttc  600
ctgaatcctg ttgaccgcga gccactgtgg cgcttcccaa acgagctgcc aatcgccggt  660
gagccagcga acatcgtcgc gctggtcgaa gaatacatgg actggctgca ccagtcccct  720
gtcccgaagc tgctgttctg gggcacccca ggcgttctga tcccaccggc cgaagccgct  780
cgcctggcca aaagcctgcc taactgcaag gctgtggaca tcggcccggg tctgaatctg  840
ctgcaagaag acaaccccgg acctgatcgg agcgagatcg cgcgctggct gtcgacgctc  900
gagatttccg gcgagccaac cactgaggat ctgtactttc agggtgttcg tagcagcagt  960
cgtaccccga gcgataaacc ggttgcacat gttgttgcaa atccgcaggc cgaaggtcag 1020
ctgcagtggc tgaatcgtcg tgcaaatgca ctgctggcaa atggtgttga actgcgtgat 1080
aatcagctgg ttgttccgag cgaaggtctg tatctgattt atagccaggt tctgtttaaa 1140
ggtcagggtt gtccgagcac acatgttctg ctgacccata ccattagccg tattgcagtt 1200
agctatcaga ccaaagttaa tctgctgagc gcaattaaaa gcccgtgtca gcgtgaaaca 1260
ccggaaggtg ccgaagcaaa accgtggtat gaaccgattt atcttggtgg tgttttttcag 1320
ctggaaaagg gtgatcgtct gagcgcagaa attaatcgtc cggattatct ggattttgca 1380
gaaagcggtc aggtgtattt tggcattatt gcattaggcg gtggttcagg tggtggcggt 1440
tctggtgtta gcggttggcg tctgtttaaa aagattagct aa                    1482

SEQ ID NO: 64           moltype = AA  length = 493
FEATURE                 Location/Qualifiers
REGION                  1..493
                        note = HT-TNF-Beta10*
source                  1..493
                        mol_type = protein
                        organism = synthetic construct
SEQUENCE: 64
MKHHHHHHAE IGTGFPFDPH YVEVLGERMH YVDVGPRDGT PVLFLHGNPT SSYVWRNIIP   60
HVAPTHRCIA PDLIGMGKSD KPDLGYFFDD HVRFMDAFIE ALGLEEVVLV IHDWGSALGF  120
HWAKRNPERV KGIAFMEFIR PIPTWDEWPE FARETFQART TDVGRKLII DQNVFIEGTL   180
PMGVVRPLTE VEMDHYREPF LNPVDREPLW RFPNELPIAG EPANIVALVE EYMDWLHQSP  240
VPKLLFWGTP GVLIPPAEAA RLAKSLPNCK AVDIGPGLNL LQEDNPDLIG SEIARWLSTL  300
EISGEPTTED LYFQGVRSSS RTPSDKPVAH VVANPQAEGQ LQWLNRRANA LLANGVELRD  360
NQLVVPSEGL YLIYSQVLFK GQGCPSTHVL LTHTISRIAV SYQTKVNLLS AIKSPCQRET  420
PEGAEAKPWY EPIYLGGVFQ LEKGDRLSAE INRPDYLDFA ESGQVYFGII ALGGGSGGGG  480
SGVSGWRLFK KIS                                                     493

SEQ ID NO: 65           moltype = DNA  length = 564
FEATURE                 Location/Qualifiers
misc_feature            1..564
                        note = Beta9-TNF
source                  1..564
                        mol_type = other DNA
                        organism = synthetic construct
SEQUENCE: 65
atgggtagta tgctgtttcg tgttaccatt aacagcggtg gtggtagcgg tcatcatcac   60
caccatcacc atcatggtgg tggcagtggt gttcgtagca gcatcgtac cccgagcgat  120
aaaccggttg cacatgttgt tgcaaatccg caggccgaag tcagctgca gtggctgaat   180
cgtcgtgcaa atgcactgct ggcaaatggt gttgaactgc gtgataatca gctggttgtt  240
ccgagcgaag tctgtatct gatttatagc caggttctgt ttaaaggtca gggttgtccg  300
agcacacatg ttctgctgac ccataccatt agccgtatg cagttagcta tcagaccaaa  360
gttaatctgc tgagcgcaat taaaagcccg tgtcagcgtg aaacaccgga aggtgccgaa  420
gcaaaaccgt ggtatgaacc gatttatctt ggtggtgttt tcagctgga aaagggtgat  480
cgtctgagcg cagaaattaa tcgtccggat tatctggatt ttgcagaaag cggtcaggtg  540
tattttggca ttattgcatt ataa                                         564

SEQ ID NO: 66           moltype = AA  length = 187
FEATURE                 Location/Qualifiers
REGION                  1..187
                        note = Beta9-TNF
source                  1..187
                        mol_type = protein
                        organism = synthetic construct
SEQUENCE: 66
MGSMLFRVTI NSGGGSGHHH HHHHGGGSG VRSSSRTPSD KPVAHVVANP QAEGQLQWLN   60
RRANALLANG VELRDNQLVV PSEGLYLIYS QVLFKGQGCP STHVLLTHTI SRIAVSYQTK  120
VNLLSAIKSP CQRETPEGAE AKPWYEPIYL GGVFQLEKGD RLSAEINRPD YLDFAESGQV  180
YFGIIAL                                                            187

SEQ ID NO: 67           moltype = DNA  length = 564
FEATURE                 Location/Qualifiers
misc_feature            1..564
                        note = TNF-Beta9
source                  1..564
                        mol_type = other DNA
```

```
                       organism = synthetic construct
SEQUENCE: 67
atggttcgta gcagcagtcg taccccgagc gataaaccgg ttgcacatgt tgttgcaaat     60
ccgcaggccg aaggtcagct gcagtggctg aatcgtcgtg caaatgcact gctggcaaat    120
ggtgttgaac tgcgtgataa tcagctggtt gttccgagca aggtctgta tctgatttat     180
agccaggttc tgtttaaagg tcaggggttgt ccgagcacac atgttctgct gacccatacc   240
attagccgta ttgcagttag ctatcagacc aaagttaatc tgctgagcgc aattaaaagc    300
ccgtgtcagc gtgaaacacc ggaaggtgcc gaagcaaaac cgtggtatga accgatttat    360
cttggtggtg tttttcagct ggaaaagggt gatcgtctga gcagaaat taatcgtccg      420
gattatctgg attttgcaga aagcggtcag gtgtattttg gcattattgc attaggtggt    480
ggtagcggtc atcatcacca ccatcaccat catggtggtg cagtggtgg tagtatgctg     540
tttcgtgtta ccattaacag ctaa                                           564

SEQ ID NO: 68           moltype = AA   length = 187
FEATURE                 Location/Qualifiers
REGION                  1..187
                        note = TNF-Beta9
source                  1..187
                        mol_type = protein
                        organism = synthetic construct
SEQUENCE: 68
MVRSSSRTPS DKPVAHVVAN PQAEGQLQWL NRRANALLAN GVELRDNQLV VPSEGLYLIY    60
SQVLFKGQGC PSTHVLLTHT ISRIAVSYQT KVNLLSAIKS PCQRETPEGA EAKPWYEPIY   120
LGGVFQLEKG DRLSAEINRP DYLDFAESGQ VYFGIIALGG GSGHHHHHHH HGGGSGGSML   180
FRVTINS                                                             187

SEQ ID NO: 69           moltype = DNA   length = 564
FEATURE                 Location/Qualifiers
misc_feature            1..564
                        note = Beta10*-TNF
source                  1..564
                        mol_type = other DNA
                        organism = synthetic construct
SEQUENCE: 69
atggtgagcg gttggcgtct gttcaaaaaa atcagcggtg gtggtagcgg tcatcatcac     60
caccatcacc atcatggtgg tggcagtggt gttcgtagca gcagtcgtac cccgagcgat    120
aaaccggttg cacatgttgt tgcaaatccg caggccgaag tcagctgca gtggctgaat     180
cgtcgtgcaa atgcactgct ggcaaatggt gttgaactgc gtgataatca gctggttgtt    240
ccgagcgaag gtctgtatct gatttatagc caggttctgt ttaaggtca gggttgtccg    300
agcacacatg ttctgctgac ccataccatt agccgtattg cagttagcta tcagaccaaa   360
gttaatctgc tgagcgcaat taaaagcccg tgtcagcgtg aaacaccgga aggtgccgaa    420
gcaaaaccgt ggtatgaacc gatttatctt ggtggtgttt ttcagctgga aaagggtgat    480
cgtctgagcg cagaaattaa tcgtccggat tatctggatt ttgcagaaag cggtcaggtg    540
tattttggca ttattgcatt ataa                                          564

SEQ ID NO: 70           moltype = AA   length = 187
FEATURE                 Location/Qualifiers
REGION                  1..187
                        note = Beta10*-TNF
source                  1..187
                        mol_type = protein
                        organism = synthetic construct
SEQUENCE: 70
MVSGWRLFKK ISGGGSGHHH HHHHGGGSG VRSSSRTPSD KPVAHVVANP QAEGQLQWLN     60
RRANALLANG VELRDNQLVV PSEGLYLIYS QVLFKGQGCP STHVLLTHTI SRIAVSYQTK   120
VNLLSAIKSP CQRETPEGAE AKPWYEPIYL GGVFQLEKGR LSAEINRPD YLDFAESGQV    180
YFGIIAL                                                             187

SEQ ID NO: 71           moltype = DNA   length = 564
FEATURE                 Location/Qualifiers
misc_feature            1..564
                        note = TNF-Beta10*
source                  1..564
                        mol_type = other DNA
                        organism = synthetic construct
SEQUENCE: 71
atggttcgta gcagcagtcg taccccgagc gataaaccgg ttgcacatgt tgttgcaaat     60
ccgcaggccg aaggtcagct gcagtggctg aatcgtcgtg caaatgcact gctggcaaat    120
ggtgttgaac tgcgtgataa tcagctggtt gttccgagca aggtctgta tctgatttat     180
agccaggttc tgtttaaagg tcaggggttgt ccgagcacac atgttctgct gacccatacc   240
attagccgta ttgcagttag ctatcagacc aaagttaatc tgctgagcgc aattaaaagc    300
ccgtgtcagc gtgaaacacc ggaaggtgcc gaagcaaaac cgtggtatga accgatttat    360
cttggtggtg tttttcagct ggaaaagggt gatcgtctga gcagaaat taatcgtccg      420
gattatctgg attttgcaga aagcggtcag gtgtattttg gcattattgc attaggtggt    480
ggtagcggtc atcatcacca ccatcaccat catggtggtg cagtggtgt gagcggttgg    540
cgtctgttca aaaaaatcag ctaa                                          564

SEQ ID NO: 72           moltype = AA   length = 187
FEATURE                 Location/Qualifiers
```

```
REGION                          1..187
                                note = TNF-Beta10*
source                          1..187
                                mol_type = protein
                                organism = synthetic construct
SEQUENCE: 72
MVRSSSRTPS DKPVAHVVAN PQAEGQLQWL NRRANALLAN GVELRDNQLV VPSEGLYLIY      60
SQVLFKGQGC PSTHVLLTHT ISRIAVSYQT KVNLLSAIKS PCQRETPEGA EAKPWYEPIY     120
LGGVFQLEKG DRLSAEINRP DYLDFAESGQ VYFGIIALGG GSGHHHHHHH HGGGSGVSGW     180
RLFKKIS                                                              187

SEQ ID NO: 73                   moltype = DNA   length = 282
FEATURE                         Location/Qualifiers
misc_feature                    1..282
                                note = Beta9-PpL
source                          1..282
                                mol_type = other DNA
                                organism = synthetic construct
SEQUENCE: 73
atgggtagta tgctgtttcg tgttaccatt aacagcggtg gtggtagcgg tcatcatcac      60
caccatcacc atcatggtgg tggcagtggt agcgaagtga ccattaaagt gaacctgatt     120
tttgcggatg gcaaaattca gaccgcagaa tttaaaggca cctttgaaga agcaacagcc     180
gaagcatatc gttatgcagc actgctggca aaagttaatg gtgaatatac cgcagatctg     240
gaagatggtg gtaatcacat gaatatcaaa ttcgcaggca aa                        282

SEQ ID NO: 74                   moltype = AA    length = 93
FEATURE                         Location/Qualifiers
REGION                          1..93
                                note = Beta9-PpL
source                          1..93
                                mol_type = protein
                                organism = synthetic construct
SEQUENCE: 74
MGSMLFRVTI NSGGGSGHHH HHHHHGGGSG SEVTIKVNLI FADGKIQTAE FKGTFEEATA      60
EAYRYAALLA KVNGEYTADL EDGGNHMNIK FAG                                   93

SEQ ID NO: 75                   moltype = DNA   length = 282
FEATURE                         Location/Qualifiers
misc_feature                    1..282
                                note = PpL-Beta9
source                          1..282
                                mol_type = other DNA
                                organism = synthetic construct
SEQUENCE: 75
atgagcgaag tgaccattaa agtgaacctg attttttgcgg atgcaaaat tcagaccgca      60
gaatttaaag caccctttga agaagcaaca gccgaagcat atcgttatgc agcactgctg     120
gcaaaagtta atggtgaata taccgcagat ctggaagatg gtggtaatca catgaatatc     180
aaattcgcag gcgtggtgg tagcggtcat catcaccacc atcaccatca tggtggtggc     240
agtggtggta gtatgctgtt tcgtgttacc attaacagct aa                        282

SEQ ID NO: 76                   moltype = AA    length = 93
FEATURE                         Location/Qualifiers
REGION                          1..93
                                note = PpL-Beta9
source                          1..93
                                mol_type = protein
                                organism = synthetic construct
SEQUENCE: 76
MSEVTIKVNL IFADGKIQTA EFKGTFEEAT AEAYRYAALL AKVNGEYTAD LEDGGNHMNI      60
KFAGGGGSGH HHHHHHHGGG SGGSMLFRVT INS                                   93

SEQ ID NO: 77                   moltype = DNA   length = 282
FEATURE                         Location/Qualifiers
misc_feature                    1..282
                                note = Beta10-PpL
source                          1..282
                                mol_type = other DNA
                                organism = synthetic construct
SEQUENCE: 77
atggtgagcg gttggcgtct gttcaaaaaa atcagcggtg gtggtagcgg tcatcatcac      60
caccatcacc atcatggtgg tggcagtggt agcgaagtga ccattaaagt gaacctgatt     120
tttgcggatg gcaaaattca gaccgcagaa tttaaaggca cctttgaaga agcaacagcc     180
gaagcatatc gttatgcagc actgctggca aaagttaatg gtgaatatac cgcagatctg     240
gaagatggtg gtaatcacat gaatatcaaa ttcgcaggct aa                        282

SEQ ID NO: 78                   moltype = AA    length = 93
FEATURE                         Location/Qualifiers
REGION                          1..93
                                note = Beta10-PpL
```

| | | |
|---|---|---|
| source | 1..93 | |
| | mol_type = protein | |
| | organism = synthetic construct | |
| SEQUENCE: 78 | | |

MVSGWRLFKK ISGGGSGHHH HHHHHGGGSG SEVTIKVNLI FADGKIQTAE FKGTFEEATA 60
EAYRYAALLA KVNGEYTADL EDGGNHMNIK FAG 93

| | | |
|---|---|---|
| SEQ ID NO: 79 | moltype = DNA length = 282 | |
| FEATURE | Location/Qualifiers | |
| misc_feature | 1..282 | |
| | note = PpL-Beta10* | |
| source | 1..282 | |
| | mol_type = other DNA | |
| | organism = synthetic construct | |
| SEQUENCE: 79 | | | atgagcgaag tgaccattaa agtgaacctg attttgcgg atggcaaaat tcagaccgca 60
gaatttaaag gcacctttga agaagcaaca gccgaagcat atcgttatgc agcactgctg 120
gcaaaagtta atggtgaata taccgcagat ctggaagatg gtggtaatca catgaatatc 180
aaattcgcag gcggtggtgg tagcggtcat catcaccacc atcaccatca tggtggtgcc 240
agtggtgtga gcggttggcg tctgttcaaa aaaatcagct aa 282

| | | |
|---|---|---|
| SEQ ID NO: 80 | moltype = AA length = 93 | |
| FEATURE | Location/Qualifiers | |
| REGION | 1..93 | |
| | note = PpL-Beta10* | |
| source | 1..93 | |
| | mol_type = protein | |
| | organism = synthetic construct | |
| SEQUENCE: 80 | | |

MSEVTIKVNL IFADGKIQTA EFKGTFEEAT AEAYRYAALL AKVNGEYTAD LEDGGNHMNI 60
KFAGGGGSGH HHHHHHGGG SGVSGWRLFK KIS 93

| | | |
|---|---|---|
| SEQ ID NO: 81 | moltype = DNA length = 258 | |
| FEATURE | Location/Qualifiers | |
| misc_feature | 1..258 | |
| | note = Beta9-SpA | |
| source | 1..258 | |
| | mol_type = other DNA | |
| | organism = synthetic construct | |
| SEQUENCE: 81 | | | atgggtagta tgctgtttcg tgttaccatt aacagcggtg gtggtagcgg tcatcatcac 60
caccatcacc atcatggtgg tggcagtggt agctacaaca aagatcagca gagcgccttt 120
tatgaaattc tgaatatgcc gaatctgaat gaagcacagc gcaatggttt tattcagagc 180
ctgaaagatg atccgagcca gagcaccaat gttctggtgt aagcaaaaaa actgaatgaa 240
agccaggcac cgaaataa 258

| | | |
|---|---|---|
| SEQ ID NO: 82 | moltype = AA length = 85 | |
| FEATURE | Location/Qualifiers | |
| REGION | 1..85 | |
| | note = Beta9-SpA | |
| source | 1..85 | |
| | mol_type = protein | |
| | organism = synthetic construct | |
| SEQUENCE: 82 | | |

MGSMLFRVTI NSGGGSGHHH HHHHGGGSG SYNKDQQSAF YEILNMPNLN EAQRNGFIQS 60
LKDDPSQSTN VLGEAKKLNE SQAPK 85

| | | |
|---|---|---|
| SEQ ID NO: 83 | moltype = DNA length = 258 | |
| FEATURE | Location/Qualifiers | |
| misc_feature | 1..258 | |
| | note = SpA-Beta9 | |
| source | 1..258 | |
| | mol_type = other DNA | |
| | organism = synthetic construct | |
| SEQUENCE: 83 | | | atgagctaca acaaagatca gcagagcgcc tttatgaaa ttctgaatat gccgaatctg 60
aatgaagcac agcgcaatgg ttttattcag agcctgaaag atgatccgag ccagagcacc 120
aatgttctgg gtgaagcaaa aaaactgaat gaaagccagg caccgaaagg tggtggtagc 180
ggtcatcatc accaccatca ccatcatggt ggtggcagtg gtggtagtat gctgtttcgt 240
gttaccatta acagctaa 258

| | | |
|---|---|---|
| SEQ ID NO: 84 | moltype = AA length = 85 | |
| FEATURE | Location/Qualifiers | |
| REGION | 1..85 | |
| | note = SpA-Beta9 | |
| source | 1..85 | |
| | mol_type = protein | |
| | organism = synthetic construct | |
| SEQUENCE: 84 | | |

```
MSYNKDQQSA FYEILNMPNL NEAQRNGFIQ SLKDDPSQST NVLGEAKKLN ESQAPKGGGS    60
GHHHHHHHHG GGSGGSMLFR VTINS                                         85

SEQ ID NO: 85              moltype = DNA   length = 258
FEATURE                    Location/Qualifiers
misc_feature               1..258
                           note = Beta10*-SpA
source                     1..258
                           mol_type = other DNA
                           organism = synthetic construct
SEQUENCE: 85
atggtgagcg gttggcgtct gttcaaaaaa atcagcggtg gtggtagcgg tcatcatcac    60
caccatcacc atcatggtgg tggcagtggt agctacaaca aagatcagca gagcgccttt   120
tatgaaattc tgaatatgcc gaatctgaat gaagcacagc gcaatggttt tattcagagc   180
ctgaaagatg atccgagcca gagcaccaat gttctgggtg aagcaaaaaa actgaatgaa   240
agccaggcac cgaaataa                                                 258

SEQ ID NO: 86              moltype = AA   length = 85
FEATURE                    Location/Qualifiers
REGION                     1..85
                           note = Beta10*-SpA
source                     1..85
                           mol_type = protein
                           organism = synthetic construct
SEQUENCE: 86
MVSGWRLFKK ISGGGSGHHH HHHHHGGGSG SYNKDQQSAF YEILNMPNLN EAQRNGFIQS    60
LKDDPSQSTN VLGEAKKLNE SQAPK                                         85

SEQ ID NO: 87              moltype = DNA   length = 258
FEATURE                    Location/Qualifiers
misc_feature               1..258
                           note = SpA-Beta10*
source                     1..258
                           mol_type = other DNA
                           organism = synthetic construct
SEQUENCE: 87
atgagctaca caaagatca gcagagcgcc tttatgaaa ttctgaatat gccgaatctg     60
aatgaagcac agcgcaatgg ttttattcag agcctgaaaa tgatccgag ccagagcacc   120
aatgttctgg gtgaagcaaa aaaactgaat gaaagccagg caccgaaagg tggtggtagc   180
ggtcatcatc accaccatca ccatcatggt ggtggcagtg gtgtgagcgg ttggcgtctg   240
ttcaaaaaaa tcagctaa                                                 258

SEQ ID NO: 88              moltype = AA   length = 85
FEATURE                    Location/Qualifiers
REGION                     1..85
                           note = SpA-Beta10*
source                     1..85
                           mol_type = protein
                           organism = synthetic construct
SEQUENCE: 88
MSYNKDQQSA FYEILNMPNL NEAQRNGFIQ SLKDDPSQST NVLGEAKKLN ESQAPKGGGS    60
GHHHHHHHHG GGSGVSGWRL FKKIS                                         85

SEQ ID NO: 89              moltype = DNA   length = 267
FEATURE                    Location/Qualifiers
misc_feature               1..267
                           note = Beta9-SpGA1
source                     1..267
                           mol_type = other DNA
                           organism = synthetic construct
SEQUENCE: 89
atgggtagta tgctgtttcg tgttaccatt aacagcggtg gtggtagcgg tcatcatcac    60
caccatcacc atcatggtgg tggcagtggt gcagtgacca cctataaact ggttattaat   120
ggtcgtaccc tgagcggtta taccaccacc accgcagttg atgcagaaac cgcagaaaaa   180
gcatttaaac agtatgccta tgtgcatgaa gttgatggtg tttggaccta tgatgatgca   240
accaaaacct ttaccgttac cgaataa                                       267

SEQ ID NO: 90              moltype = AA   length = 88
FEATURE                    Location/Qualifiers
REGION                     1..88
                           note = Beta9-SpGA1
source                     1..88
                           mol_type = protein
                           organism = synthetic construct
SEQUENCE: 90
MGSMLFRVTI NSGGGSGHHH HHHHHGGGSG AVTTYKLVIN GRTLSGYTTT TAVDAETAEK    60
AFKQYAYVHE VDGVWTYDDA TKTFTVTE                                      88

SEQ ID NO: 91              moltype = DNA   length = 267
```

```
FEATURE                 Location/Qualifiers
misc_feature            1..267
                        note = SpGA1-Beta9
source                  1..267
                        mol_type = other DNA
                        organism = synthetic construct
SEQUENCE: 91
atggcagtga ccacctataa actggttatt aatggtcgta ccctgagcgg ttataccacc    60
accaccgcag ttgatgcaga aaccgcagaa aaagcattta acagtatgc ctatgtgcat    120
gaagttgatg gtgtttggac ctatgatgat gcaaccaaaa cctttaccgt taccgaaggt   180
ggtggtagcg gtcatcatca ccaccatcac catcatggtg gtggcagtgg tggtagtatg   240
ctgtttcgtg ttaccattaa cagctaa                                       267

SEQ ID NO: 92           moltype = AA   length = 88
FEATURE                 Location/Qualifiers
REGION                  1..88
                        note = SpGA1-Beta9
source                  1..88
                        mol_type = protein
                        organism = synthetic construct
SEQUENCE: 92
MAVTTYKLVI NGRTLSGYTT TTAVDAETAE KAFKQYAYVH EVDGVWTYDD ATKTFTVTEG    60
GGSGHHHHHH HHGGGSGGSM LFRVTINS                                      88

SEQ ID NO: 93           moltype = DNA   length = 267
FEATURE                 Location/Qualifiers
misc_feature            1..267
                        note = Beta10*-SpGA1
source                  1..267
                        mol_type = other DNA
                        organism = synthetic construct
SEQUENCE: 93
atggtgagcg gttggcgtct gttcaaaaaa atcagcggtg gtggtagcgg tcatcatcac    60
caccatcacc atcatggtgg tggcagtggt gcagtgacca cctataaact ggttattaat   120
ggtcgtaccc tgagcggtta taccaccacc accgcagttg atgcagaaac cgcagaaaaa   180
gcatttaaac agtatgccta tgtgcatgaa gttgatggtg tttggaccta tgatgatgca   240
accaaaacct ttaccgttac cgaataa                                       267

SEQ ID NO: 94           moltype = AA   length = 88
FEATURE                 Location/Qualifiers
REGION                  1..88
                        note = Beta10*-SpGA1
source                  1..88
                        mol_type = protein
                        organism = synthetic construct
SEQUENCE: 94
MVSGWRLFKK ISGGGSGHHH HHHHGGGSG AVTTYKLVIN GRTLSGYTTT TAVDAETAEK    60
AFKQYAYVHE VDGVWTYDDA TKTFTVTE                                      88

SEQ ID NO: 95           moltype = DNA   length = 267
FEATURE                 Location/Qualifiers
misc_feature            1..267
                        note = SpGA1-Beta10
source                  1..267
                        mol_type = other DNA
                        organism = synthetic construct
SEQUENCE: 95
atggcagtga ccacctataa actggttatt aatggtcgta ccctgagcgg ttataccacc    60
accaccgcag ttgatgcaga aaccgcagaa aaagcattta acagtatgc ctatgtgcat    120
gaagttgatg gtgtttggac ctatgatgat gcaaccaaaa cctttaccgt taccgaaggt   180
ggtggtagcg gtcatcatca ccaccatcac catcatggtg gtggcagtgg tgtgagcggt   240
tggcgtctgt tcaaaaaaat cagctaa                                       267

SEQ ID NO: 96           moltype = AA   length = 88
FEATURE                 Location/Qualifiers
REGION                  1..88
                        note = SpGA1-Beta10*
source                  1..88
                        mol_type = protein
                        organism = synthetic construct
SEQUENCE: 96
MAVTTYKLVI NGRTLSGYTT TTAVDAETAE KAFKQYAYVH EVDGVWTYDD ATKTFTVTEG    60
GGSGHHHHHH HHGGGSGVSG WRLFKKIS                                      88
```